United States Patent
Kuchroo et al.

(10) Patent No.: US 7,741,271 B2
(45) Date of Patent: Jun. 22, 2010

(54) METHODS OF MODULATING IMMUNE RESPONSES BY MODULATING TIM-1, TIM-2 AND TIM-4 FUNCTION

(75) Inventors: Vijay K. Kuchroo, Newton, MA (US); Sumone Chakravarti, Oakland, CA (US); Terry Strom, Brookline, MA (US); Xin Xiao Zheng, Wellesley, MA (US); Jennifer Meyers, Brighton, MA (US)

(73) Assignees: The Brigham and Women's Hospital, Inc., Boston, MA (US); Beth Israel Deaconess Medical Center, Inc., Boston, MA (US)

(*) Notice: Subject to any disclaimer, the term of this patent is extended or adjusted under 35 U.S.C. 154(b) by 0 days.

(21) Appl. No.: 11/080,091

(22) Filed: Mar. 14, 2005

(65) Prior Publication Data

US 2005/0261224 A1 Nov. 24, 2005

Related U.S. Application Data

(60) Provisional application No. 60/552,523, filed on Mar. 12, 2004, provisional application No. 60/622,559, filed on Oct. 27, 2004.

(51) Int. Cl.
*A61K 38/00* (2006.01)
*A61K 45/00* (2006.01)
*A61K 47/00* (2006.01)
(52) U.S. Cl. .................................. 514/2; 424/278.1
(58) Field of Classification Search .................... None
See application file for complete search history.

(56) References Cited

U.S. PATENT DOCUMENTS

| | | | |
|---|---|---|---|
| 6,027,916 A | 2/2000 | Ni et al. | |
| 6,066,322 A | 5/2000 | Levinson | |
| 6,066,498 A | 5/2000 | Levinson | |
| 6,084,083 A | 7/2000 | Levinson | |
| 6,156,887 A | 12/2000 | Levinson | |
| 6,190,909 B1 | 2/2001 | Levinson et al. | |
| 6,204,371 B1 | 3/2001 | Levinson | |
| 6,288,218 B1 | 9/2001 | Levinson | |
| 6,414,117 B1 | 7/2002 | Levinson | |
| 6,455,685 B1 | 9/2002 | Levinson | |
| 6,468,768 B1 | 10/2002 | Ni et al. | |
| 6,562,343 B1 | 5/2003 | Levinson | |
| 2003/0069196 A1 | 4/2003 | Levinson et al. | |
| 2003/0124114 A1 | 7/2003 | McIntire et al. | |
| 2004/0005322 A1 | 1/2004 | Kuchroo et al. | |
| 2005/0276756 A1* | 12/2005 | Hoo et al. ........ | 424/1.49 |

FOREIGN PATENT DOCUMENTS

| | | |
|---|---|---|
| WO | WO-98/15624 | 10/1997 |
| WO | WO 99/35158 | 7/1999 |
| WO | WO 01/57188 | 8/2001 |
| WO | WO-0155304 | 9/2001 |
| WO | WO-02081517 | 10/2002 |
| WO | WO-03/002722 A2 | 1/2003 |
| WO | WO-03/063792 A2 | 8/2003 |
| WO | WO 03/080673 | 10/2003 |
| WO | WO 2004/060041 | 7/2004 |
| WO | WO 2005/027854 | 3/2005 |

OTHER PUBLICATIONS

Loza et al., 2005, Clin. Exp. Allergy, vol. 35: 8-17 de Souza et al., 2005, PNAS, vol. 102: 17113-17118.*
Meyers et al., 2005, Trends in Mol. Med. vol. 11: 362-369.*
Meyers et al., 2005, Nat. Immunol. vol. 6: 455-464.*
Burgess et al., 1990, J. Cell. Biol. vol. 111: 2129-2138.*
Mikayama, 1993, PNAS, vol. 90: 10056-60. Whisstock et al., 2003, Quart. Rev. Biophys. vol. 36: 307-340.*
Lazar et al., 1988, Mol. Cell. Biol. vol. 8: 1247-1252. Encinas et al., 2005, J. Allergy Clin. Immunol. vol. 116: 1343-9.*
Santiago et al., 2007, Immunity, vol. 26: 299-310. Singh, 2003, Clin. Immunol. vol. 108: 73-79.*
Theofilopoulos et al. Arthritis Res. vol. 3: 136-141.*
No Author-Sequence Curated my NCBI staff: "Galectin 9 short isoform (human)"; Genbank Accession No. NP_002299; (First published online on Mar. 24, 1999).
No Author-Sequence Curated my NCBI staff: Genbank Accession No. NP_033665, galection 9 long isoform (human). (First published online on Jan. 28, 2000).
No Author-Sequence Curated my NCBI staff: Genbank Accession No. NP_034838, lectin, galactose binding, soluble 9 (mouse). (First published online on Jan. 26, 2000 ).
No Author-Sequence Curated my NCBI staff: Genbank Accession No. NP_036338; hepatitis A virus cellular receptor 1 [Homo sapiens] (First published online on Feb. 7, 2000).
No Author-Sequence Curated my NCBI staff: Genbank Accession No. NM_012206; Homo sapiens hepatitis A virus cellular receptor 1 (HAVCR1), mRNA. (First published online on Feb. 7, 2000).
No Author-Sequence Curated my NCBI staff: Genbank Accession No. NP_599009; hepatitis A virus cellular receptor 1 [Mus musculus]. (First published online on Feb. 7, 2000).

*Primary Examiner*—Amy E Juedes
(74) *Attorney, Agent, or Firm*—Nixon Peabody LLP

(57) ABSTRACT

The invention relates to methods of modulating immune responses in a subject, such as by administering to the subject agents which modulate tim-1, tim-2 or tim-4 activity, or which modulate the physical interaction between tim-1 and tim-4 or between tim-2 and a tim-2 ligand. Immune responses include, but are not limited to, autoimmune disorders, transplantation tolerance, and Th1 and Th2-mediated responses and disorders. The invention also relates to novel assays for identifying agents which modulate the physical interaction between tim-1 and tim-4. In addition, the invention relates to novel soluble tim-4 polypeptides and to nucleic acids which encode them.

12 Claims, 34 Drawing Sheets

OTHER PUBLICATIONS

No Author-Sequence Curated my NCBI staff. Genbank Accession No. NM_134248; Mus musculus hepatitis A virus cellular receptor 1 (Havcr1), mRNA (First published online on Mar. 18, 2002).

No Author-Sequence Curated my NCBI staff: Genbank Accession No. NP_599010; T-cell immunoglobulin and mucin domain containing 2 [Mus musculus]. (First published online on Mar. 18, 2002).

No Author-Sequence Curated my NCBI staff: Genbank Accession No. NM_134249; Mus musculus T-cell immunoglobulin and mucin domain containing 2(Timd2), mRNA. (First published online on Mar. 18, 2002).

No Author-Sequence Curated my NCBI staff: Genbank Accession No. NP_848874; T-cell immunoglobulin and mucin domain containing 4 [Mus musculus]. (First published online on May 10, 2003).

No Author-Sequence Curated my NCBI staff: Genbank Accession No. NM_178759; Mus musculus T-cell immunoglobulin and mucin domain containing 4 (Timd4), mRNA (First published online on May 10, 2003).

No Author-Sequence Curated my NCBI staff: Genbank Accession No. NP_071762; semaphorin B [Homo sapiens]. (First published online on Dec. 12, 2000).

Bailly et al. Shedding of kidney injury molecule-1, a putative adhesion protein involved in renal regeneration. *J Biol Chem.* 2002;277(42):39739-48.

Chae Sc. et al. The exon 4 variations of Tim-1 gene are associated with rheumatoid arthritis in a Korean population. *Biochem Biophys Res Commun.* 2004;315(4):971-5.

U.S. Appl. No. 10/958,169, filed Oct. 4, 2004, Kuchroo et al.

Chae Sc. et al. The association of the exon 4 variations of Tim-1 gene with allergic diseases in a Korean population. *Biochem Biophys Res Commun.* 2003;312(2):346-50.

Chae Sc. et al. Molecular variations in the promoter and coding regions of human Tim-1 gene and their association in Koreans with asthma. *Hum Immunol.* 2003; 64(12):1177-82.

Feigelstock D. et al. The human homolog of HAVcr-1 codes for a hepatitis A virus cellular receptor. *J Virol.* 1998;72(8):6621-8.

Ichimura T. et al. Kidney injury molecule-1 (KIM-1), a putative epithelial cell adhesion molecule containing a novel immunoglobulin domain, is up-regulated in renal cells after injury. *J Biol Chem.* 1998;273(7):4135-42.

Kaplan, G. et al. Identification of a surface glycoprotein on African green monkey kidney cells as a receptor for hepatitis A virus. EMBO J. 15, 4282-4296 (1996).

Khademi M. et al. T Cell Ig- and mucin-domain-containing molecule-3 (TIM-3) and TIM-1 molecules are differentially expressed on human Th1 and Th2 cells and in cerebrospinal fluid-derived mononuclear cells in multiple sclerosis. *J. Immunol.* 2004;172(11):7169-76.

Kikutani H. et al. Semaphorins in interactions between T cells and antigen-presenting cells. *Nat Rev Immunol.* 2003;3(2):159-67.

Kuchroo, V. et al. The TIM gene family: emerging roles in immunity and disease. Nat Rev Immunol 3, 454-462 (2003).

Kumanogoh A. et al. Immune semaphorins: a new area of semaphorin research. *J Cell Sci.* 2003;116(Pt 17):3463-70.

Kumanogoh A. et al. Class IV semaphorin Sema4A enhances T-cell activation and interacts with Tim-2. *Nature.* 2002; 419(6907):629-33.

McIntire JJ. et al. TIM-1, a novel allergy and asthma susceptibility gene. Springer Semin Immunopathol. 2004;25(3-4):335-48. Epub Oct. 24, 2003.

McIntire, J. et al. Identification of Tapr (an airway hyperreactivity regulatory locus) and the linked Tim gene family. Nat Immunol 2, 1109-1116 (2001).

Monney L. et al. Th1-specific cell surface protein Tim-3 regulates macrophage activation and severity of an autoimmune disease. *Nature.* 2002;415(6871):536-41.

Noguchi E. et al. Insertion/deletion coding polymorphisms in hHAVcr-1 are not associated with atopic asthma in the Japanese population. *Genes Immun.* 2003;4(2):170-3.

Rabinovich GA. et al. Galectins and their ligands: amplifiers, silencers or tuners of the inflammatory response? *Trends Immunol* 23:313-320; 2002.

Rabinovich GA. et al. Role of galectins in inflammatory and immunomodulatory processes *Biochim Biophys Acta* 1572:274-284, 2002.

Sabatos CA. et al. Interaction of Tim-3 and Tim-3 ligand regulates T helper type 1 responses and induction of peripheral tolerance. *Nat Immunol* 4:1102-1110, 2003.

Sanchez-Fueyo, A. et al. The Ig superfamily member Tim-3 inhibits Th1-mediated auto- and allo-immune response and promotes immunological tolerance. *Nat Immunol* 4:1093-1101, 2003.

Shakhov AN. et al. Smuckler/TIM4 is a distinct member of TIM family expressed by stromal cells of secondary lymphoid tissues and associated with lymphotoxin signaling. *Eur J Immunol.* 2004;34(2):494-503.

Silberstein E. et al. Neutralization of hepatitis A virus (HAV) by an immunoadhesin containing the cysteine-rich region of HAV cellular receptor-1. *J Virol.* 2001;75(2):717-25.

Thompson, P. et al. The Cys-rich region of hepatitis A virus cellular receptor 1 is required for binding of hepatitis A virus and protective monoclonal antibody 190/4. J Virol 72, 3751-3761 (1998).

Tureci et al. Molecular definition of a novel human galectin which is immunogenic in patients with Hodgkin's disease. *J Biol Chem.* 1997;272(10):6416-22.

Xing, L. et al. Distinct cellular receptor interactions in poliovirus and rhinoviruses. EMBO J. 19, 1207-1216 (2000).

McIntire, J.J. et al. Hepatitis A virus link to atopic disease, Nature, vol. 425, Oct. 2003, 576.

Von Hertzen, Puzzling associations between childhood infections and the later occureance of asthma and atopy, Ann Med 2000; 32:397-400.

Racioppi, L. et al., Peptide-Major Histocompatibility Complex Class II Complexes with Mixed Agonist/Antagonist Properties Provide Evidence for Ligand-related Differences in T Cell Receptor-dependent Intracellular Signaling, The Journal of Experimental Medicine, vol. 177, Apr. 1993 1047-1060.

Matricardi, P. et al., Hay fever and asthma in relation to markers of infection in the United States, J Allergy Clin Immunol. Sep. 2002, 381-387.

Silberstein, E. et al., Alteration of Hepatitis A Virus (HAV) Particles by a Soluble Form of HAV Cellular Receptor 1 Containing the Immunoglobulin—and Mucin-Like Regions, Journal of Virology, Aug. 2003, vol. 77. No. 6, 8765-8774.

Matricardi, P. et al., Cross sectonal retrospective study of prevalence of atopy among Italian military students with antibodies against hepatitis a virus, BMJ 1997;314-999.

Bodner, C. et al., Childhood exposure to infection and risk of adult onset wheeze and atopy, Thorax 2000;55:383-387.

* cited by examiner

D10G4

AE7

TIM-2          TIM-3

Full-length

Lacks part of mucin --> frameshift, premature stop

Possible splice variants

Lacks part of mucin and all of transmembrane domain

SEQUENCE LISTING

<160> NUMBER OF SEQ ID NOS: 22

<210> SEQ ID NO 1
<211> LENGTH: 359
<212> TYPE: PRT
<213> ORGANISM: Homo sapiens

<400> SEQUENCE: 1

Met His Pro Gln Val Val Ile Leu Ser Leu Ile Leu His Leu Ala Asp
1               5                   10                  15

Ser Val Ala Gly Ser Val Lys Val Gly Gly Glu Ala Gly Pro Ser Val
                20                  25                  30

Thr Leu Pro Cys His Tyr Ser Gly Ala Val Thr Ser Met Cys Trp Asn
            35                  40                  45

Arg Gly Ser Cys Ser Leu Phe Thr Cys Gln Asn Gly Ile Val Trp Thr
        50                  55                  60

Asn Gly Thr His Val Thr Tyr Arg Lys Asp Thr Arg Tyr Lys Leu Leu
65                  70                  75                  80

Gly Asp Leu Ser Arg Arg Asp Val Ser Leu Thr Ile Glu Asn Thr Ala
                85                  90                  95

Val Ser Asp Ser Gly Val Tyr Cys Cys Arg Val Glu His Arg Gly Trp
            100                 105                 110

Phe Asn Asp Met Lys Ile Thr Val Ser Leu Glu Ile Val Pro Pro Lys
        115                 120                 125

Val Thr Thr Thr Pro Ile Val Thr Thr Val Pro Thr Val Thr Thr Val
    130                 135                 140

Arg Thr Ser Thr Thr Val Pro Thr Thr Thr Thr Val Pro Thr Thr Thr
145                 150                 155                 160

Val Pro Thr Thr Met Ser Ile Pro Thr Thr Thr Val Pro Thr Thr Thr
                165                 170                 175

Met Thr Val Ser Thr Thr Thr Ser Val Pro Thr Thr Thr Ser Ile Pro
            180                 185                 190

Thr Thr Thr Ser Val Pro Val Thr Thr Thr Val Ser Thr Phe Val Pro
        195                 200                 205

Pro Met Pro Leu Pro Arg Gln Asn His Glu Pro Val Ala Thr Ser Pro
    210                 215                 220

Ser Ser Pro Gln Pro Ala Glu Thr His Pro Thr Thr Leu Gln Gly Ala
225                 230                 235                 240

```
Ile Arg Arg Glu Pro Thr Ser Ser Pro Leu Tyr Ser Tyr Thr Thr Asp
            245                 250                 255

Gly Asn Asp Thr Val Thr Glu Ser Ser Asp Gly Leu Trp Asn Asn Asn
            260                 265                 270

Gln Thr Gln Leu Phe Leu Glu His Ser Leu Leu Thr Ala Asn Thr Thr
            275                 280                 285

Lys Gly Ile Tyr Ala Gly Val Cys Ile Ser Val Leu Val Leu Leu Ala
            290                 295                 300

Leu Leu Gly Val Ile Ile Ala Lys Lys Tyr Phe Phe Lys Lys Glu Val
305                 310                 315                 320

Gln Gln Leu Ser Val Ser Phe Ser Ser Leu Gln Ile Lys Ala Leu Gln
            325                 330                 335

Asn Ala Val Glu Lys Glu Val Gln Ala Glu Asp Asn Ile Tyr Ile Glu
            340                 345                 350

Asn Ser Leu Tyr Ala Thr Asp
            355

<210> SEQ ID NO 2
<211> LENGTH: 305
<212> TYPE: PRT
<213> ORGANISM: Mouse

<400> SEQUENCE: 2

Met Asn Gln Ile Gln Val Phe Ile Ser Gly Leu Ile Leu Leu Leu Pro
1               5                   10                  15

Gly Thr Val Asp Ser Tyr Val Glu Val Lys Gly Val Val Gly His Pro
            20                  25                  30

Val Thr Leu Pro Cys Thr Tyr Ser Thr Tyr Arg Gly Ile Thr Thr Thr
            35                  40                  45

Cys Trp Gly Arg Gly Gln Cys Pro Ser Ser Ala Cys Gln Asn Thr Leu
    50                  55                  60

Ile Trp Thr Asn Gly His Arg Val Thr Tyr Gln Lys Ser Ser Arg Tyr
65              70                  75                  80

Asn Leu Lys Gly His Ile Ser Glu Gly Asp Val Ser Leu Thr Ile Glu
            85                  90                  95

Asn Ser Val Glu Ser Asp Ser Gly Leu Tyr Cys Cys Arg Val Glu Ile
            100                 105                 110

Pro Gly Trp Phe Asn Asp Gln Lys Val Thr Phe Ser Leu Gln Val Lys
            115                 120                 125

Pro Glu Ile Pro Thr Arg Pro Pro Thr Arg Pro Thr Thr Thr Arg Pro
            130                 135                 140

Thr Ala Thr Gly Arg Pro Thr Thr Ile Ser Thr Arg Ser Thr His Val
145                 150                 155                 160

Pro Thr Ser Ile Arg Val Ser Thr Ser Thr Pro Pro Thr Ser Thr His
            165                 170                 175

Thr Trp Thr His Lys Pro Glu Pro Thr Thr Phe Cys Pro His Glu Thr
            180                 185                 190

Thr Ala Glu Val Thr Gly Ile Pro Ser His Thr Pro Thr Asp Trp Asn
            195                 200                 205

Gly Thr Val Thr Ser Ser Gly Asp Thr Trp Ser Asn His Thr Glu Ala
            210                 215                 220

Ile Pro Pro Gly Lys Pro Gln Lys Asn Pro Thr Lys Gly Phe Tyr Val
225                 230                 235                 240

Gly Ile Cys Ile Ala Ala Leu Leu Leu Leu Leu Leu Val Ser Thr Val
```

```
                    245                 250                 255
Ala Ile Thr Arg Tyr Ile Leu Met Lys Arg Lys Ser Ala Ser Leu Ser
            260                 265                 270

Val Val Ala Phe Arg Val Ser Lys Ile Glu Ala Leu Gln Asn Ala Ala
            275                 280                 285

Val Val His Ser Arg Ala Glu Asp Asn Ile Tyr Ile Val Glu Asp Arg
            290                 295                 300

Pro
305

<210> SEQ ID NO 3
<211> LENGTH: 378
<212> TYPE: PRT
<213> ORGANISM: Homo sapiens

<400> SEQUENCE: 3

Met Ser Lys Glu Pro Leu Ile Leu Trp Leu Met Ile Glu Phe Trp Trp
 1               5                  10                  15

Leu Tyr Leu Thr Pro Val Thr Ser Glu Thr Val Val Thr Glu Val Leu
            20                  25                  30

Gly His Arg Val Thr Leu Pro Cys Leu Tyr Ser Ser Trp Ser His Asn
            35                  40                  45

Ser Asn Ser Met Cys Trp Gly Lys Asp Gln Cys Pro Tyr Ser Gly Cys
 50                  55                  60

Lys Glu Ala Leu Ile Arg Thr Asp Gly Met Arg Val Thr Ser Arg Lys
65                  70                  75                  80

Ser Ala Lys Tyr Arg Leu Gln Gly Thr Ile Pro Arg Gly Asp Val Ser
                85                  90                  95

Leu Thr Ile Leu Asn Pro Ser Glu Ser Asp Ser Gly Val Tyr Cys Cys
            100                 105                 110

Arg Ile Glu Val Pro Gly Trp Phe Asn Asp Val Lys Ile Asn Val Arg
            115                 120                 125

Leu Asn Leu Gln Arg Ala Ser Thr Thr Thr His Arg Thr Ala Thr Thr
        130                 135                 140

Thr Thr Arg Arg Thr Thr Thr Ser Pro Thr Thr Thr Arg Gln Met Thr
145                 150                 155                 160

Thr Thr Thr Pro Ala Ala Leu Pro Thr Thr Val Val Thr Thr Pro Asp
                165                 170                 175

Leu Thr Thr Gly Thr Pro Leu Gln Met Thr Thr Ile Ala Val Phe Thr
            180                 185                 190

Thr Ala Asn Thr Cys Leu Ser Leu Thr Pro Ser Thr Leu Pro Glu Glu
            195                 200                 205

Ala Thr Gly Leu Leu Thr Pro Glu Pro Ser Lys Glu Gly Pro Ile Leu
        210                 215                 220

Thr Ala Glu Ser Glu Thr Val Leu Pro Ser Asp Ser Trp Ser Ser Ala
225                 230                 235                 240

Glu Ser Thr Ser Ala Asp Thr Val Leu Leu Thr Ser Lys Glu Ser Lys
                245                 250                 255

Val Trp Asp Leu Pro Ser Thr Ser His Val Ser Met Trp Lys Thr Ser
            260                 265                 270

Asp Ser Val Ser Ser Pro Gln Pro Gly Ala Ser Asp Thr Ala Val Pro
            275                 280                 285

Glu Gln Asn Lys Thr Thr Lys Thr Gly Gln Met Asp Gly Ile Pro Met
        290                 295                 300
```

```
Ser Met Lys Asn Glu Met Pro Ile Ser Gln Leu Leu Met Ile Ile Ala
305                 310                 315                 320

Pro Ser Leu Gly Phe Val Leu Phe Ala Leu Phe Val Ala Phe Leu Leu
            325                 330                 335

Arg Gly Lys Leu Met Glu Thr Tyr Cys Ser Gln Lys His Thr Arg Leu
            340                 345                 350

Asp Tyr Ile Gly Asp Ser Lys Asn Val Leu Asn Asp Val Gln His Gly
            355                 360                 365

Arg Glu Asp Glu Asp Gly Leu Phe Thr Leu
            370                 375

<210> SEQ ID NO 4
<211> LENGTH: 343
<212> TYPE: PRT
<213> ORGANISM: Mouse

<400> SEQUENCE: 4

Met Ser Lys Gly Leu Leu Leu Trp Leu Val Met Glu Leu Trp Trp
  1               5                  10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
 50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
            115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
            195                 200                 205

Ile Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ile Ala Cys Cys Val Gly
            275                 280                 285

Phe Val Leu Met Val Leu Leu Phe Leu Ala Phe Leu Leu Arg Gly Lys
            290                 295                 300
```

-continued

Val Thr Gly Ala Asn Cys Leu Gln Arg His Lys Arg Pro Asp Asn Thr
305                 310                 315                 320

Glu Asp Ser Asp Ser Val Leu Asn Asp Met Ser His Gly Arg Asp Asp
            325                 330                 335

Glu Asp Gly Ile Phe Thr Leu
            340

<210> SEQ ID NO 5
<211> LENGTH: 1440
<212> TYPE: DNA
<213> ORGANISM: Homo sapiens

<400> SEQUENCE: 5

| | | | | | |
|---|---|---|---|---|---|
| gttacccagc | attgtgagtg | acagagcctg | gatctgaacg | ctgatcccat | aatgcatcct | 60 |
| caagtggtca | tcttaagcct | catcctacat | ctggcagatt | ctgtagctgg | ttctgtaaag | 120 |
| gttggtggag | aggcaggtcc | atctgtcaca | ctaccctgcc | actacagtgg | agctgtcaca | 180 |
| tcaatgtgct | ggaatagagg | ctcatgttct | ctattcacat | gccaaaatgg | cattgtctgg | 240 |
| accaatggaa | cccacgtcac | ctatcggaag | gacacacgct | ataagctatt | ggggaccttt | 300 |
| tcaagaaggg | atgtctcttt | gaccatagaa | atacagctg | tgtctgacag | tggcgtatat | 360 |
| tgttgccgtg | ttgagcaccg | tgggtggttc | aatgacatga | aaatcaccgt | atcattggag | 420 |
| attgtgccac | ccaaggtcac | gactactcca | attgtcacaa | ctgttccaac | cgtcacgact | 480 |
| gttcgaacga | gcaccactgt | tccaacgaca | acgactgttc | caacgacaac | tgttccaaca | 540 |
| acaatgagca | ttccaacgac | aacgactgtt | ccgacgacaa | tgactgtttc | aacgacaacg | 600 |
| agcgttccaa | cgacaacgag | cattccaaca | caacaagtg | ttccagtgac | aacaacggtc | 660 |
| tctacctttg | ttcctccaat | gcctttgccc | aggcagaacc | atgaaccagt | agccacttca | 720 |
| ccatcttcac | ctcagccagc | agaaaccac | cctacgacac | tgcagggagc | aataaggaga | 780 |
| gaacccacca | gctcaccatt | gtactcttac | acaacagatg | ggaatgacac | cgtgacagag | 840 |
| tcttcagatg | gccttttggaa | taacaatcaa | actcaactgt | tcctagaaca | tagtctactg | 900 |
| acggccaata | ccactaaagg | aatctatgct | ggagtctgta | tttctgtctt | ggtgcttctt | 960 |
| gctcttttgg | gtgtcatcat | tgccaaaaag | tatttcttca | aaaaggaggt | tcaacaacta | 1020 |
| agtgtttcat | ttagcagcct | tcaaattaaa | gctttgcaaa | atgcagttga | aaaggaagtc | 1080 |
| caagcagaag | acaatatcta | cattgagaat | agtctttatg | ccacggacta | agacccagtg | 1140 |
| gtgctctttg | agagtttacg | cccatgactg | cagaagactg | aacaggtatc | agcacatcag | 1200 |
| atgtctttta | gactccaaga | caattttttct | gtttcagttt | catctggcat | tccaacatgt | 1260 |
| cagtgatact | gggtagagta | actctcccac | tccaaactgt | gtatagtcaa | cctcatcatt | 1320 |
| aatgtagtcc | taatttgttt | tgctaaaact | ggctcaatcc | ttctgatcat | tgcagagttt | 1380 |
| tctctcaaac | atgaacactt | tagaattgta | tgttctcttt | agaccccata | aatcctgtat | 1440 |

<210> SEQ ID NO 6
<211> LENGTH: 918
<212> TYPE: DNA
<213> ORGANISM: Mouse

<400> SEQUENCE: 6

| | | | | | |
|---|---|---|---|---|---|
| atgaatcaga | ttcaagtctt | catttcaggc | ctcatactgc | ttctcccagg | cactgtggat | 60 |
| tcttatgtgg | aagtaaaggg | ggtagtgggt | caccctgtca | cacttccatg | tacttactca | 120 |
| acatatcgtg | gaatcacaac | gacatgttgg | ggccgagggc | aatgcccatc | ttctgcttgt | 180 |

```
caaaatacac ttatttggac caatggacat cgtgtcacct atcagaagag cagtcggtac    240
aacttaaagg ggcatatttc agaaggagat gtgtccttga cgatagagaa ctctgttgag    300
agtgacagtg gtctgtattg ttgtcgagtg gagattcctg gatggtttaa tgatcagaaa    360
gtgacctttt cattgcaagt taaaccagag attcccacac gtcctccaac aagacccaca    420
actacaaggc ccacagctac aggaagaccc acgactattt caacaagatc acacacatgta   480 ccaacatcaa tcagagtctc tacctccact cctccaacat ctacacacac atggactcac    540
aaaccagaac ccactacatt ttgtccccat gagacaacag ctgaggtgac aggaatccca    600
tcccatactc ctacagactg gaatggcact gtgacatcct caggagatac ctggagtaat    660
cacactgaag caatccctcc agggaagccg cagaaaaacc ctactaaggg cttctatgtt    720
ggcatctgca tcgcagccct gctgctactg ctccttgtga gcaccgtggc tatcaccagg    780
tacatactta tgaaaaggaa gtcagcatct ctaagcgtgg ttgccttccg tgtctctaag    840
attgaagctt tgcagaacgc agcggttgtg cattcccgag ctgaagacaa catctacatt    900
gttgaagata gaccttga                                                  918

<210> SEQ ID NO 7
<211> LENGTH: 1156
<212> TYPE: DNA
<213> ORGANISM: Homo sapiens

<400> SEQUENCE: 7
atgtccaaag aacctctcat tctctggctg atgattgagt tttggtggct ttacctgaca     60
ccagtcactt cagagactgt tgtgacggag gttttgggtc accgggtgac tttgccctgt    120
ctgtactcat cctggtctca aacagcaac agcatgtgct gggggaaaga ccagtgcccc     180
tactccggtt gcaaggaggc gctcatccgc actgatggaa tgagggtgac ctcaagaaag    240
tcagcaaaat atagacttca ggggactatc ccgagaggtg atgtctcctt gaccatctta    300
aaccccagtg aaagtgacag cggtgtgtac tgctgccgca tagaagtgcc tggctggttc    360
aacgatgtaa agataaacgt gcgcctgaat ctacagagag cctcaacaac cacgcacaga    420
acagcaacca ccaccacacg cagaacaaca acaacaagcc ccaccaccac ccgacaaatg    480
acaacaaccc cagctgcact tccaacaaca gtcgtgacca caccgatct cacaaccgga     540 acaccactcc agatgacaac cattgccgtc ttcacaacag caaacacgtg cctttcacta    600
accccaagca cccttccgga ggaagccaca ggtcttctga ctcccgagcc ttctaaggaa    660
gggcccatcc tcactgcaga atcagaaact gtcctcccca gtgattcctg gagtagtgct    720
gagtctactt ctgctgacac tgtcctgctg acatccaaag agtccaaagt ttgggatctc    780
ccatcaacat cccacgtgtc aatgtggaaa acgagtgatt ctgtgtcttc tcctcagcct    840
ggagcatctg atacagcagt tcctgagcag aacaaaacaa caaaaacagg acagatggat    900 ggaatacccca tgtcaatgaa gaatgaaatg cccatctccc aactactgat gatcatcgcc    960
ccctccttgg gatttgtgct cttcgcattg tttgtggcgt ttctcctgag agggaaactc   1020
atggaaacct attgttcgca gaaacacaca aggctagact acattggaga tagtaaaaat    1080
gtcctcaatg acgtgcagca tggaagggaa gacgaagacg cctttttac cctctaacaa     1140 cgcagtagca tgttag                                                   1156

<210> SEQ ID NO 8
<211> LENGTH: 2331
<212> TYPE: DNA
```

<213> ORGANISM: Mouse

<400> SEQUENCE: 8

| | | | | | |
|---|---|---|---|---|---|
| aggaaatgga | gaaagcagct | cagagaaagg | gaggacggag | ataagggaag | gcatggcaca | 60 |
| caacagagat | ggatggacag | tctgaggctg | agagagggct | agtgatttct | cggacacttg | 120 |
| ggcagtagaa | cccataccac | cctgttctct | gggatccgat | ggccttggag | aggggggctgc | 180 |
| agggcccgag | gacaccaact | cttcccagag | cgctggcatg | gagccagact | gaaattacca | 240 |
| tgtgtccaaa | ttaaaattgc | gtacttcaag | gattatttga | aggactattc | ttagacccett | 300 |
| ttaagaagat | tttttaaaaa | aacagttact | ggctgcagac | acggaaatgc | tctgactgct | 360 |
| gtagagccag | tgggccctt | aggggagctc | cagccctgtg | gaagccagac | aaccaacttg | 420 |
| aagccatttc | caaattgtgg | gtggtgatcc | atttcaagtt | atgaaatgaa | tttgatgatt | 480 |
| caaggccatc | gtttattaaa | actaattacc | tcgtgccgaa | tcggcacga | ggggcttctc | 540 |
| atcctctggc | tggtgacgga | gctctggtgg | ctttatctga | caccagctgc | ctcagaggat | 600 |
| acaataatag | ggttttttggg | ccagccggtg | actttgcctt | gtcattacct | ctcgtggtcc | 660 |
| cagagccgca | acagtatgtg | ctggggcaaa | ggttcatgtc | ccaattccaa | gtgcaatgca | 720 |
| gagcttctcc | gtacagatgg | aacaagaatc | atctccagga | agtcaacaaa | atatacactt | 780 |
| ttggggaagg | tccagtttgg | tgaagtgtcc | ttgaccatct | caaacaccaa | tcgaggtgac | 840 |
| agtggggtgt | actgctgccg | tatagaggtg | cctggctggt | tcaatgatgt | caagaagaat | 900 |
| gtgcgcttgg | agctgaggag | agccacaaca | accaaaaaac | caacaacaac | cacccggcca | 960 |
| accaccaccc | cttatgtgac | caccaccacc | ccagagctgc | ttccaacaac | agtcatgacc | 1020 |
| acatctgttc | tcccaaccac | cacaccaccc | cagacactag | ccaccactgc | cttcagtaca | 1080 |
| gcagtgacca | cgtgcccctc | aacaacacct | ggctccttct | cacaagaaac | cacaaaaggg | 1140 |
| tccgccttca | ctacagaatc | agaaactctg | cctgcatcca | atcactctca | aagaagcatg | 1200 |
| atgaccatat | ctacagacat | agccgtactc | aggcccacag | gctctaaccc | tgggattctc | 1260 |
| ccatccactt | cacagctgac | gacacagaaa | acaacattaa | caacaagtga | gtctttgcag | 1320 |
| aagacaacta | aatcacatca | gatcaacagc | agacagacca | tcttgatcat | tgcctgctgt | 1380 |
| gtgggatttg | tgctaatggt | gttattgttt | ctggcgtttc | tccttcgagg | gaaagtcaca | 1440 |
| ggagccaact | gtttgcagag | acacaagagg | ccagacaaca | ctgaagatag | tgacagcgtc | 1500 |
| ctcaatgaca | tgtcacacgg | gagggatgat | gaagacggga | tcttcactct | ctgactcacc | 1560 |
| atctttattt | aggattaagg | atagggaatg | gcacttgaat | tgtcaaaata | agtttgggga | 1620 |
| cattgtaatt | tccgtttaaa | gtctcactct | gtttactgat | gctgtgggtc | ctgtctggtt | 1680 |
| gtatcttccc | acatgaaggt | gttttagaga | cacatcttcc | ctgcctcgtg | ccttagtcct | 1740 |
| cttcgttgtt | ttgtggctag | gtgactttc | acactgggct | tgaacactgt | cagtgatggt | 1800 |
| gaaatccttg | ccacagcttt | gggagtctct | tgcagtctcc | cagcagtaga | gggagttaga | 1860 |
| aatatccaga | ggggaaaaaa | aatctctctt | ttcagacagt | atctgcttta | ttggtggtag | 1920 |
| ctgaatttca | tttatacaga | gctccttttaa | cctgtctgtc | ttcttcttgg | tatctaagct | 1980 |
| gccttttgtt | tttgttttttg | tttttgtttt | tatgatatta | acttcttttc | acattcaagt | 2040 |
| ttctttaaag | ttgactatag | tgccttctga | actcttgcag | agagtttgga | ttttggaagc | 2100 |
| tgccaggtac | ctatcacagc | agggqgtgcca | gtgacaagga | tggtgtacaa | atgaaacact | 2160 |
| gaagctatcc | aaataaattc | ctctaagtgt | aattcatttt | actgcagcac | aggaagaaca | 2220 |
| aatttgtctt | acaactttaa | taattagtac | cattatgaac | cctaggagag | aaataagagc | 2280 | aaatacctgt tgaataaatg aatgtaagaa aaaaaaaaaa aaaaaaaaaa a                2331

<210> SEQ ID NO 9
<211> LENGTH: 298
<212> TYPE: PRT
<213> ORGANISM: Mouse

<400> SEQUENCE: 9

Met Ser Lys Gly Leu Leu Leu Trp Leu Val Met Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Gln Lys
                245                 250                 255

Thr Arg Lys Val Thr Gly Ala Asn Cys Leu Gln Arg His Lys Arg Pro
            260                 265                 270

Asp Asn Thr Glu Asp Ser Asp Ser Val Leu Asn Asp Met Ser His Gly
        275                 280                 285

Arg Asp Asp Glu Asp Gly Ile Phe Thr Leu
    290                 295

<210> SEQ ID NO 10
<211> LENGTH: 304
<212> TYPE: PRT
<213> ORGANISM: Mouse

<400> SEQUENCE: 10

Met Ser Lys Gly Leu Leu Leu Trp Leu Val Met Glu Leu Trp Trp
1               5                   10                  15

```
Leu Tyr Leu Thr Pro Ala Ala Ser Glu Asp Thr Ile Ile Gly Phe Leu
             20                  25                  30

Gly Gln Pro Val Thr Leu Pro Cys His Tyr Leu Ser Trp Ser Gln Ser
         35                  40                  45

Arg Asn Ser Met Cys Trp Gly Lys Gly Ser Cys Pro Asn Ser Lys Cys
 50                  55                  60

Asn Ala Glu Leu Leu Arg Thr Asp Gly Thr Arg Ile Ile Ser Arg Lys
 65                  70                  75                  80

Ser Thr Lys Tyr Thr Leu Leu Gly Lys Val Gln Phe Gly Glu Val Ser
                 85                  90                  95

Leu Thr Ile Ser Asn Thr Asn Arg Gly Asp Ser Gly Val Tyr Cys Cys
                100                 105                 110

Arg Ile Glu Val Pro Gly Trp Phe Asn Asp Val Lys Lys Asn Val Arg
            115                 120                 125

Leu Glu Leu Arg Arg Ala Thr Thr Thr Lys Lys Pro Thr Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Ile Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Asn Gln Gln Gln Thr Asp His Leu Asp His Cys Leu Leu Cys Gly
            260                 265                 270

Ile Cys Ala Asn Gly Val Ile Val Ser Gly Val Ser Pro Ser Arg Glu
        275                 280                 285

Ser His Arg Ser Gln Leu Phe Ala Glu Thr Gln Glu Ala Arg Gln His
    290                 295                 300

<210> SEQ ID NO 11
<211> LENGTH: 322
<212> TYPE: PRT
<213> ORGANISM: Homo sapiens

<400> SEQUENCE: 11

Met Ser Lys Glu Pro Leu Ile Leu Trp Leu Met Ile Glu Phe Trp Trp
 1               5                  10                  15

Leu Tyr Leu Thr Pro Val Thr Ser Glu Thr Val Thr Glu Val Leu
             20                  25                  30

Gly His Arg Val Thr Leu Pro Cys Leu Tyr Ser Ser Trp Ser His Asn
         35                  40                  45

Ser Asn Ser Met Cys Trp Gly Lys Asp Gln Cys Pro Tyr Ser Gly Cys
 50                  55                  60

Lys Glu Ala Leu Ile Arg Thr Asp Gly Met Arg Val Thr Ser Arg Lys
 65                  70                  75                  80

Ser Ala Lys Tyr Arg Leu Gln Gly Thr Ile Pro Arg Gly Asp Val Ser
                 85                  90                  95
```

```
Leu Thr Ile Leu Asn Pro Ser Glu Ser Asp Ser Gly Val Tyr Cys Cys
            100                 105                 110

Arg Ile Glu Val Pro Gly Trp Phe Asn Asp Val Lys Ile Asn Val Arg
            115                 120                 125

Leu Asn Leu Gln Arg Ala Ser Thr Thr Thr His Arg Thr Ala Thr Thr
            130                 135                 140

Thr Thr Arg Arg Thr Thr Thr Ser Pro Thr Thr Thr Arg Gln Met
145                 150                 155                 160

Thr Thr Thr Pro Ala Ala Leu Pro Thr Thr Val Val Thr Thr Pro Asp
                165                 170                 175

Leu Thr Thr Gly Thr Pro Leu Gln Met Thr Thr Ile Ala Val Phe Thr
                180                 185                 190

Thr Ala Asn Thr Cys Leu Ser Leu Thr Pro Ser Thr Leu Pro Glu Glu
                195                 200                 205

Ala Thr Gly Leu Leu Thr Pro Glu Pro Ser Lys Glu Gly Pro Ile Leu
                210                 215                 220

Thr Ala Glu Ser Glu Thr Val Leu Pro Ser Asp Ser Trp Ser Ser Ala
225                 230                 235                 240

Glu Ser Thr Ser Ala Asp Thr Val Leu Leu Thr Ser Lys Glu Ser Lys
                245                 250                 255

Val Trp Asp Leu Pro Ser Thr Ser His Val Ser Met Trp Lys Thr Ser
                260                 265                 270

Asp Ser Val Ser Ser Pro Gln Pro Gly Gly Lys Leu Met Glu Thr Tyr
                275                 280                 285

Cys Ser Gln Lys His Thr Arg Leu Asp Tyr Ile Gly Asp Ser Lys Asn
                290                 295                 300

Val Leu Asn Asp Val Gln His Gly Arg Glu Asp Glu Asp Gly Leu Phe
305                 310                 315                 320

Thr Leu

<210> SEQ ID NO 12
<211> LENGTH: 362
<212> TYPE: PRT
<213> ORGANISM: Mouse

<400> SEQUENCE: 12

Met Asn Leu Met Ile Gln Gly His Arg Leu Leu Lys Leu Ile Thr Ser
  1               5                  10                  15

Cys Arg Ile Arg His Glu Gly Leu Leu Ile Leu Trp Leu Val Thr Glu
                 20                  25                  30

Leu Trp Trp Leu Tyr Leu Thr Pro Ala Ala Ser Glu Asp Thr Ile Ile
             35                  40                  45

Gly Phe Leu Gly Gln Pro Val Thr Leu Pro Cys His Tyr Leu Ser Trp
         50                  55                  60

Ser Gln Ser Arg Asn Ser Met Cys Trp Gly Lys Gly Ser Cys Pro Asn
65                  70                  75                  80

Ser Lys Cys Asn Ala Glu Leu Leu Arg Thr Asp Gly Thr Arg Ile Ile
                 85                  90                  95

Ser Arg Lys Ser Thr Lys Tyr Thr Leu Leu Gly Lys Val Gln Phe Gly
            100                 105                 110

Glu Val Ser Leu Thr Ile Ser Asn Thr Asn Arg Gly Asp Ser Gly Val
            115                 120                 125

Tyr Cys Cys Arg Ile Glu Val Pro Gly Trp Phe Asn Asp Val Lys Lys
            130                 135                 140
```

```
Asn Val Arg Leu Glu Leu Arg Arg Ala Thr Thr Thr Lys Lys Pro Thr
145                 150                 155                 160

Thr Thr Thr Arg Pro Thr Thr Pro Tyr Val Thr Thr Thr Pro
            165             170             175

Glu Leu Leu Pro Thr Thr Val Met Thr Thr Ser Val Leu Pro Thr Thr
            180             185             190

Thr Pro Pro Gln Thr Leu Ala Thr Thr Ala Phe Ser Thr Ala Val Thr
            195             200             205

Thr Cys Pro Ser Thr Thr Pro Gly Ser Phe Ser Gln Glu Thr Thr Lys
    210             215             220

Gly Ser Ala Phe Thr Thr Glu Ser Glu Thr Leu Pro Ala Ser Asn His
225             230             235             240

Ser Gln Arg Ser Met Met Thr Ile Ser Thr Asp Ile Ala Val Leu Arg
            245             250             255

Pro Thr Gly Ser Asn Pro Gly Ile Leu Pro Ser Thr Ser Gln Leu Thr
            260             265             270

Thr Gln Lys Thr Thr Leu Thr Thr Ser Glu Ser Leu Gln Lys Thr Thr
    275             280             285

Lys Ser His Gln Ile Asn Ser Arg Gln Thr Ile Leu Ile Ile Ala Cys
    290             295             300

Cys Val Gly Phe Val Leu Met Val Leu Leu Phe Leu Ala Phe Leu Leu
305             310             315             320

Arg Gly Lys Val Thr Gly Ala Asn Cys Leu Gln Arg His Lys Arg Pro
            325             330             335

Asp Asn Thr Glu Asp Ser Asp Ser Val Leu Asn Asp Met Ser His Gly
            340             345             350

Arg Asp Asp Glu Asp Gly Ile Phe Thr Leu
            355             360

<210> SEQ ID NO 13
<211> LENGTH: 305
<212> TYPE: PRT
<213> ORGANISM: Mouse

<400> SEQUENCE: 13

Met Asn Gln Ile Gln Val Phe Ile Ser Gly Leu Ile Leu Leu Leu Pro
1               5                   10                  15

Gly Ala Val Glu Ser His Thr Ala Val Gln Gly Leu Ala Gly His Pro
            20                  25                  30

Val Thr Leu Pro Cys Ile Tyr Ser Thr His Leu Gly Gly Ile Val Pro
        35                  40                  45

Met Cys Trp Gly Leu Gly Glu Cys Arg His Ser Tyr Cys Ile Arg Ser
    50                  55                  60

Leu Ile Trp Thr Asn Gly Tyr Thr Val Thr His Gln Arg Asn Ser Arg
65              70                  75                  80

Tyr Gln Leu Lys Gly Asn Ile Ser Glu Gly Asn Val Ser Leu Thr Ile
            85                  90                  95

Glu Asn Thr Val Val Gly Asp Gly Gly Pro Tyr Cys Cys Val Val Glu
            100                 105                 110

Ile Pro Gly Ala Phe His Phe Val Asp Tyr Met Leu Glu Val Lys Pro
            115                 120                 125

Glu Ile Ser Thr Ser Pro Pro Thr Arg Pro Thr Ala Thr Gly Arg Pro
            130                 135                 140

Thr Thr Ile Ser Thr Arg Ser Thr His Val Pro Thr Ser Thr Arg Val
```

```
                145                 150                 155                 160
Ser Thr Ser Thr Ser Pro Thr Pro Ala His Thr Glu Thr Tyr Lys Pro
                    165                 170                 175

Glu Ala Thr Thr Phe Tyr Pro Asp Gln Thr Thr Ala Glu Val Thr Glu
                180                 185                 190

Thr Leu Pro Asp Thr Pro Ala Asp Trp His Asn Thr Val Thr Ser Ser
                195                 200                 205

Asp Asp Pro Trp Asp Asp Asn Thr Glu Val Ile Pro Pro Gln Lys Pro
    210                 215                 220

Gln Lys Asn Leu Asn Lys Gly Phe Tyr Val Gly Ile Ser Ile Ala Ala
225                 230                 235                 240

Leu Leu Ile Leu Met Leu Leu Ser Thr Met Val Ile Thr Arg Tyr Val
                245                 250                 255

Val Met Lys Arg Lys Ser Glu Ser Leu Ser Phe Val Ala Phe Pro Ile
                260                 265                 270

Ser Lys Ile Gly Ala Ser Pro Lys Lys Val Val Glu Arg Thr Arg Cys
                275                 280                 285

Glu Asp Gln Val Tyr Ile Ile Glu Asp Thr Pro Tyr Pro Glu Glu Glu
    290                 295                 300

Ser
305

<210> SEQ ID NO 14
<211> LENGTH: 9
<212> TYPE: PRT
<213> ORGANISM: Mus musculus

<400> SEQUENCE: 14

Arg Thr Arg Cys Glu Asp Gln Val Tyr
 1                5

<210> SEQ ID NO 15
<211> LENGTH: 31
<212> TYPE: DNA
<213> ORGANISM: Artificial Sequence
<220> FEATURE:
<223> OTHER INFORMATION: TIM-4 Primer 1

<400> SEQUENCE: 15
agtcagatct gggttttttgg gccagccggt g                                    31

<210> SEQ ID NO 16
<211> LENGTH: 29
<212> TYPE: DNA
<213> ORGANISM: Artificial Sequence
<220> FEATURE:
<223> OTHER INFORMATION: TIM-4 Primer 2

<400> SEQUENCE: 16
agtcctgcag tcagagagtg aagatcccg                                        29

<210> SEQ ID NO 17
<211> LENGTH: 31
<212> TYPE: DNA
<213> ORGANISM: Artificial Sequence
<220> FEATURE:
<223> OTHER INFORMATION: TIM-1 Primer 1

<400> SEQUENCE: 17
agtcagatct atgaatcaga ttcaagtctt c                                     31
```

```
<210> SEQ ID NO 18
<211> LENGTH: 29
<212> TYPE: DNA
<213> ORGANISM: Artificial Sequence
<220> FEATURE:
<223> OTHER INFORMATION: TIM-1 Primer 2

<400> SEQUENCE: 18
agtcctgcag aggtctatct tcaacaatg                                    29

<210> SEQ ID NO 19
<211> LENGTH: 20
<212> TYPE: DNA
<213> ORGANISM: Artificial Sequence
<220> FEATURE:
<223> OTHER INFORMATION: TIM-4 Primer 3

<400> SEQUENCE: 19
cacctggctc cttctcacaa                                              20

<210> SEQ ID NO 20
<211> LENGTH: 21
<212> TYPE: DNA
<213> ORGANISM: Artificial Sequence
<220> FEATURE:
<223> OTHER INFORMATION: TIM-4 Primer 4

<400> SEQUENCE: 20
tgattggatg caggcagagt t                                            21

<210> SEQ ID NO 21
<211> LENGTH: 29
<212> TYPE: DNA
<213> ORGANISM: Artificial Sequence
<220> FEATURE:
<223> OTHER INFORMATION: TIM-4 Probe

<400> SEQUENCE: 21
aaaagggtcc gccatcacta cagaatcag                                    29

<210> SEQ ID NO 22
<211> LENGTH: 13
<212> TYPE: PRT
<213> ORGANISM: Artificial Sequence
<220> FEATURE:
<223> OTHER INFORMATION: PLP 139-151 peptide

<400> SEQUENCE: 22

His Ser Leu Gly Lys Trp Leu Gly His Pro Asp Lys Phe
 1               5                  10
```

METHODS OF MODULATING IMMUNE RESPONSES BY MODULATING TIM-1, TIM-2 AND TIM-4 FUNCTION

CROSS-REFERENCE TO RELATED APPLICATIONS

This application claims the benefit of the filing date of U.S. Application No. 60/552,523, filed Mar. 12, 2004, entitled "METHODS OF MODULATING IMMUNE RESPONSES BY MODULATING TIM-1 AND TIM-2 FUNCTION", and of U.S. Application No. 60/622,559 filed Oct. 27, 2004, entitled "METHODS OF MODULATING IMMUNE RESPONSES BY MODULATING TIM-1 AND TIM-4 FUNCTION." The entire teachings of the referenced applications are incorporated by reference herein.

STATEMENT REGARDING FEDERALLY-SPONSORED RESEARCH OR DEVELOPMENT

The invention described herein was supported, in whole or in part, by the National Institute of Health Grant Nos. 1RO1NSO45937-01, 2R01NS35685-06, 2R37NS30843-11, 1R01AI44880-03, 2P01AI39671-07, 1PO1NS38037-04 and 1F31GM20927-01. The United States government has certain rights in the invention.

BACKGROUND OF THE INVENTION

Excessive immune responses to external or internal factors may lead to disease, which may be characterized as Th1- or Th2-mediated diseases. Asthma, allergic rhinitis (hay fever), atopic dermatitis (eczema) and food allergies, examples of Th2-mediated diseases, are exceedingly prevalent, affecting 20-40% of the general population and constituting a major public health problem. The economic costs for these disorders are enormous. For asthma alone, the estimated health care costs in 1996 were 14 billion. In addition, the prevalence of all of the atopic diseases has increased dramatically in industrialized countries over the past two decades for reasons that are not yet clear. The prevalence of asthma in industrialized countries, for which the numbers are the most accurate, has doubled since 1982, and is projected to double again in prevalence by the year 2020.

Rheumatoid Arthritis (RA), a Th1 disorder, is a common human autoimmune disease with a prevalence of about 1% among Caucasians (Harris, B. J. et al., 1997, In Textbook of Rheumatology 898-932), currently affecting 2.5 million Americans. RA is characterized by chronic inflammation of the synovial joints and infiltration by activated T cells, macrophages and plasma cells, leading to a progressive destruction of the articular cartilage. It is the most severe form of joint disease. Multiple Sclerosis (MS), another Th1 disorder, is the most common central nervous system (CNS) demyelinating disease, affecting 350,000 (0.1%) individuals in North America and 1.1 million worldwide. In general, MS is considered to be an autoimmune disease mediated in part by proinflammatory CD4 T (Th1) cells that recognize specific myelin polypeptides in association with MHC class II molecules expressed on antigen (Ag) presenting cells (APC). Another example of a Th1 mediated disorder, human type I or insulin-dependent diabetes mellitus (IDDM), is characterized by autoimmune destruction of the beta cells in the pancreatic islets of Langerhans. The depletion of beta cells results in an inability to regulate levels of glucose in the blood. In humans a long presymptomatic period precedes the onset of diabetes. During this period there is a gradual loss of pancreatic beta cell function. The development of disease is implicated by the presence of autoantibodies against insulin, glutamic acid decarboxylase, and the tyrosine phosphatase IA2 (IA2).

T helper (Th) subsets are distinguished by their ability to produce distinct cytokine patterns and promote specific immune responses. Th1 cells produce IFNγ and promote cell-mediated immunity directed towards intracellular pathogens. In contrast, Th2 cells produce the cytokines IL-4, IL-5, and IL-13, activate mast cells and eosinophils and direct B cells against extracellular pathogens.

The specific cytokines produced by polarized Th cells are the primary effectors that promote differentiation of precursor Th cells, but these cells also cross-regulate the other subset's functional activity. For example IL-4 is reported to be a potent factor in promoting the differentiation of Thp cells to Th2 effectors. In addition, IL-4 antagonizes production of IFNγ. IL-10, another cytokine produced by Th2 cells, has also been described to inhibit Th1 development and IFNγ-induced macrophage function. Conversely, the IFNγ produced by Th1 cells amplifies Th1 development and inhibits the expansion of Th2 cells. The ability of these cytokines to promote development of specific Th cell subsets, while simultaneously inhibiting the alternate developmental fate, results in a progressively polarized response.

Accordingly, a need exists for novel therapies which promote or inhibit the development of Th1 or Th2 responses. Such novel therapies my be used to treat autoimmune and allergic diseases, to enhance immune tolerance of transplanted tissues or to decrease immune tolerance in individuals afflicted with cancer.

SUMMARY OF THE INVENTION

The present invention broadly relates to reagents, compositions and methods for modulating the activation of Th1 and Th2 cells and for modulating immune responses. The present invention is based, in part, on the unexpected discovery described herein that tim-1 and tim-4 form a polypeptide complex, and that the formation of this complex modulates T cell activation and immune responses. In some aspects, the invention provides a method of treating or preventing a Th1-mediated disorder in a subject in need of such treatment, the method comprising administering to the subject a therapeutically effective amount of an agent that reduces tim-1, tim-2, or tim-4 expression or activity. In some embodiments, the subject is afflicted with an autoimmune disease. A related aspect of the invention provides methods for inducing Th1 responses in subjects in need thereof, such as in a subject afflicted with a hyperplastic condition like cancer. Related aspects of the invention also provide methods for treating a subject afflicted with a Th2 disorder, such as with asthma or with an allergic disease, or for inducing a Th2 response in a subject in which such a response would be beneficial, such as a subject afflicted with an autoimmune disease.

The invention further provides methods of modulating immune/transplantation tolerance in a subject, comprising administering to the subject a therapeutically effective amount of an agent that modulates tim-1, tim-2 or tim-4 activity, thereby modulating immune tolerance. In some embodiments, the agent increases immune/transplantation tolerance by decreasing tim-1, tim-2 or tim-4 expression or activity. In other embodiments, the agent decreases immune tolerance by increasing tim-1, tim-2 or tim-4 expression or activity.

The invention further provides methods of enhancing or suppressing T-cell expansion in a subject in need thereof, the method comprising administering the subject an amount of a tim-4 polypeptide sufficient to enhance or suppress the T-cell expansion.

Another aspect of the invention provides a method of treating, preventing or reducing the likelihood of being afflicted with a hepatitis A infection in a subject in need thereof. In one embodiment, a hepatitis A infection is treated or prevented by administering to the subject a therapeutically effective amount of (i) a polypeptide comprising a tim-4 IgV domain, or (ii) a polypeptide comprising a sequence having a high degree of amino acid sequence identity, or amino acid sequence similarity, to the tim-4 IgV domain and/or the tim-4 mucin domain. A related aspect of the invention provides a method of preventing or reducing the likelihood of being afflicted with an atopic disease in a subject by administering to the subject a therapeutically effective amount of a polypeptide comprising a tim-4 IgV domain or an amount of a polypeptide comprising a sequence having a high degree of amino acid sequence identity, or amino acid sequence similarity, to the tim-4 IgV domain, to the tim-4 mucin domain, or to both. In other embodiments, the polypeptide comprises a tim-4 mucin domain or a domain that shares a high degree of amino acid sequence identity, or amino acid sequence similarity, to the tim-4 IgV mucin domain The invention also provides methods of identifying agents which modulate the formation of tim-1/tim-4 complexes, such as methods of identifying agents which promote or block complex formation, or which prevent the activation of tim-1 upon tim-4 binding. Another aspect of the invention provides methods of identifying agents which mimic the binding of tim-4 to tim-1, such as agents which may act as surrogates of tim-4 in promoting the activation of tim-1 and thus modulate immune responses.

The invention also provides novel tim-4 polypeptides, compositions comprising such polypeptides, and nucleic acids encoding them. A specific aspect provides soluble tim-4 polypeptides which are not membrane anchored. Preferred soluble peptides include those comprising the IgV and an N-terminal portion of the mucin domain, but which do not comprise the tim-4 transmembrane domain. In some embodiments, the soluble tim-4 polypeptides further comprise the intracellular domain of tim-4. Soluble tim-4 polypeptides may be used as agents which bind to tim-1 and regulate immune responses.

Figure 20:
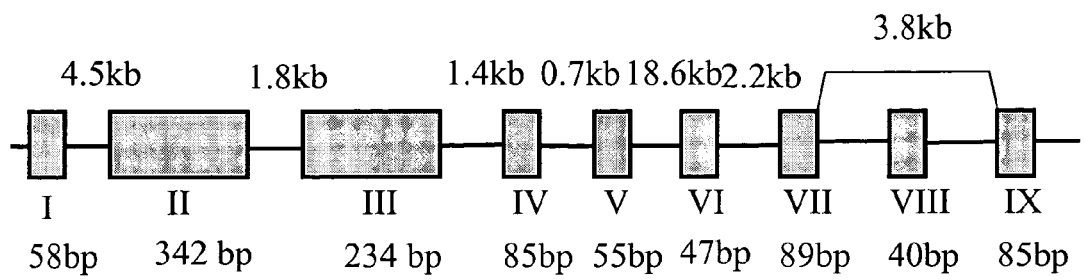
Figure 20:
Figure 20:
Figure 20:

FIG. 20 shows a diagram of alternative splicing of the mouse tim-4 locus to generate two soluble forms of tim-4.

DETAILED DESCRIPTION OF THE INVENTION

I. Overview

The invention generally provides novel methods and agents for modulating immune responses. The methods of the invention allow for the modulation of a subject's immune response towards a Th1 or a Th2 response. Th1 and Th2 responses are, in part, mutually exclusive, as naïve CD4⁺ T helper develop into either Th1 and Th2 effector cells, each secreting different cytokine profiles. Accordingly, the methods of the invention for inducing a Th1-mediated disorder may be useful to subjects who have a Th2-mediated disorder, while methods of inducing Th2 responses in a subject may be useful to subjects who have a Th2 disorder.

One aspect of the invention provides a method of modulating an immune response in a subject in need thereof, the method comprising administering to the subject a therapeutically effective amount of an agent which modulates binding between tim-1 and tim-4. In one embodiment of the methods described herein, the immune response is an increase in a Th1 immune response and the agent increases the activity or expression of tim-1, tim-2 or tim-4, such as an agent that increases the binding between the tim-1 and tim-4. In another embodiment of the methods described herein, the immune response is an increase in a Th2 immune response and the agent decreases the activity or expression of tim-1, tim-2 or tim-4, such as an agent that decreases the binding between the tim-1 and tim-4.

The invention further provides a method of treating or preventing or reducing the likelihood of being afflicted with a Th1-mediated disorder in a subject in need of such treatment, the method comprising administering to the subject a therapeutically effective amount of an agent that reduces expression or activity of tim-1, tim-2 or tim-4. Th1-mediated disorders include autoimmune diseases, such as multiple sclerosis, type-I diabetes, Hashinoto's thyroiditis, Crohn's disease, rheumatoid arthritis, systemic lupus erythematosus, gastritis, autoimmune hepatitis, hemolytic anemia, autoimmune hemophilia, autoimmune lymphoproliferative syndrome (ALPS), autoimmune uveoretinitis, glomerulonephritis, Guillain-Barré syndrome, psoriasis and myasthenia gravis. Th1-mediated disorders also include host versus graft disease (HVGD) and graft versus host disease.

The invention further provides a method of treating or preventing or reducing the likelihood of being afflicted with a Th2-mediated disorder in a subject in need of such treatment, the method comprising administering to the subject a therapeutically effective amount of an agent that increases expression or activity of tim-1, tim-2 or tim-4 or of both. In one embodiment, the Th2-mediated disorder is an atopic disorder. In another embodiment, the Th2 mediated disorder is asthma, an allergy, allergic rhinitis, gastrointestinal allergy, food allergy, eosinophilia, conjunctivitis or glomerulonephritis.

In another embodiment, the subject is afflicted with a hyperplastic condition which may include renal cancer, Kaposi's sarcoma, chronic leukemia, prostate cancer, breast cancer, sarcoma, pancreatic cancer, leukemia, ovarian carcinoma, rectal cancer, throat cancer, melanoma, colon cancer, bladder cancer, lymphoma, mastocytoma, lung cancer, mammary adenocarcinoma, pharyngeal squamous cell carcinoma, testicular cancer, gastrointestinal cancer, or stomach cancer, or a combinations thereof.

In another embodiment, the agent administered to the subject further comprises human serum albumin or an Fc domain of an immunoglobulin. In another embodiment, the agent increases phosphorylation of the intracellular domain of tim-1.

In one specific embodiment, the agent used in the methods described herein for modulating an immune response comprises a polypeptide comprising (i) amino acids 31-133 of SEQ ID NO: 3; (ii) amino acids 31-134 of SEQ ID NO: 4; (iii) an amino acid sequence that is at least 90% identical or similar to amino acids 31-133 of SEQ ID NO: 3; or (iv) an amino acid sequence that is at least 90% identical or similar to amino acids 31-134 of SEQ ID NO: 4; or (v) an amino acid sequence that is at least 90% identical to a tim-4 polypeptide comprising an amino acid sequence selected from the group consisting of SEQ ID NO: 3, SEQ ID NO: 4, SEQ ID NO: 9, SEQ ID NO: 10, SEQ ID NO:11 and SEQ ID NO: 12.

In another specific embodiment, the agent used in the methods described herein for modulating an immune response comprises a polypeptide comprising (i) amino acids 21-126 of SEQ ID NO: 1; (ii) amino acids 21-129 of SEQ ID NO: 2; (iii) an amino acid sequence that is at least 90% identical or similar to amino acids 21-126 of SEQ ID NO: 1; or (iv) an amino acid sequence that is at least 90% identical or similar to amino acids 21-129 of SEQ ID NO: 2. In another embodiment, the agent comprises an amino acid sequence that is at least 80%, 85% or 90% identical or similar to amino acids 130-237 of SEQ ID NO:1, 127-288 of SEQ ID NO:2, 134-318 of SEQ ID NO:3 or 136-281 of SEQ ID NO: 4.

In one embodiment of the methods described herein, the agent used in the methods described herein for modulating an immune response comprises an antibody, or antigen-binding fragment thereof, which binds to tim-1, tim-2 or to tim-4. In a specific embodiment, the agent is an antibody which binds to tim-4; the antibody or fragment may bind, for example, to the tim-4 IgV and/or mucin domain. In another embodiment, the agent is a bispecific antibody specific for tim-1 and tim-4, or for tim-2 and semaphorin-4A. Agents which decrease tim-1, tim-2 and tim-4 activity include antisense RNA reagents. In another embodiment, the agent comprises a polypeptide comprising an amino acid sequence that is at least 80%, 85% or 90% identical or similar to amino acids 130-237 of SEQ ID NO:1, 127-288 of SEQ ID NO:2, 134-318 of SEQ ID NO:3 or 136-281 of SEQ ID NO: 4. Agents also include peptidomimetics and small molecules i.e. nonpeptide compounds of less that 2 kDa.

The invention further provides methods of dug discovery, based in part on the unexpected finding that tim-1 and tim-4 form a physical complex, and that this interaction modulates immune responses. One aspect of the invention provides a method of identifying an agent that modulates the binding between a tim-1 polypeptide and a tim-4 polypeptide comprising: (a) contacting the tim-1 polypeptide and the tim-4 polypeptide in the presence of a test agent; and (b) determining the effect of the test agent on the binding of the tim-1 polypeptide and the tim-4 polypeptide; thereby identifying a agent that modulates the binding between a tim-1 polypeptide and a tim-4 polypeptide. The invention also provides a method of identifying an agent that modulates an immune response, the method comprising (a) contacting the tim-1 polypeptide and the tim-4 polypeptide in the presence of a test agent; and (b) determining the effect of the test agent on the binding of the tim-1 polypeptide and the tim-4 polypeptide; thereby identifying an agent that modulates an immune response. In one embodiment, step (b) comprises comparing formation of a tim-1/tim-4 complex in the presence of the test agent with an suitable control. In a specific embodiment, the suitable control comprises the formation of a complex between the first polypeptide and the second polypeptide in the absence of the test agent.

In another embodiment, the first polypeptide or the second polypeptide or both are expressed in a cell. In another embodiment, detecting the formation of the complex comprises detecting the expression of a reporter gene, wherein the expression of the reporter gene is dependent on the formation of the complex. In another embodiment, the first polypeptide or the second polypeptide or both are labeled with a fluorescent molecule. In another embodiment, the tim-4 polypeptide comprises (i) amino acids 31-133 of SEQ ID NO: 3; (ii) amino acids 31-134 of SEQ ID NO: 4; (iii) an amino acid sequence that is at least 90% identical or similar to amino acids 31-133 of SEQ ID NO: 3; or (iv) an amino acid sequence that is at least 90% identical or similar to amino acids 31-134 of SEQ ID NO: 4; or (v) an amino acid sequence that is at least 90% identical to a tim-4 polypeptide comprising an amino acid sequence selected from the group consisting of SEQ ID NO: 3, SEQ ID NO: 4, SEQ ID NO: 9, SEQ ID NO: 10, SEQ ID NO:11 and SEQ ID NO: 12. In yet another embodiment, the tim-1 polypeptide comprises (i) amino acids 21-126 of SEQ ID NO: 1; (ii) amino acids 21-129 of SEQ ID NO: 2; (iii) an amino acid sequence that is at least 90% identical or similar to amino acids 21-126 of SEQ ID NO: 1; or (iv) an amino acid sequence that is at least 90% identical or similar to amino acids 21-129 of SEQ ID NO: 2. In another embodiment, the tim-1 polypeptide comprises an amino acid sequence that is at least 80%, 85% or 90% identical or similar to amino acids 130-237 of SEQ ID NO:1 or 127-288 of SEQ ID NO:2.

The methods for identifying agents that modulate binding between tim-1 and tim-4 may be used to identify both agents that increase the binding between tim-1 and tim-4, and agents that decrease the binding between tim-1 and tim-4. The methods are not limited to identifying any particular type of agent. The agent may be, for example, a small compound, an antibody, a polypeptide, a nucleic acid, or a carbohydrate.

Additionally, one aspect of the invention provides a method of identifying an amino acid residue in tim-4 which contributes to the binding between tim-4 to tim-1, the method comprising (a) contacting (i) a polypeptide comprising a tim-4 IgV domain, wherein said tim-4 IgV domain has between one and ten amino acid substitutions relative to a tim-4 IgV domain as set forth in residues 31-133 of SEQ ID NO:3 or 31-134 of SEQ ID NO: 4; and (ii) a tim-1 polypeptide, wherein said tim-1 polypeptide is capable of binding to tim-4; (b) detecting formation of a complex between the polypeptide and the tim-1 polypeptide; and (c) comparing the formation of the complex to a suitable control, wherein an amino acid is identified as contributing to binding to tim-1 if the extent of complex formation differs from the suitable control.

A related aspect of the invention provides a method of identifying an amino acid residue in tim-4 which contributes to binding of tim-4 to tim-1, the method comprising (a) contacting (i) a polypeptide comprising a tim-4 mucin domain, wherein said tim-4 mucin domain has between one and ten amino acid substitutions relative to a tim-4 mucin domain as set forth in residues 134-318 of SEQ ID NO:3 or 136-281 of SEQ ID NO: 4; and (ii) a tim-1 polypeptide, wherein said tim-1 polypeptide is capable of binding to tim-4; (b) detecting formation of a complex between the polypeptide and the tim-1 polypeptide; and (c) comparing the formation of the complex to a suitable control, wherein an amino acid is identified as contributing to binding to tim-1 if the extent of complex formation differs from the suitable control.

In one embodiment of the methods for identifying an amino acid residue in tim-4 which contributes to binding of tim-4 to tim-1, the suitable control comprises the formation of a complex between (i) the tim-1 polypeptide, and (ii) a control polypeptide comprising the amino acids 31-133 of SEQ ID NO:3 and/or 134-318 of SEQ ID NO:3. In another embodiment, the tim-1 polypeptide comprises (i) amino acids 21-126 of SEQ ID NO: 1; (ii) amino acids 21-129 of SEQ ID NO: 2; (iii) an amino acid sequence that is at least 90% identical or similar to amino acids 21-126 of SEQ ID NO: 1 or 130-237 of SEQ ID NO: 1; or (iv) an amino acid sequence that is at least 90% identical or similar to amino acids 21-129 of SEQ ID NO: 2 or 127-288 of SEQ ID NO:2.

Another aspect of the invention provides a method of determining if a test polypeptide binds to a tim-1 polypeptide, wherein the test polypeptide comprises an amino acid sequence that is at least 90% identical or similar to amino acids 31-133 of SEQ ID NO: 3, the method comprising (a) contacting the test polypeptide with a tim-1 polypeptide; and (b) detecting formation of a complex between the test polypeptide and the tim-1 polypeptide; wherein the test polypeptide is determined to bind to the tim-1 polypeptide if a complex is detected. In one exemplary embodiment, the tim-1 polypeptide comprises (i) amino acids 21-126 of SEQ ID NO: 1; (ii) amino acids 21-129 of SEQ ID NO: 2; (iii) an amino acid sequence that is at least 90% identical or similar to amino acids 21-126 of SEQ ID NO: 1 or 130-237 of SEQ ID NO:1; or (iv) an amino acid sequence that is at least 90% identical or similar to amino acids 21-129 of SEQ ID NO: 2 or 127-288 of SEQ ID NO:2.

Another aspect of the invention provides a method of determining if a test polypeptide binds to a tim-4 polypeptide, wherein the test polypeptide comprises an amino acid sequence that is at least 90% identical or similar to amino acids 21-126 of SEQ ID NO: 1 or 130-237 of SEQ ID NO:1, the method comprising (a) contacting the test polypeptide with a tim-4 polypeptide; and (b) detecting formation of a complex between the test polypeptide and the tim-4 polypeptide; wherein the test polypeptide is determined to bind to the tim-4 polypeptide if a complex is detected. In one embodiment, the tim-4 polypeptide comprises (i) amino acids 31-133 of SEQ ID NO: 3; (ii) amino acids 31-134 of SEQ ID NO: 4; (iii) an amino acid sequence that is at least 90% identical or similar to amino acids 31-133 of SEQ ID NO: 3 or 134-318 of SEQ ID NO:3; or (iv) an amino acid sequence that is at least 90% identical or similar to amino acids 31-134 of SEQ ID NO: 4 or 136-281 of SEQ ID NO: 4; or (v) an amino acid sequence that is at least 90% identical to a tim-4 polypeptide comprising an amino acid sequence selected from the group consisting of SEQ ID NO: 3, SEQ ID NO: 4, SEQ ID NO: 9, SEQ ID NO: 10, SEQ ID NO:11 and SEQ ID NO: 12.

Another aspect of the invention provides a method of preventing or reducing the likelihood of being afflicted with an atopic disease in a subject, the method comprising administering to the subject a therapeutically effective amount of a polypeptide, said polypeptide comprising (i) amino acids 31-133 of SEQ ID NO: 3; (ii) amino acids 31-134 of SEQ ID NO: 4; (iii) an amino acid sequence that is at least 90% identical or similar to amino acids 31-133 of SEQ ID NO: 3; or (iv) an amino acid sequence that is at least 90% identical or similar to amino acids 31-134 of SEQ ID NO: 4 or 136-281 of SEQ ID NO: 4; or (v) an amino acid sequence that is at least 90% identical to a tim-4 polypeptide comprising an amino acid sequence selected from the group consisting of SEQ ID NO: 3, SEQ ID NO: 4, SEQ ID NO: 9, SEQ ID NO: 10, SEQ ID NO:11 and SEQ ID NO: 12.

Another aspect of the invention provides a method of treating or preventing or reducing the likelihood of being afflicted with a hepatitis A infection in a subject in need thereof, the method comprising administering to the subject a therapeutically effective amount of a polypeptide which comprises (i) amino acids 31-133 of SEQ ID NO: 3; (ii) amino acids 31-134 of SEQ ID NO: 4; (iii) an amino acid sequence that is at least 90% identical or similar to amino acids 31-133 of SEQ ID NO: 3 or 134-318 of SEQ ID NO:3; or (iv) an amino acid sequence that is at least 90% identical or similar to amino acids 31-134 of SEQ ID NO: 4 or 136-281 of SEQ ID NO: 4; or (v) an amino acid sequence that is at least 90% identical to a tim-4 polypeptide comprising an amino acid sequence selected from the group consisting of SEQ ID NO: 3, SEQ ID NO: 4, SEQ ID NO: 9, SEQ ID NO: 10, SEQ ID NO:11 and SEQ ID NO: 12. In one embodiment, the subject has not been afflicted with hepatitis A. In another embodiment, the subject has not been infected with the hepatitis A virus. In yet another embodiment, the subject is seronegative for anti-Hepatitis A antibodies. In another embodiment, the subject is a child. In another embodiment, the atopic disease is selected from the group consisting of asthma, rhinitis, eczema and hay fever.

Another aspect of the invention provides novel soluble tim-4 polypeptides. One aspect provides an isolated polypeptide comprising a tim-4 IgV domain, a tim-4 intracellular domain, and a truncated tim-4 mucin domain, wherein the polypeptide does not comprise a tim-4 transmembrane domain. Another aspect of the invention provides an isolated polypeptide comprising a tim-4 IgV domain and a truncated tim-4 mucin domain, wherein the polypeptide does not comprise a tim-4 transmembrane domain or a tim-4 intracellular domain. In a preferred embodiment, the soluble tim-4 polypeptide is a mammalian polypeptide, such as a human or a mouse polypeptide. In one specific embodiment, the soluble tim-4 polypeptide comprises amino acids 31-133 of SEQ ID NO: 3 or amino acids 31-134 of SEQ ID NO: 4. In another embodiment, the soluble tim-4 polypeptide comprises the sequence set forth in SEQ ID NO: 9, 10, 11 or 12, although in other embodiments the soluble tim-4 polypeptide does not comprise a signal sequence. In some embodiments, the soluble tim-4 polypeptides are fused to another polypeptide, such as polypeptides which increase its in vivo stability. In some embodiments, the fusion polypeptide comprises the Fc domain of an immunoglobulin or an albumin polypeptide. The invention further provides nucleic acids encoding the soluble tim-4 polypeptides described herein as well as compositions comprising tim-4 soluble polypeptides and a pharmaceutically acceptable carriers.

II. Definitions

For convenience, certain terms employed in the specification, examples, and appended claims, are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

The term "including" is used herein to mean, and is used interchangeably with, the phrase "including but not limited" to.

The term "or" is used herein to mean, and is used interchangeably with, the term "and/or," unless context clearly indicates otherwise.

The term "such as" is used herein to mean, and is used interchangeably, with the phrase "such as but not limited to".

The term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The term "preventing" is art-recognized, and when used in relation to a condition, such as a local recurrence (e.g., pain), a disease such as cancer, a syndrome complex such as heart failure or any other medical condition, is well understood in the art, and includes administering, prior to onset of the condition, a composition that reduces the frequency of, reduces the severity of, or delays the onset of symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the frequency of, reducing the severity of, or alternatively delaying, pain sensations experienced by subjects in a treated population versus an untreated control population.

The term "effective amount" as used herein is defined as an amount effective, at dosages and for periods of time necessary to achieve the desired result. The effective amount of a compound of the invention may vary according to factors such as the disease state, age, sex, and weight of the animal. Dosage regimens may be adjusted to provide the optimum therapeutic response. For example, several divided doses may be administered daily or the dose may be proportionally reduced as indicated by the exigencies of the therapeutic situation.

A "subject" as used herein refers to any vertebrate animal, preferably a mammal, and more preferably a human. Examples of subjects include humans, non-human primates, rodents, guinea pigs, rabbits, sheep, pigs, goats, cows, horses, dogs, cats, birds, and fish.

A "variant" of a polypeptide of interest, as used herein, refers to an amino acid sequence that is altered by one or more amino acids. The variant may have "conservative" changes, wherein a substituted amino acid has similar structural or chemical properties, (e.g., replacement of leucine with isoleucine). More rarely, a variant may have "nonconservative" changes (e.g., replacement of a glycine with a tryptophan).

Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

As used herein, a "Th1-associated disorder" is a disease or condition associated with aberrant, e.g., increased Th1 cell activity (e.g., increased Th1 cell responses) or number compared to a reference, e.g., a normal control. Examples of Th1-associated disorders include, e.g., autoimmune disorders (e.g., multiple sclerosis, rheumatoid arthritis, type I diabetes and Crohn's disease.

As used herein, a "Th2-associated disorder" is a disease or condition associated with aberrant, e.g., increased Th2 cell activity (e.g., increased Th2 cell responses) or number compared to a reference, e.g., a normal control. Examples of Th2 disorders include, e.g., asthma, allergy, and disorders associated with antibody components (e.g., rheumatoid arthritis).

The term "analog" as used herein includes, but is not limited, to amino acid sequences containing one or more amino acid substitutions, insertions, and/or deletions from a reference sequence. Amino acid substitutions may be of a conserved or non-conserved nature. Conserved amino acid substitutions involve replacing one or more amino acids of the polypeptides of the invention with amino acids of similar charge, size, and/or hydrophobicity characteristics. When only conserved substitutions are made the resulting analog should be functionally equivalent. Non-conserved substitutions involve replacing one or more amino acids of the amino acid sequence with one or more amino acids which possess dissimilar charge, size, and/or hydrophobicity characteristics. Amino acid insertions may consist of single amino acid residues or sequential amino acids ranging from 2 to 15 amino acids in length. Deletions may consist of the removal of one or more amino acids, or discrete portions from the amino acid sequence. The deleted amino acids may or may not be contiguous.

III. Tim Amino Acid and Nucleic Acid Sequences

Sequences of human and mouse tim polypeptides are described in SEQ ID NOs:1-14 and in PCT publication No. WO 03/002722, in U.S. Pat. Nos. 6,066,498, 6,204,371, 6,288,218, 6,084,083, 6,414,117, and 6,562,343, and in U.S. Patent Publication Nos. 2003/0069196 and 2003/0124114, the teachings of which are hereby incorporated by reference in their entirety. Tim-1, tim-2 and tim-4 nucleic acids and polypeptides of the invention are further understood to include nucleic acids and variants of the sequences described below. Variant nucleotide sequences include sequences that differ by one or more nucleotides such as by substitutions, additions or deletions, such as allelic variants; and will, therefore, include coding sequences that differ from the nucleotide sequence of the coding sequences of wild-type tim-1, tim-2 or tim-4 nucleotides e.g. due to the degeneracy of the genetic code. For example, nucleic acids encoding the IgV domain of tim-1 may be nucleic acids comprising a sequence that is at least 90%, 95%, 99% or 100% identical to the sequence of wild-type tim-1.

Sequences of mouse and human tim-1 polypeptides and nucleic acids are described in U.S. Patent Publication No. 2003/0124114, the contents of which are hereby incorporated by reference in their entirety. The human tim-1 polypeptide is also disclosed as Genbank Deposit No. NP_036338 (SEQ ID NO:1) and the nucleic acid sequence of the cDNA is disclosed as NM_012206 (SEQ ID NO:5). The amino acid and nucleic acid (cDNA) sequences of mouse tim-1 are disclosed as Genbank Deposit Nos. NP_599009 (SEQ ID NO:2) and NM_134248 (SEQ ID NO:6), respectively. Tim-1 has also been referred to in the scientific literature as HAVCR1, KIM1, TIM1, HAVCR, KIM-1 and TIMD1.

The amino acid and nucleic acid sequences of naturally occurring human allelic variants of tim-1 are disclosed in as SEQ ID NOs: 17-28 in U.S. Patent Publication No. 2003/0124114. These sequences are herein incorporated by reference. The IgV domain of human tim-1 spans residues 21-126 of SEQ ID NO:1, while the IgV domain of mouse tim-1 spans residues 21-129 of SEQ ID NO:2. The mucin domain of human tim-1 spans residues 130-237. The mucin domain of mouse tim-1 spans residues 127-288. Additional domains of human and mouse tim-1, such as the signal sequences, transmembrane domains and intracellular domains are described in McIntire et. al., Nat. Immunol. (2001); 2(12):1109-16, incorporated herein by reference.

Mouse TIM-2, a similar 305 amino acid membrane protein, has 64% identity to mouse TIM-1, 60% identity to rat KIM-1, and 32% identity to hHAVcr-1. Like TIM-1, TIM-2 has two extracellular N-linked glycosylation sites and a serine, threonine-rich mucin domain with many O-linked glycosylation sites. TIM-2 also has an intracellular tyrosine kinase phosphorylation motif, RTRCEDQVY (SEQ ID NO:14). The mouse TIM-2 polypeptide and nucleic acid sequences are described in U.S. Patent Publication No. 2003/0124114 as sequences 5 and 8, respectively. Additional mouse tim-2 sequences are described as Genbank Deposit Nos. NP_599010 and NM_134249. The IgV domain of mouse tim-2 stretches from about position 25 to 127 of SEQ ID NO:13.

Sequences of mouse and human tim-4 polypeptides and nucleic acids are described in U.S. Patent Publication No. 2003/0124114, the contents of which are hereby incorporated by reference in their entirety. The amino acid (SEQ ID NO:3) and nucleic acid (cDNA) (SEQ ID NO:7) sequences of human tim-4 are disclosed in U.S. Patent Publication No. 2003/0124114 as SEQ ID NOs: 33 and 34, respectively, while the amino acid and nucleic acid (cDNA) sequences of an allelic variant of tim-4 is also disclosed therein as SEQ ID NOs: 35 and 36, respectively. Two amino acid sequences of mouse tim-4 are disclosed as SEQ ID NO: 4 (NP_848874) and SEQ ID NO:12. The nucleic acid sequence corresponding to SEQ ID NO:12 is shown as SEQ ID NO:3 (NM_178759). The IgV domain of human tim-4 spans residues 31-133 of SEQ ID NO:3, while the IgV domain of mouse tim-4 spans residues 31-134 of SEQ ID NO: 4. The mucin domain of human tim-4 spans residues 134-318 of SEQ ID NO:3. The mucin domain of mouse tim-4 spans residues 134-281 of SEQ ID NO: 4.

The invention also provides novel tim-4 polypeptides and nucleic acids encoding them. In one aspect of the invention, the novel tim-4 polypeptides lack one or more exons, resulting in polypeptides lacking either N-terminal, C-terminal or internal sequences, or having a frameshifted reading frame as a result of the deleted exon(s). In one embodiment, the invention provides a soluble tim-4 polypeptide lacking the transmembrane domain. In another embodiment, the invention provides soluble tim-4 polypeptides lacking the transmembrane domain and lacking all or part of the mucin domain. In one embodiment, the soluble tim-4 polypeptides lacks 10-40 amino acids from the C-terminal end of the mucin domain, 15-30 amino acids, or more preferably between 18-25 amino acids. In one embodiment, the novel soluble tim-4 polypeptides comprise the amino acid sequence set forth in SEQ ID NOs: 9, 10 or 11. In another embodiment, the soluble human tim-4 polypeptide lacks residues 282-337 of SEQ ID NO:3. The invention also provides nucleic acids encoding said soluble tim-4 polypeptides.

Nucleic acids of the invention are further understood to include nucleic acids that comprise variants of the polypeptides described above. Variant nucleotide sequences include sequences that differ by one or more nucleotides such as by substitutions, additions or deletions, such as allelic variants; and will, therefore, include coding sequences that differ from the nucleotide sequence of the coding sequences of wild-type tim-1 or tim-4 nucleotides e.g. due to the degeneracy of the genetic code. For example, nucleic acids encoding the IgV domain of tim-1 may be nucleic acids comprising a sequence that is at least 80%, 85%, 90%, 95%, 96%, 97%, 98%, 99% or 100% identical or similar to the sequence of a wild-type tim-1 IgV domain. Sequences of human and mouse tim polypeptides are described in PCT publication No. WO 03/002722, in U.S. Pat. Nos. 6,066,498, 6,204,371, 6,288,218, 6,084,083, 6,414,117, and 6,562,343, and in U.S. Patent Publication Nos. 2003/0069196 and 2003/0124114, the teachings of which are hereby incorporated by reference in their entirety, including any nucleic acid or amino acid sequences for tim-1, tim-2, tim-3 and tim-4, variants and fragments thereof.

Isolated nucleic acids or their resulting polypeptide products which differ from the wild-type sequences due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the polypeptide. One skilled in the art will appreciate that these variations in one or more nucleotides of the nucleic acids encoding a particular polypeptide may exist among individuals of a given species due to natural allelic variation. Any and all such nucleotide variations and resulting amino acid polymorphisms are within the scope of the invention.

The invention provides methods using polypeptides or nucleic acids, wherein the nucleic acids or the polypeptides share a specified degree of sequence identity or similarity to another nucleic acid or polypeptide. To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, 90%, 95% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

In one embodiment, the percent identity between two amino acid sequences is determined using the Needleman and Wunsch (J. Mol. Biol. (48):444-453 (1970)) algorithm which has been incorporated into the GAP program in the GCG software package (available at http://www.gcg.com). In a specific embodiment, the following parameters are used in the GAP program: either a Blossom 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences is determined using the GAP program in the GCG software package (Devereux, J., et al., Nucleic Acids Res. 12(1):387 (1984)) (available at http://www.gcg.com). Exemplary parameters include using a NWSgapdna.CMP matrix and a gap weight of 40, 50, 60, 70, or 80 and a length weight of 1, 2, 3, 4, 5, or 6.

In another embodiment, the percent identity between two amino acid or nucleotide sequences is determined using the algorithm of E. Myers and W. Miller (CABIOS, 4:11-17 (1989)) which has been incorporated into the ALIGN program (version 2.0), using a PAM120 weight residue table, a gap length penalty of 12 and a gap penalty of 4.

A another embodiment for determining the best overall alignment between two nucleotide or amino acid sequences can be determined using the FASTDB computer program based on the algorithm of Brutlag et al. (Comp. App. Biosci., 6:237-245 (1990)). In a sequence alignment the query and subject sequences are either both nucleotide sequences or both amino acid sequences. The result of said global sequence alignment is presented in terms of percent identity. In one embodiment, amino acid sequence identity is performed using the FASTDB computer program based on the algorithm of Brutlag et al. (Comp. App. Biosci., 6:237-245 (1990)). In a specific embodiment, parameters employed to calculate percent identity and similarity of an amino acid alignment comprise: Matrix=PAM 150, k-tuple=2, Mismatch Penalty=1, Joining Penalty=20, Randomization Group Length=0, Cutoff Score=1, Gap Penalty=5 and Gap Size Penalty=0.05.

In some embodiments, the invention also encompasses polypeptides having a lower degree of identity, such as at least 60% identity, but having sufficient similarity so as to perform one or more of the same functions performed by the tim-1 or tim-4 polypeptides. Similarity is determined by conserved amino acid substitutions. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile, interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Additional guidance concerning which amino acid changes are likely to be phenotypically silent are found in Bowie et al., Science 247:1306-1310 (1990).

Some aspects of the invention provide polypeptides, or provide therapeutic methods for employing those polypeptides, wherein said polypeptides are defined, at least in part, to a reference sequence. For instance, some methods provided by the present invention provide a method of modulating an immune response in a subject in need thereof comprising administering to said subject an amino acid sequence that is at least 90% identical to amino acids 31-133 of SEQ ID NO: 3 (a reference sequence). Accordingly, such polypeptides may have a certain percentage of amino acid residues which are not identical to a reference sequence. In one preferred embodiment, the non-identical residues have similar chemical properties to the residues to which they are not identical. Groups that have similar properties include the following amino acids: E, D, N, Q; H, K, R; Y, F and W; I, L, V, M, C, A; and S, T, C, P, A. In another embodiment, the residues which are not identical are those which are not evolutionarily conserved between the reference sequence and an orthologous sequence in at least one evolutionarily related species, such as in species within the same order. In the case of a mammalian reference sequence, the amino acids that may be mutated in a preferred embodiment are those that are not conserved between the reference sequence and the orthologous sequence in another mammal species. For example, if a polypeptide used in a method of the present invention is said to comprise an amino acid sequence that is 90% identical to the IgV domain of human tim-4, then said polypeptide may have non-identical residues to those positions in which the IgV domain of tim-4 and that of mouse, rat, pig and/or chicken differ.

The invention further provides agents for the manufacture of medicaments to treat any of the disorders described herein. Any methods disclosed herein for treating or preventing a disorder by administering an agent to a subject may be applied to the use of the agent in the manufacture of a medicament to treat that disorder. For example, in one specific embodiment, a tim-1IgV-Fc fusion polypeptide may be used in the manufacture of a medicament for the treatment of Th1-mediated disorder.

In certain aspects, the present disclosure makes available isolated and/or purified forms of the soluble tim-4 polypeptides, which are isolated from, or are otherwise substantially free of, other polypeptides which might normally be associated with the polypeptide or a particular complex including the polypeptide. In certain embodiments, a soluble tim-4 polypeptide is a polypeptide that comprises an amino acid sequence that is at least 90%, 95%, 97%, 99% or 100% identical to the amino acid sequence of SEQ ID NO: 2, 4, 6 or 8. The amino acid identity between two polypeptides can be determined by first aligning the two polypeptide sequences using an alignment algorithm, such as one based on the PAM250 matrix.

In certain embodiments, a soluble tim-4 polypeptide is a polypeptide comprising a portion of an amino acid sequence that is at least 90%, 95%, 97%, 99% or 100% identical to any of SEQ ID NO: 9, 10, 11 or 12, and preferably wherein said portion is a functional portion, such as a portion that is sufficient to modulate Th1/Th2 activation or that is able to bind to a tim-1. In one embodiment, the portion comprises the IgV domain of tim-4. In some embodiments, the soluble tim-4 polypeptides contain conservative amino acid substitutions. In certain embodiments a soluble tim-4 polypeptide is purified or partially purified. In some embodiments, the soluble tim-4 polypeptides comprise the sequences set forth in SEQ ID NOs:9-12, with or without the signal sequences.

The invention further encompasses fusion polypeptides comprising a soluble tim-4 polypeptide and a heterologous polypeptide. In one embodiment, the soluble tim-4 polypeptide comprises the IgV domain but lacks at least part of the mucin domain, and lacks to transmembrane, and optionally the intracellular domain. In certain embodiments, fusion polypeptides comprising a soluble tim-4 polypeptide and an immunoglobulin element are provided. An exemplary immunoglobulin element is a constant region like the Fc domain of a human IgG1 heavy chain (Browning et al., J. Immunol., 154, pp. 33-46 (1995)). Soluble receptor-IgG fusion polypeptides are common immunological reagents and methods for their construction are known in the art (see e.g., U.S. Pat. Nos. 5,225,538, 5,766,883 and 5,876,969), all of which are incorporated by reference. In some embodiments, soluble peptides of the present invention are fused to Fc variants.

In a related embodiment, the modified polypeptides of the invention comprise tim-4 fusion polypeptides with an Fc region of an immunoglobulin. As is known, each immunoglobulin heavy chain constant region comprises four or five domains. The domains are named sequentially as follows: CH1-hinge-CH2-CH3(-CH4). The DNA sequences of the heavy chain domains have cross-homology among the immunoglobulin classes, e.g., the CH2 domain of IgG is homologous to the CH2 domain of IgA and IgD, and to the CH3 domain of IgM and IgE. As used herein, the term, "immunoglobulin Fc region" is understood to mean the carboxyl-terminal portion of an immunoglobulin chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more domains and an immunoglobulin hinge region. In a preferred embodiment the immunoglobulin Fc region comprises at least an immunoglobulin hinge region a CH2 domain and a CH3 domain, and preferably lacks the CH1 domain.

In one embodiment, the class of immunoglobulin from which the heavy chain constant region is derived is IgG (Igγ) (γ subclasses 1, 2, 3, or 4). Other classes of immunoglobulin, IgA (Igα), IgD (Igδ), IgE (Igε) and IgM (Igμ), may be used. The choice of appropriate immunoglobulin heavy chain constant regions is discussed in detail in U.S. Pat. Nos. 5,541,087, and 5,726,044. The choice of particular immunoglobulin heavy chain constant region sequences from certain immunoglobulin classes and subclasses to achieve a particular result is considered to be within the level of skill in the art. The portion of the DNA construct encoding the immunoglobulin Fc region preferably comprises at least a portion of a hinge domain, and preferably at least a portion of a $CH_3$ domain of Fc γ or the homologous domains in any of IgA, IgD, IgE, or IgM.

Furthermore, it is contemplated that substitution or deletion of amino acids within the immunoglobulin heavy chain constant regions may be useful in the practice of the invention. One example would be to introduce amino acid substitutions in the upper CH2 region to create a Fc variant with reduced affinity for Fc receptors (Cole et al. (1997) J. IMMUNOL. 159:3613). One of ordinary skill in the art can prepare such constructs using well known molecular biology techniques.

In a further embodiment, the fusion polypeptides comprise a soluble tim-4 polypeptide and a second heterologous polypeptide to increase the in vivo stability of the fusion polypeptide, or to modulate its biological activity or localization, or to facilitate purification of the fusion polypeptide. Other exemplary heterologous polypeptides that can be used to generate tim-4 soluble fusion polypeptides include, but not limited to, polyhistidine, Glu-Glu, glutathione S transferase (GST), thioredoxin, polypeptide A, polypeptide G, and an immunoglobulin heavy chain constant region (Fc), maltose binding polypeptide (MBP), which are particularly useful for isolation of the fusion polypeptides by affinity chromatography. For the purpose of affinity purification, relevant matrices for affinity chromatography, such as glutathione-, amylase-, and nickel- or cobalt-conjugated resins are used. Another fusion domain well known in the art is green fluorescent polypeptide (GFP). Fusion domains also include "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion polypeptides and thereby liberate the recombinant polypeptides therefrom. The liberated polypeptides can then be isolated from the fusion domain by subsequent chromatographic separation.

Preferably, stable plasma polypeptides, which typically have a half-life greater than 20 hours in the circulation, are used to construct fusions polypeptides with tim-4. Such plasma polypeptides include but are not limited to: immunoglobulins, serum albumin, lipopolypeptides, apolipopolypeptides and transferrin. Sequences that can target the soluble tim-4 molecules to a particular cell or tissue type may also be attached to the soluble tim-4 to create a specifically-localized soluble tim-4 fusion polypeptide.

In one preferred embodiment, the invention provides tim-4 fusions to albumin. As used herein, "albumin" refers collectively to albumin polypeptide or amino acid sequence, or an albumin fragment or variant, having one or more functional activities (e.g., biological activities) of albumin. In particular, "albumin" refers to human albumin or fragments thereof (see EP 201 239, EP 322 094 WO 97/24445, WO95/23857) especially the mature form of human albumin, or albumin from other vertebrates o In particular, the albumin fusion polypeptides of the invention may include naturally occurring polymorphic variants of human albumin and fragments of human albumin (See WO95/23857), for example those fragments disclosed in EP 322 094 (namely HA (Pn), where n is 369 to 419). The albumin may be derived from any vertebrate, especially any mammal, for example human, cow, sheep, or pig. Non-mammalian albumins include, but are not limited to, hen and salmon. The albumin portion of the albumin fusion polypeptide may be from a different animal than the tim-4 or tim-1 polypeptide.

In some embodiments, the albumin polypeptide portion of an albumin fusion polypeptide corresponds to a fragment of serum albumin. Fragments of serum albumin polypeptides include polypeptides having one or more residues deleted from the amino terminus or from the C-terminus. Generally speaking, an HA fragment or variant will be at least 100 amino acids long, preferably at least 150 amino acids long. The HA variant may consist of or alternatively comprise at least one whole domain of HA. Domains, of human albumin are described in U.S. Patent Publication No. 2004/0171123.

In certain embodiments, the invention includes nucleic acids encoding soluble tim-4 polypeptides In further embodiments, this invention also pertains to a host cell comprising soluble tim-4 polypeptides and related derivatives. The host cell may be any prokaryotic or eukaryotic cell. For example, a polypeptide of the present invention may be expressed in bacterial cells such as E. coli, insect cells (e.g., using a baculovirus expression system), yeast, or mammalian cells. In one embodiment, the soluble tim-4 polypeptide is made and secreted by a mammalian cell, and the soluble tim-4 polypeptide is purified from the culture medium. Other suitable host cells are known to those skilled in the art. Accordingly, some embodiments of the present invention further pertain to methods of producing the soluble tim-4 polypeptides.

It is also possible to modify the structure of the subject tim-4 polypeptides for such purposes as enhancing therapeutic or prophylactic efficacy, or stability (e.g., ex vivo shelf life and resistance to proteolytic degradation in vivo). Such modified polypeptides, when designed to retain at least one activity of the naturally-occurring form of the polypeptide, are considered functional equivalents of the tim-4 polypeptides described in more detail herein. Such modified polypeptides can be produced, for instance, by amino acid substitution, deletion, or addition.

For instance, it is reasonable to expect, for example, that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, 2nd ed., Ed. by L. Stryer, W.H. Freeman and Co., 1981). Whether a change in the amino acid sequence of a polypeptide results in a functional homolog can be readily determined by assessing the ability of the variant polypeptide to produce a response in cells in a fashion similar to the wild-type polypeptide. For instance, such variant forms of a tim-4 polypeptide can be assessed, e.g., for their ability to modulate the secretion of cytokines by Th1 or Th2 cells, or their ability to bind to a tim-1 polypeptide. Polypeptides in which more than one replacement has taken place can readily be tested in the same manner.

Some of the tim-1, tim-2 or tim-4 polypeptides provided by the invention, or used in the methods of the present invention, may further comprise post-translational modifications. Exemplary post-translational polypeptide modification include phosphorylation, acetylation, methylation, ADP-ribosylation, ubiquitination, glycosylation, carbonylation, sumoylation, biotinylation or addition of a polypeptide side chain or of a hydrophobic group. As a result, the modified soluble polypeptides may contain non-amino acid elements, such as lipids, poly- or mono-saccharide, and phosphates.

In one specific embodiment of the present invention, modified forms of the subject tim-1, tim-2 or tim-4 polypeptides, such as tim-4 soluble polypeptides, comprise linking the subject soluble polypeptides to nonpolypeptide polymers. In one specific embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337. PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: $X—O(CH_2CH_2O)_{n-1}CH_2CH_2OH$ (1), where n is 20 to 2300 and X is H or a terminal modification, e.g., a $C_{1-4}$ alkyl. In one embodiment, the PEG of the invention terminates on one end with hydroxy or methoxy, i.e., X is H or $CH_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-0473084 and U.S. Pat. No. 5,932,462. One form of PEGs includes two PEG side-chains (PEG2) linked via the primary amino groups of a lysine (Monfardini, C., et al., *Bioconjugate Chem.* 6 (1995) 62-69).

PEG conjugation to peptides or polypeptides generally involves the activation of PEG and coupling of the activated PEG-intermediates directly to target polypeptides/peptides or to a linker, which is subsequently activated and coupled to target polypeptides/peptides (see Abuchowski, A. et al, *J. Biol. Chem.*, 252, 3571 (1977) and *J. Biol. Chem.*, 252, 3582 (1977), Zalipsky, et al., and Harris et. al., in: Poly(ethylene glycol) Chemistry: Biotechnical and Biomedical Applications; (J. M. Harris ed.) Plenum Press: New York, 1992; Chap. 21 and 22).

One skilled in the art can select a suitable molecular mass for PEG, e.g., based on how the pegylated tim-4 or tim-1 polypeptide will be used therapeutically, the desired dosage, circulation time, resistance to proteolysis, immunogenicity, and other considerations. For a discussion of PEG and its use to enhance the properties of polypeptides, see N. V. Katre, Advanced Drug Delivery Reviews 10: 91-114 (1993).

In one embodiment of the invention, PEG molecules may be activated to react with amino groups on tim-4 or tim-1 polypeptides, such as with lysines (Bencham C. O. et al., Anal. Biochem., 131, 25 (1983); Veronese, F. M. et al., Appl. Biochem., 11, 141 (1985).; Zalipsky, S. et al., Polymeric Drugs and Drug Delivery Systems, adrs 9-110 ACS Symposium Series 469 (1999); Zalipsky, S. et al., Europ. Polym. J., 19, 1177-1183 (1983); Delgado, C. et al., Biotechnology and Applied Biochemistry, 12, 119-128 (1990)). In another embodiment, PEG molecules may be coupled to sulfhydryl groups on tim-4 or tim-1 (Sartore, L., et al., Appl. Biochem. Biotechnol., 27, 45 (1991); Morpurgo et al., Biocon. Chem., 7, 363-368 (1996); Goodson et al., Bio/Technology (1990) 8, 343; U.S. Pat. No. 5,766,897). U.S. Pat. Nos. 6,610,281 and 5,766,897 describes exemplary reactive PEG species that may be coupled to sulfhydryl groups. In some embodiments, the pegylated tim-4 or tim-1 polypeptides comprise a PEG molecule covalently attached to the alpha amino group of the N-terminal amino acid. Site specific N-terminal reductive amination is described in Pepinsky et al., (2001) JPET, 297, 1059, and U.S. Pat. No. 5,824,784. The use of a PEG-aldehyde for the reductive amination of a polypeptide utilizing other available nucleophilic amino groups is described in U.S. Pat. No. 4,002,531, in Wieder et al., (1979) J. Biol. Chem. 254,12579, and in Chamow et al., (1994) Bioconjugate Chem. 5, 133.

IV. Methods of Modulating Immune Responses

One aspect of the invention provides methods of modulating immune responses in a subject, such as but not limited to, modulating Th1 or Th2 responses, immune tolerance and transplantation tolerance. The term modulating as used herein refers to increasing or decreasing. In a preferred embodiment, the subject is a human. In another embodiment, the subject is a mammal, such as a mouse.

One specific aspect of the invention provides a method of treating or preventing or reducing the likelihood of being afflicted with a Th1-mediated disorder in a subject in need of such treatment, the method comprising administering to the subject a therapeutically effective amount of an agent that reduces expression or activity of tim-1, tim-2, tim-4 or both, or that reduces the binding of tim-1 to tim-4 or the binding of tim-2 to semaphorin-4A. The amino acid sequence of Semaphorin4A is described as Genbank Deposit No. NP_071762. Another aspect of the invention features a method of decreasing, inhibiting, suppressing, ameliorating, or delaying a Th1-mediated immune response, in a subject in need thereof, comprising administering to the subject a tim-1, tim-2 or a tim-4 antagonist, e.g., a tim-1, tim-2 or a tim-4 antagonist in an amount sufficient to decrease, inhibit, suppress, ameliorate, or delay said Th1-mediated immune response in the subject.

In contrast to a Th2-mediated disorder, a "Th1-mediated disorder" as used herein refers to a disease that is associated with the development of a Th1 immune response. A "Th1 immune response" as used herein refers to the induction of at least one Th1-cytokine or a Th1-antibody. In preferred embodiments more than one Th1-cytokine or Th1-antibody is induced. Thus a Th1-mediated disease is a disease associated with the induction of a Th1 response and refers to the partial or complete induction of at least one Th1-cytokine or Th1-antibody or an increase in the levels of at least one Th1-cytokine or Th1-antibody. These disorders are known in the art and include for instance, but are not limited to, autoimmune (especially organ-specific) disease, psoriasis, Th1 inflammatory disorders, infection with extracellular parasites (e.g., response to helminths), solid organ allograft rejection (e.g., acute kidney allograft rejection), symptoms associated with hepatitis B (HBV) infection (e.g., HBV acute phase or recovery phase), chronic hepatitis C(HCV) infection, insulin-dependent diabetes mellitus (IDDM), multiple sclerosis (MS), subacute lymphocytic thyroiditis ("silent thyroiditis"), Crohn's disease, primary biliary cirrhosis, primary sclerosing cholangitis, sarcoidosis, atherosclerosis, acute graft-versus-host disease (GvHD), glomerulonephritis, anti-glomerular basement membrane disease, Wegener's granulomatosis, inflammatory myopathies, Sjogren's syndrome, Behçet's syndrome, rheumatoid arthritis, Lyme arthritis, and unexplained recurrent abortion.

In some embodiments the Th1-mediated disorder is selected from the group consisting of atherosclerosis, infection with extracellular parasites, symptoms associated with hepatitis B (HBV) infection (e.g., HBV acute phase or recovery phase), chronic hepatitis C(HCV) infection, silent thyroiditis, primary biliary cirrhosis, primary sclerosing cholangitis, glomerulonephritis, anti-glomerular basement membrane disease, Wegener's granulomatosis, inflammatory myopathies, Sjogren's syndrome, Behcet's syndrome, rheumatoid arthritis, and unexplained recurrent abortion.

The methods described herein for decreasing Th1-mediated immune responses may be particularly beneficial to treat autoimmune diseases in a subject. In one embodiment, the methods of the present invention for reducing a Th1 response in a subject are directed at subjects afflicted with, or at high risk of developing an autoimmune disease. "Autoimmune disease" is a class of diseases in which a subject's own antibodies react with host tissue or in which immune effector T cells are autoreactive to endogenous self-peptides and cause destruction of tissue. Thus an immune response is mounted against a subject's own antigens, referred to as self-antigens. A "self-antigen" as used herein refers to an antigen of a normal host tissue. Normal host tissue does not include cancer cells. Thus an immune response mounted against a self-antigen, in the context of an autoimmune disease, is an undesirable immune response and contributes to destruction and damage of normal tissue, whereas an immune response mounted against a cancer antigen is a desirable immune response and contributes to destruction of the tumor or cancer.

Autoimmune diseases include but are not limited to rheumatoid arthritis, Crohn's disease, multiple sclerosis, systemic lupus erythematosus (SLE), autoimmune encephalomyelitis, myasthenia gravis (MG), Hashimoto's thyroiditis, Goodpasture's syndrome, pemphigus (e.g., pemphigus vulgaris), Grave's disease, autoimmune hemolytic anemia, autoimmune thrombocytopenic purpura, scleroderma with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, Sjogren's syndrome, insulin resistance, and autoimmune diabetes mellitus (type 1 diabetes mellitus; insulin-dependent diabetes mellitus). Recently autoimmune disease has been recognized also to encompass atherosclerosis and Alzheimer's disease. In one specific embodiment, the autoimmune disease is selected from the group consisting of multiple sclerosis, type-I diabetes, Hashinoto's thyroiditis, Crohn's disease, rheumatoid arthritis, systemic lupus erythematosus, gastritis, autoimmune hepatitis, hemolytic anemia, autoimmune hemophilia, autoimmune lymphoproliferative syndrome (ALPS), autoimmune uveoretinitis, glomerulonephritis, Guillain-Barré syndrome, psoriasis and myasthenia gravis. In another embodiment, the Th1-mediated disorder is host versus graft disease (HVGD). In a related embodiment, the subject is an organ or tissue transplant recipient.

Yet another aspect of the invention provides a method for increasing transplantation tolerance in a subject, comprising administering to the subject a therapeutically effective amount of an agent that decreases tim-1, tim-2 or tim-4 function. In one specific embodiment, the subject is a recipient of an allogenic transplant. The transplant can be any organ or tissue transplant, including but not limited to heart, kidney, liver, skin, pancreas, bone marrow, skin or cartilage. Transplantation tolerance, as used herein, refers to a lack of rejection of the donor organ by the recipient's immune system. Furthermore, the agents can be used for preventing or reducing the likelihood of being afflicted with rejection of tissue or cell transplants.

Another aspect of the invention provides a method of reducing immune tolerance and increasing Th1 activation in a subject in need thereof, the method comprising administering to the subject a therapeutically effective amount of an agent that increases the expression or activity of tim-1, tim-2 or tim-4 i.e. a tim-1, tim-2 or tim-4 agonist, or that increases the binding of tim-1 to tim-4 or binding of tim-2 to semaphorin4A. A reduction in immune tolerance may be beneficial in cancer immunotherapy. The immune system can develop tolerance against tumor antigens, thus allowing tumors to evade immune surveillance. In one aspect of the invention, an agent which increases tim-1, tim-2 or tim-4 activity, or that increases the binding of tim-1 to tim-4 or binding of tim-2 to semaphorin4A, is administered to a subject afflicted with a hyperplastic condition.

The terms "cancer" and "tumor" are used interchangeably, both terms referring to a hyperplastic condition. In one embodiments, the cancer is selected from the group consisting of Kaposi's sarcoma, chronic leukemia, prostate cancer, breast cancer, sarcoma, pancreatic cancer, leukemia, ovarian carcinoma, rectal cancer, throat cancer, melanoma, colon cancer, bladder cancer, lymphoma, mastocytoma, lung cancer, mammary adenocarcinoma, pharyngeal squamous cell carcinoma, and gastrointestinal or stomach cancer. In another embodiment, the cancer is selected for the group consisting of basal cell carcinoma, biliary tract cancer; bladder cancer; bone cancer; brain and CNS cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia; liver cancer; lung cancer (e.g., small cell and non-small cell); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; sarcoma; skin cancer; stomach cancer; testicular cancer; thyroid cancer; uterine cancer; cancer of the urinary system, as well as other carcinomas and sarcomas.

In yet another aspect, the invention features a method of decreasing, inhibiting, suppressing, ameliorating, or delaying a Th2-associated response (e.g., an allergic or an asthmatic response), in a subject in need thereof, the method comprising administering to a subject an agent that increases expression or activity of tim-1, tim-2, tim-4 i.e. administering a tim-1, tim-2 or a tim-4 agonist, or an agent that increases the binding of tim-4 to tim-1 or the binding of tim-2 to semaphorin4A.

A "Th2-mediated disorder" as used herein refers to a disease that is associated with the development of a Th2 immune response. A "Th2 immune response" as used herein refers to the induction of at least one Th2-cytokine or a Th2-antibody. In preferred embodiments more than one Th2-cytokine or Th2-antibody is induced. Thus a Th2-mediated disease is a disease associated with the induction of a Th2 response and refers to the partial or complete induction of at least one Th2-cytokine or Th2-antibody or an increase in the levels of at least one Th2-cytokine or Th2-antibody. These disorders are known in the art and include for instance, but are not limited to, atopic conditions, such as asthma and allergy, including allergic rhinitis, gastrointestinal allergies, including food allergies, eosinophilia, conjunctivitis, glomerulonephritis, certain pathogen susceptibilities such as helminthic (e.g., leishmaniasis) and certain viral infections, including human immunodeficiency virus (HIV), and certain bacterial infections, including tuberculosis and lepromatous leprosy. In a preferred embodiment, the Th2-associated response is asthma or an allergy.

Asthma, as defined herein, is reversible airflow limitation in an individual over a period of time. Asthma is characterized by the presence of cells such as eosinophils, mast cells, basophils, and $CD25^+$ T lymphocytes in the airway walls. There is a close interaction between these cells, because of the activity of cytokines which have a variety of communication and biological effector properties. Chemokines attract cells to the site of inflammation and cytokines activate them, resulting in inflammation and damage to the mucosa. With chronicity of the process, secondary changes occur, such as thickening of basement membranes and fibrosis. The disease is characterized by increased airway hyperresponsiveness to a variety of stimuli, and airway inflammation. A patient diagnosed as asthmatic will generally have multiple indications over time, including wheezing, asthmatic attacks, and a positive response to methacholine challenge, i.e., a PC20 on methacholine challenge of less than about 4 mg/ml. Guidelines for diagnosis may be found, for example, in the National Asthma Education Program Expert Panel Guidelines for Diagnosis and Management of Asthma, National Institutes of Health, 1991, Pub. No. 91-3042.

As used herein, "allergy" shall refer to acquired hypersensitivity to a substance (allergen). Allergic conditions include eczema, allergic rhinitis or coryza, hay fever, bronchial asthma, urticaria (hives) and food allergies, and other atopic conditions. A "subject having an allergy" is a subject that has or is at risk of developing an allergic reaction in response to an allergen. An "allergen" refers to a substance that can induce an allergic or asthmatic response in a susceptible subject. The list of allergens is enormous and can include pollens, insect venoms, animal dander, dust, fungal spores and drugs (e.g., penicillin).

Allergens of interest include antigens found in food, such as strawberries, peanuts, milk polypeptides, egg whites, etc. Other allergens of interest include various airborne antigens, such as grass pollens, animal danders, house mite feces, etc. Molecularly cloned allergens include *Dermatophagoides pteryonyssinus* (Der P1); Lol pl-V from rye grass pollen; a number of insect venoms, including venom from jumper ant *Myrmecia pilosula; Apis mellifera* bee venom phospholipase A2 (PLA$_2$ and antigen 5S; phospholipases from the yellow jacket *Vespula maculifrons* and white faced hornet *Dolichovespula maculata*; a large number of pollen polypeptides, including birch pollen, ragweed pollen, Parol (the major allergen of *Parietaria officinalis*) and the cross-reactive allergen Parjl (from *Parietaria judaica*), and other atmospheric pollens including *Olea europaea, Artemisia* sp., gramineae, etc. Other allergens of interest are those responsible for allergic dermatitis caused by blood sucking arthropods, e.g. Diptera, including mosquitos (*Anopheles* sp., *Aedes* sp., *Culiseta* sp., *Culex* sp.); flies (*Phlebotomus* sp., *Culicoides* sp.) particularly black flies, deer flies and biting midges; ticks (*Dermacenter* sp., *Ornithodoros* sp., *Otobius* sp.); fleas, e.g. the order *Siphonaptera*, including the genera *Xenopsylla, Pulex* and *Ctenocephalides felis*. The specific allergen may be a polysaccharide, fatty acid moiety, polypeptide, etc.

According to the present invention, agents which modulate tim-1, tim-2 or tim-4 activity, or modulate complex formation between tim-1 and tim-4, may be used in combination with other compositions and procedures for the modulation of an immune response or for treatment of a disorder or conditions. For example, a tumor may be treated conventionally with surgery, radiation or chemotherapy. Agents which increase tim-1 activity, such as a tim-4-IgG fusion polypeptide, may be subsequently administered to the patient to extend the dormancy of micrometastases and to stabilize any residual primary tumor.

In addition, the methods described herein may be combined with the methods described in U.S. Patent Application No. 60/508,319, hereby incorporated by reference in its entirety, to modulate immune responses. For example, a method for increasing a Th1 response in a subject may comprise administering to the subject (i) an agent which blocks binding of galectin-9 to tim-3, such as a tim-3Ig polypeptide, and (ii) an agent which increases tim-1 activity, such as a tim-4-Ig fusion. One skilled in the art will appreciate that many combinations of agents are possible. Preferred combinations of methods are those in which the activity of tim-3 and that of either tim-1/tim-4 is modulated in opposite directions, such as increasing tim-3 activity and decreasing tim-1/tim-4 activity, or vice versa. U.S. Patent Publication No. 2004/0005322 also describes tim-3 related agents and compositions that may be used in conjunction with the methods described herein.

The invention further provides methods of enhancing or suppressing T-cell expansion in a subject in need thereof, the method comprising administering the subject an amount of a tim-4 polypeptide sufficient to enhance or suppress the T-cell expansion. Such methods are derived, in part, on applicants unexpected finding that a tim-4:Ig fusion protein can suppress or enhance the proliferation of T-cells in a dosage dependent manner. An enhancement of T-cell response may be beneficial to subjects afflicted with a pathogen, including infectious agents such as viruses. A suppression of T-cell responses may be beneficial to subjects afflicted with a Th1 or a Th2 mediated disorder.

Appropriate dosages of tim-4 polypeptides, such as those of a tim-4:Ig fusion, may be extrapolated from in vitro or from in vivo data, such as that provided in Example 16. A person of ordinary skill in the art can perform simple titration experiments to determine what amount is required to treat the subject. For example, a sample of T-cells may be obtained from the subject and a dose response curve to the tim-4 agent may be generated to identify an optimal dosage to either enhance or suppress T-cell expansion in that subject. The dose of the composition of the invention will vary depending on the subject and upon the particular route of administration used. Based upon the composition, the dose can be delivered continuously, such as by continuous pump, or at periodic intervals, such as at one, two or more separate occasions. Desired time intervals of multiple doses of a particular composition can be determined without undue experimentation by one skilled in the art.

Another aspect of the invention provides a method of preventing, or of reducing the likelihood of becoming afflicted with, an atopic disease. Atopic diseases are complex genetic traits that develop as a result of environmentally induced immune responses in genetically predisposed individuals. Both atopic and non-atopic individuals are exposed to the same environmental factors, but genetic differences that distinguish atopic from non-atopic individuals result in atopic disease in some individuals, manifested by allergic inflammation in the respiratory tract, skin or gastrointestinal tract, as well as by elevated serum IgE, eosinophilia and the symptoms of wheezing, sneezing or hives. In addition, allergic inflammatory responses are characterized by the presence of Th2 lymphocytes producing high levels of IL-4, IL-5, IL-9 and IL-13, which enhance the growth, differentiation and/or recruitment of eosinophils, mast cells, basophils and B cells producing IgE.

One specific aspect of the invention provides a method of preventing or reducing the likelihood of being afflicted with an atopic disease in a subject, the method comprising administering to the subject a therapeutically effective amount of a polypeptide, said polypeptide comprising (i) amino acids 31-133 of SEQ ID NO: 3; (ii) amino acids 31-134 of SEQ ID NO: 4; (iii) an amino acid sequence that is at least 90% identical or similar to amino acids 31-133 of SEQ ID NO: 3; or (iv) an amino acid sequence that is at least 90% identical or similar to amino acids 31-134 of SEQ ID NO: 4; or (v) an amino acid sequence that is at least 90% identical to a tim-4 polypeptide comprising an amino acid sequence selected from the group consisting of SEQ ID NO: 3, SEQ ID NO: 4, SEQ ID NO: 9, SEQ ID NO:10, SEQ ID NO:11 and SEQ ID NO:12.

In some embodiments, the polypeptide comprises an amino acid sequence that is at least 65%, 70%, 75%, 85%, 90%, 95%, 96%, 97%, 98%, 99% or 99.5% identical or similar to the sequence set forth in SEQ ID NO: 3 or 4, or to a segment of such sequence, such as the IgV domain or the mucin domain. The polypeptide may comprise, for example, a domain having a sequence that is 98% identical or similar to residues 31-133 of SEQ ID NO:3, followed by a segment whose sequence shares little or no homology to SEQ ID NO:3, such as followed by an Fc domain of an immunoglobulin.

The methods provided by the invention for preventing, or for reducing the likelihood of becoming afflicted with, an atopic disease, are based, in part, on applicants discovery that tim-4 binds to tim-1, combined with the link between infection with the Hepatitis A virus, which binds to tim-1, and the resulting reduced likelihood of being afflicted with an atopic disease (McIntire J J et al., (2003) Immunology: hepatitis A virus link to atopic disease. Nature; 425(6958):576; von Hertzen L C, (2000) Puzzling associations between childhood infections and the later occurrence of asthma and atopy Ann Med.; 32(6):397-400; Bodner C et al. (2000) Childhood exposure to infection and risk of adult onset wheeze and atopy. Thorax. 55(5):383-7). Accordingly, in some embodiments, the methods for preventing or reducing the likelihood of being afflicted with atopic disease are methods of preventing or reducing the likelihood of being afflicted with atopic disease in a subject that has not been previously infected with the hepatitis A virus, while in a related embodiment the subject is seronegative for anti-Hepatitis A antibodies. In another embodiment, the subject is a child, or a subject younger than 10. In another embodiment of the methods described herein, the atopic disease is selected from the group consisting of asthma, rhinitis, eczema and hay fever.

Some of the methods described herein employ agents which reduce expression or activity of tim-1, tim-2 tim-4 or both, or that reduce the binding of tim-1 to tim-4 or tim-2 to semaphorin4A i.e. tim-1, tim-2 or tim-4 antagonists. In some embodiments of the methods described herein, the therapeutic agent does not comprise (i) an antibody; or (ii) a fragment thereof, capable of specifically binding to tim-1, tim-2 or tim-4. In another embodiment, the therapeutic agent does not comprise a viral protein, such as a viral protein from a hepatitis virus.

In some embodiments, the tim-1, tim-2 or tim-4 antagonist comprises an RNAi antisense oligonucleotide such as a double stranded RNA molecule or a DNA construct capable of generating double stranded RNA. Double stranded RNA includes, but is not limited to, hairpin RNA and RNA formed by two complementary single stranded RNA molecules. Antisense oligonucleotides are relatively short nucleic acids that are complementary (or antisense) to the coding strand (sense strand) of the mRNA encoding a particular polypeptide. Although antisense oligonucleotides are typically RNA based, they can also be DNA based. Additionally, antisense oligonucleotides are often modified to increase their stability.

Without being bound by theory, the binding of these relatively short oligonucleotides to the mRNA is believed to induce stretches of double stranded RNA that trigger degradation of the messages by endogenous RNAses. Additionally, sometimes the oligonucleotides are specifically designed to bind near the promoter of the message, and under these circumstances, the antisense oligonucleotides may additionally interfere with translation of the message. Regardless of the specific mechanism by which antisense oligonucleotides function, their administration to a cell, tissue or organism allows the degradation of the mRNA encoding a specific polypeptide. Accordingly, antisense oligonucleotides decrease the expression and/or activity of a particular polypeptide.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or compounds facilitating transport across the cell membrane (see, e.g., Letsinger et al., 1989, Proc. Natl. Acad. Sci. USA. 86:6553-6556; Lemaitre et al., 1987, Proc. Natl. Acad. Sci. 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents (See, e.g., Krol et al., 1988, BioTechniques 6:958-976) or intercalating agents. (See, e.g., Zon, 1988, Pharm. Res. 5:539-549). To this end, the oligonucleotide may be conjugated to another molecule.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxytriethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including but not limited to arabinose, 2-fluoroarabinose, xylulose, and hexose. The antisense oligonucleotide can also contain a neutral peptide-like backbone. Such molecules are termed peptide nucleic acid (PNA)-oligomers and are described, e.g., in Perry-O'Keefe et al. (1996) Proc. Natl. Acad. Sci. USA. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an -anomeric oligonucleotide. An -anomeric oligonucleotide forms specific double-stranded hybrids with complementary RNA in which, contrary to the usual -units, the strands run parallel to each other (Gautier et al., 1987, Nucl.

Acids Res. 15:6625-6641). The oligonucleotide is a 2'-O-methylribonucleotide (Inoue et al., 1987, Nucl. Acids Res. 15:6131-6148), or a chimeric RNA-DNA analogue (Inoue et al., 1987, FEBS Lett. 215:327-330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. USA. 85:7448-7451), etc.

The selection of an appropriate oligonucleotide can be readily performed by one of skill in the art. Given the nucleic acid sequence encoding a particular polypeptide, one of skill in the art can design antisense oligonucleotides that bind said sequence and test these oligonucleotides in an in vitro or in vivo system to confirm that they bind to and mediate the degradation of the mRNA encoding the particular polypeptide. To design an antisense oligonucleotide that specifically binds to and mediates the degradation of a particular mRNA, it is important that the sequence recognized by the oligonucleotide is unique or substantially unique to that particular mRNA. For example, sequences that are frequently repeated across mRNA may not be an ideal choice for the design of an oligonucleotide that specifically recognizes and degrades a particular message. One of skill in the art can design an oligonucleotide, and compare the sequence of that oligonucleotide to nucleic acid sequences that are deposited in publicly available databases to confirm that the sequence is specific or substantially specific for a particular polypeptide.

In another example, it may be desirable to design an antisense oligonucleotide that binds to and mediates the degradation of more than one message. In one example, the messages may encode related polypeptide such as isoforms or functionally redundant polypeptide. In such a case, one of skill in the art can align the nucleic acid sequences that encode these related polypeptides, and design an oligonucleotide that recognizes both messages.

A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it may be difficult to achieve intracellular concentrations of the antisense sufficient to suppress translation on endogenous tim-1, tim-2 or tim-4 mRNAs in certain instances. Therefore another approach utilizes a recombinant DNA construct in which the antisense oligonucleotide is placed under the control of a strong pol III or pol II promoter. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. USA. 78:1441-1445), the regulatory sequences of the metallothionein gene (Brinster et al, 1982, Nature 296:39-42), etc. Any type of plasmid, cosmid, YAC or viral vector can be used to prepare the recombinant DNA construct that can be introduced directly into the tissue site. Alternatively, viral vectors can be used which selectively infect the desired tissue, in which case administration may be accomplished by another route (e.g., systematically).

RNAi constructs comprise double stranded RNA that can specifically block expression of a target gene. "RNA interference" or "RNAi" is a term initially applied to a phenomenon observed in plants and worms where double-stranded RNA (dsRNA) blocks gene expression in a specific and post-transcriptional manner. Without being bound by theory, RNAi appears to involve mRNA degradation, however the biochemical mechanisms are currently an active area of research. Despite some mystery regarding the mechanism of action, RNAi provides a useful method of inhibiting gene expression in vitro or in vivo. As used herein, the term "dsRNA" refers to siRNA molecules, or other RNA molecules including a double stranded feature and able to be processed to siRNA in cells, such as hairpin RNA moieties. The term "loss-of-function," as it refers to genes inhibited by the subject RNAi method, refers to a diminishment in the level of expression of a gene when compared to the level in the absence of RNAi constructs.

As used herein, the phrase "mediates RNAi" refers to (indicates) the ability to distinguish which RNAs are to be degraded by the RNAi process, e.g., degradation occurs in a sequence-specific manner rather than by a sequence-independent dsRNA response, e.g., a PKR response.

As used herein, the term "RNAi construct" is a generic term used throughout the specification to include small interfering RNAs (siRNAs), hairpin RNAs, and other RNA species which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

"RNAi expression vector" (also referred to herein as a "dsRNA-encoding plasmid") refers to replicable nucleic acid constructs used to express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences. The choice of promoter and other regulatory elements generally varies according to the intended host cell. In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. Thus, the invention has the advantage of being able to tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of an nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, any modified ribonucleotide can be introduced by in vitro enzymatic or organic synthesis.

Methods of chemically modifying RNA molecules can be adapted for modifying RNAi constructs (see, for example, Heidenreich et al. (1997) *Nucleic Acids Res*, 25:776-780; Wilson et al. (1994) *J Mol Recog* 7:89-98; Chen et al. (1995) *Nucleic Acids Res* 23:2661-2668; Hirschbein et al. (1997) *Antisense Nucleic Acid Drug Dev* 7:55-61). Merely to illustrate, the backbone of an RNAi construct can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the polypeptide complex. In a particular embodiment, the 21-23 nucleotides siRNA molecules comprise a 3' hydroxyl group.

The siRNA molecules of the present invention can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (Caplen, et al. (2001) *Proc Natl Acad Sci USA*, 98:9742-9747; Elbashir, et al. (2001) *EMBO J*, 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In certain preferred embodiments, at least one strand of the siRNA molecules has a 3' overhang from about 1 to about 6 nucleotides in length, though may be from 2 to 4 nucleotides in length. More preferably, the 3' overhangs are 1-3 nucleotides in length. In certain embodiments, one strand having a 3' overhang and the other strand being blunt-ended or also having an overhang. The length of the overhangs may be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

In other embodiments, the RNAi construct is in the form of a long double-stranded RNA. In certain embodiments, the RNAi construct is at least 25, 50, 100, 200, 300 or 400 bases. In certain embodiments, the RNAi construct is 400-800 bases in length. The double-stranded RNAs are digested intracellularly, e.g., to produce siRNA sequences in the cell. However, use of long double-stranded RNAs in vivo is not always practical, presumably because of deleterious effects which may be caused by the sequence-independent dsRNA response. In such embodiments, the use of local delivery systems and/or agents which reduce the effects of interferon or PKR are preferred.

In certain embodiments, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., *Genes Dev*, 2002, 16:948-58; McCaffrey et al., *Nature*, 2002, 418:38-9; McManus et al., *RNA*, 2002, 8:842-50; Yu et al., *Proc Natl Acad Sci USA*, 2002, 99:6047-52). Preferably, such hairpin RNAs are engineered in cells or in an animal to ensure continuous and stable suppression of a desired gene. It is known in the art that siRNAs can be produced by processing a hairpin RNA in the cell.

In yet other embodiments, a plasmid is used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO01/77350 describes an exemplary vector for bi-directional transcription of a transgene to yield both sense and antisense RNA transcripts of the same transgene in a eukaryotic cell. Accordingly, in certain embodiments, the present invention provides a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

RNAi constructs can comprise either long stretches of double stranded RNA identical or substantially identical to the target nucleic acid sequence or short stretches of double stranded RNA identical to substantially identical to only a region of the target nucleic acid sequence. Exemplary methods of making and delivering either long or short RNAi constructs can be found, for example, in WO01/68836 and WO01/75164.

In another embodiment, the tim-1, tim-2 or tim-4 antagonist are ribozyme molecules which reduce the expression levels of tim-1, tim-2 or tim-4. Ribozyme molecules designed to catalytically cleave an mRNA transcript can be used to prevent translation of tim-1, tim-2 or tim-4 mRNA (See, e.g., PCT International Publication WO90/11364, published Oct. 4, 1990; Sarver et al., 1990, Science 247:1222-1225 and U.S. Pat. No. 5,093,246). While ribozymes that cleave mRNA at site-specific recognition sequences can be used to destroy particular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585-591.

The ribozymes that may be used in the methods described herein also include RNA endoribonucleases (hereinafter "Cech-type ribozymes") such as the one which occurs naturally in Tetrahymena thermophila (known as the IVS, or L-19 IVS RNA) and which has been extensively described by Thomas Cech and collaborators (Zaug, et al., 1984, Science, 224:574-578; Zaug and Cech, 1986, Science, 231:470-475; Zaug, et al., 1986, Nature, 324:429-433; published International patent application No. WO88/04300 by University Patents Inc.; Been and Cech, 1986, Cell, 47:207-216). The Cech-type ribozymes have an eight base pair active site that hybridizes to a target RNA sequence whereafter cleavage of the target RNA takes place. The invention encompasses those Cech-type ribozymes that target eight base-pair active site sequences.

As in the antisense approach, the ribozymes can be composed of modified oligonucleotides (e.g., for improved stability, targeting, etc.) and can be delivered to cells in vitro or in vivo. A preferred method of delivery involves using a DNA construct "encoding" the ribozyme under the control of a strong constitutive pol III or pol II promoter, so that transfected cells will produce sufficient quantities of the ribozyme to destroy targeted messages and inhibit translation. Because ribozymes unlike antisense molecules, are catalytic, a lower intracellular concentration is required for efficiency.

In another embodiment of the methods described herein, the tim-1, tim-2 or tim-4 antagonist comprises an anti-Tim-1, anti-Tim-2 or an anti-Tim-4 antibody. Antibodies which bind the tim-1, tim-2 or tim-4 extracellular domain, such as monoclonal antibodies, can be generated by one skilled in the art, and those antibodies can be further tested for their ability to block binding of a tim-1 to tim-4 using the methods provided by the instant invention. The preferred antagonist antibodies would block the binding interactions between tim-1 or tim-4 without themselves acting as an activator of tim-1 activity or tim-4 activity. Using the assays described in the experimental procedures for example, one skilled in the art can determine if a candidate antibody is an activator of tim-1 and thus both an inducer of a Th1 response and an inhibitor of a Th2 response. Such testing may be performed by administering the antibody to an immunized mouse and testing for in vitro proliferation and cytokine production by T cells isolated for the spleen of the mouse. Preferred antibodies for increasing a Th2 response (or reducing a Th1 response) would both block binding of tim-1 to tim-4 ligands and not induce activation of tim-1. Activation of tim-1 may be monitored, for example, by monitoring the intracellular tyrosine phosphorylation of tim-1.

The term "antibody" as used herein refers to immunoglobulin molecules and immunologically active portions of immunoglobulin (Ig) molecules, i.e., molecules that contain an antigen binding site that specifically binds (immunoreacts with) an antigen. Such antibodies include, e.g., polyclonal, monoclonal, chimeric, single chain, $F_{ab}$, $F_{ab}$' and $F(ab')_2$ fragments, and an Fab expression library. In general, an antibody molecule obtained from humans relates to any of the classes IgG, IgM, IgA, IgE and IgD, which differ from one another by the nature of the heavy chain present in the molecule. Certain classes have subclasses as well, such as $IgG_1$, $IgG.sub_2$, and others. Furthermore, in humans, the light chain may be a kappa chain or a lambda chain. Reference herein to antibodies includes a reference to all such classes, subclasses and types of human antibody species. Antibodies to Tim-1 or Tim-4 polypeptides also include antibodies to fusion polypeptides containing Tim-1 or Tim-4 polypeptides or fragments of Tim-1 or Tim-4 polypeptides.

A Tim-1, Tim-2 or Tim-4 polypeptide can be used as an antigen, or a portion or fragment thereof, and additionally can be used as an immunogen to generate antibodies that immunospecifically bind the antigen, using standard techniques for polyclonal and monoclonal antibody preparation. Antigenic peptide fragments of the antigen for use as immunogens include, e.g., at least 7 amino acid residues of the amino acid sequence of the amino terminal region, such as an amino acid sequence shown in SEQ ID NOs:1-4, and encompass an epitope thereof such that an antibody raised against the peptide forms a specific immune complex with the full length polypeptide or with any fragment that contains the epitope. Preferably, the antigenic peptide comprises at least 10 amino acid residues, or at least 15 amino acid residues, or at least 20 amino acid residues, or at least 30 amino acid residues. Preferred epitopes encompassed by the antigenic peptide are regions of the polypeptide that are located on its surface; commonly these are hydrophilic regions. In preferred embodiment, the antigenic peptide comprises a segments of, or the entire, IgV and/or mucin domains of Tim-1, Tim-2 or Tim-4.

In some embodiments, at least one epitope encompassed by the antigenic peptide is a region of Tim-1, Tim-2 or Tim-4 polypeptide that is located on the surface of the polypeptide, e.g., a hydrophilic region. A hydrophobicity analysis of a Tim-1 or Tim-4 polypeptide will indicate which regions of an Tim-1 or Tim-4 polypeptide are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods (1981) *Proc. Nat. Acad. Sci. USA* 78: 3824-3828; Kyte and Doolittle (1982) J. Mol. Biol. 157: 105-142. Antibodies that are specific for one or more domains within an antigenic polypeptide, or derivatives, fragments, analogs or homologs thereof, are also provided herein. In some embodiments, a derivative, fragment, analog, homolog or ortholog of Tim-1 or Tim-4 may be utilized as an immunogen in the generation of antibodies that immunospecifically bind these polypeptide components.

Various procedures known within the art may be used for the production of polyclonal or monoclonal antibodies directed against a polypeptide of the invention, or against derivatives, fragments, analogs homologs or orthologs thereof. See, for example, ANTIBODIES: A LABORATORY MANUAL, Harlow and Lane (1988) Cold Spring Harbor Laboratory Press, Cold Spring Harbor, N.Y. Some of these antibodies are discussed below.

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen binding site capable of immunoreacting with a particular epitope of the antigen characterized by a unique binding affinity for it.

Monoclonal antibodies can be prepared using hybridoma methods, such as those described by Kohler and Milstein (1975) Nature, 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The antibodies directed against the polypeptide antigens of the invention can further comprise humanized antibodies or human antibodies. These, antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al. (1986) Nature, 321:522-525; Riechmann et al. (1988) Nature, 332:323-327; Verhoeyen et al. (1988) Science, 239:1534-1536), by substituting rodent CDRs or CDR sequences for the corresponding sequences of a human antibody. (See also U.S. Pat. No. 5,225,539.)

Antibody fragments that contain the idiotypes to a the tim-1, tim-2 or tim-4 may be produced by techniques known in the art including, but not limited to: (i) an F(ab')$_2$ fragment produced by pepsin digestion of an antibody molecule; (ii) an Fab fragment generated by reducing the disulfide bridges of an F(ab')$_2$ fragment; (iii) an Fab fragment generated by the treatment of the antibody molecule with papain and a reducing agent and (iv) Fv fragments.

In some embodiments of the methods described herein, the tim-1, tim-2 or tim-4 antagonist comprises a monoclonal antibody, preferably human or humanized, antibodies that have binding specificities for at least two different antigens. In the present case, one of the binding specificities is for tim-1, tim-2 or tim-4. The second binding target is any other antigen, and advantageously is a cell-surface polypeptide or receptor or receptor subunit.

In some embodiments of the methods described herein, the tim-1, tim-2 or tim-4 antagonist comprises a tim-1, tim-2 or tim-4 polypeptide, analog, variant, or fragments thereof. In one embodiment, the antagonist comprises a tim-1 IgV domain, a tim-2 IgV domain, a tim-4 IgV domain, a tim-1 mucin domain, a tim-2 mucin domain, a tim-4 mucin domain, or combinations thereof. In another embodiment, the antagonist comprises a polypeptide which comprises an amino acid sequence which is at least 60%, 65%, 70%, 75%, 80%, 85%, 90%, 95%, 96%, 97%, 98% or 99% identical or similar to the tim-1 IgV domain, a tim-4 IgV domain, a tim-2 IgV domain, a tim-1 mucin domain, a tim-2 mucin domain or a tim-4 mucin domain sequences. Without being bound by theory, such antagonist may act by titrating one of the tim ligands such that they may not bind to the tim polypeptide. Such titration may occur, for example, by steric occlusion of the binding site.

A chimeric or fusion polypeptide for use in the present invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary-overhangs between two consecutive gene fragments that can subsequently be annealed and reamplified to generate a chimeric gene sequence (see, for example, Ausubel et al (eds.) CURRENT PROTOCOLS IN MOLECULAR BIOLOGY, John Wiley & Sons, 1992). Moreover, many expression vectors are commercially available that encode a fusion moiety (e.g., an Fc region of an immunoglobulin heavy chain). A Tim-1, Tim-2 or Tim-4 encoding nucleic acid can be cloned into such an expression vector such that the fusion moiety is linked in-frame to the immunoglobulin polypeptide.

In some embodiments, the antagonist comprises a Tim-1, Tim-2 or Tim-4 variant sequence having a mutation in a naturally-occurring Tim-1, Tim-2 or Tim-4 sequence that results in higher affinity binding between the mutated form and its binding partner relative to the non-mutated sequence. In some embodiments, the Tim polypeptide or Tim polypeptide moiety is provided as a variant Tim polypeptide having mutations in the naturally-occurring Tim sequence (wild type) that results in an Tim sequence more resistant to proteolysis (relative to the non-mutated sequence).

The second polypeptide, i.e. the polypeptide to which the Tim-1, Tim-2 or Tim-4 sequences are fused to, is preferably soluble. In some embodiments, the second polypeptide enhances the half-life, (e.g., the serum half-life) of the linked polypeptide. In some embodiments, the second polypeptide includes a sequence that facilitates association of the fusion polypeptide with a second Tim-1 polypeptide. In preferred embodiments, the second polypeptide includes at least a region of an immunoglobulin polypeptide. Immunoglobulin fusion polypeptides are known in the art and are described in e.g., U.S. Pat. Nos. 5,516,964; 5,225,538; 5,428,130; 5,514,582; 5,714,147; and 5,455,165. In some embodiments, the second polypeptide comprises a full-length immunoglobulin polypeptide. Alternatively, the second polypeptide comprises less than full-length immunoglobulin polypeptide, e.g., a heavy chain, light chain, Fab, Fab$_2$, Fv, or Fc. Preferably, the second polypeptide includes the heavy chain of an immunoglobulin polypeptide. More preferably, the second polypeptide comprises the Fc region of an immunoglobulin polypeptide. In some embodiments, the second polypeptide has less effector function than the effector function of a Fc region of a wild-type immunoglobulin heavy chain. Fc effector function includes for example, Fc receptor binding, complement fixation and T cell depleting activity (see for example, U.S. Pat. No. 6,136,310). Methods of assaying T cell depleting activity, Fc effector function, and antibody stability are known in the art. In one embodiment the second polypeptide has low or no affinity for the Fc receptor. In an alternative embodiment, the second polypeptide has low or no affinity for complement polypeptide C1q.

In one preferred embodiment, the antagonist used in the methods described herein is a small organic molecule, e.g., other than a peptide or oligonucleotide, having a molecular weight of less than about 2,000 Daltons, which blocks the binding of tim-1 to tim-4, of tim-2 to semaphorin4A, or which prevents tim-1 activation upon tim-4 binding Such agents can be identified, for example, using the methods provided by the instant invention. In another embodiment, the agent is a peptide or peptide derivative which structurally mimics the portion of a tim-1 that binds to tim-4, or vice-versa. Some of the methods described herein employ agents which increase the expression or activity of tim-1, tim-4 or both, or that reduce the binding of tim-1 to tim-4 i.e. tim-1 or tim-4 antagonists.

In some embodiments, the agent which increases tim-1 or tim-4 activity in the methods described herein is an antibody. Antibodies can be generated which bind to tim-1 and mimic the binding of tim-4, resulting in intracellular signaling and an inhibition of a Th2 response. Antibodies to tim-1 and tim-4 may be generated as described in the previous sections. For example, antibodies may be generated which bind to the extracellular domain of tim-1, and that antibody may be tested to determine whether the antibody promotes or inhibits the activation of tim-1.

In one specific embodiment, the agonist comprises an antibody which binds to the tim-1/tim-4 complex. Without intending to be bound by theory, and antibody which binds to a tim-1/tim-4 complex may stabilize or promote complex formation and thus increase tim-1 and/or tim-4 signaling. An antibody which binds to a tim-1/tim-4 complex may be generated by immunizing animals with a tim-1/tim-4 polypeptide complex, such as a complex between their extracellular domains. Alternatively, the antibody may be generated by in vitro selection techniques from randomized antibody libraries by selecting those antibodies which bind to a tim-1/tim-4 complex.

In some embodiments of the methods described herein, the tim-1, tim-2 or tim-4 agonist comprises a tim-1, tim-2 or tim-4 polypeptide, analog, variant, or fragment thereof. In one embodiment, the agonist comprises a tim-1 IgV domain, a tim-2 IgV domain, a tim-4 IgV domain, a tim-1 mucin domain, a tim-2 mucin domain, a tim-4 mucin domain, or combinations thereof. In another embodiment, the agonist comprises a polypeptide which comprises an amino acid sequence which is at least 60%, 65%, 70%, 75%, 80%, 85%, 90%, 95%, 96%, 97%, 98% or 99% identical or similar to the tim-1 IgV domain, a tim-4 IgV domain, a tim-1 mucin domain, or a tim-4 mucin domain. Without being bound by theory, such agonists may act by structurally mimicking the activity of tim-1, tim-2 or tim-4. In one embodiment, the agonist comprises a tim-4 IgV and/or a tim-4 mucin domain. In another embodiment, the agonist comprises a dimer of polypeptides, each comprising a tim-4 IgV and/or a tim-4 mucin domain polypeptide. Such agonist may be used to crosslink and activate tim-1 receptors. In other embodiments, the polypeptide agonist may be administered as a nucleic acid encoding said polypeptide, such as through an adenovirus.

Tim-1, Tim-2 or Tim-4, or active fragments of these polypeptides used as agonists can be fused to carrier molecules such as immunoglobulins for use in the herein described methods. For example, soluble forms of Tim-1 may be fused through "linker" sequences to the Fc portion of an immunoglobulin or to the Fc portion of the immunoglobulin. Other fusions polypeptides, such as those with GST (i.e., glutathione S-transferase), LexA, or MBP (i.e., maltose binding polypeptide), may also be used. In a further embodiment, Tim-4 or Tim-1 agonist fusion polypeptides may be linked to one or more additional moieties. For example, the Tim-4 or Tim-1 fusion polypeptide may additionally be linked to a GST fusion polypeptide in which the Tim-1 fusion polypeptide sequences are fused to the C-terminus of the GST sequences. Such fusion polypeptides can facilitate the purification of the Tim-4 or Tim-1 fusion polypeptide. In another embodiment, the fusion polypeptide includes a heterologous signal sequence (i.e., a polypeptide sequence that is not present in a polypeptide naturally encoded by an Tim-4 or Tim-1 nucleic acid) at its N-terminus. For example, the native Tim-4 or Tim-1 signal sequence can be removed and replaced with a signal sequence from another polypeptide.

In some embodiments, the agonist comprises a Tim-1, Tim-2 or Tim-4 variant sequence having a mutation in the naturally-occurring Tim-4 or Tim-1 sequence that results in higher affinity binding between the mutated form and its binding partner relative to the non-mutated sequence, e.g. a higher affinity binding of a mutated Tim-1 polypeptide for Tim-4. In some embodiments, a Tim-1, Tim-2 or Tim-4 moiety is provided as a variant polypeptide having mutations in the naturally-occurring tim sequence (wild type) that results in an polypeptide more resistant to proteolysis (relative to the non-mutated sequence). For instance, protease cleavage sites for serine, aspartate or cysteine proteases on the tim protein can be removed.

In one preferred embodiment, the agonist used in the methods described herein is a small organic molecule, e.g., other than a peptide or oligonucleotide, having a molecular weight of less than about 2,000 Daltons, which promotes the binding of tim-1 to tim-4 or which causes tim-1 activation in the absence of tim-4 binding to tim-1. Such agents can be identified, for example, using the methods provided by the instant invention. In another embodiment, the agent is a peptide or peptide derivative which structurally mimics the portion of a tim-4 which binds to tim-1, or the portion of tim-2 that binds to semaphorin4A. Such a peptide may act as an agonistic by inducing activation of tim-1 or tim-4 and their ligand(s) or as an antagonist by competing for binding between the tim proteins.

V. Identifying Agents that Modulate Binding between Tim-1 and Tim-4

Another aspect of the invention provides a method of identifying agents that modulate immune responses, such as by identifying agents which modulate the binding between tim-1 and tim-4. Agents identified using the methods described herein may be used to modulate $T_H1$ and $T_H2$ responses in a subject in need thereof. Agents which block the tim-1/tim-4 interaction would be predicted to prevent activation of tim-1, leading to increased Th2 activation and reduced Th1 activation.

In one aspect, the identification of a tim-1/tim-4 complex as described in the invention facilitates rational design of agonists and antagonists of complex formation, based on the structural features of the tim-1 and tim-4 polypeptides which can be determined using X-ray crystallography, neuron diffraction, nuclear magnetic resonance spectrometry, and other techniques well-known to one skilled in the art. Methods for rational drug design are well known in the art (see Chemical and Structural Approaches to Rational Drug Design, David B. Weiner, William V. Williams, CRC Press (1994); Rational Drug Design: Novel Methodology and Practical Applications, Vol. 719, Abby L. Parrill (Editor), American Chemical Society (1999); Structure-based Ligand Design, Klaus Gubemator, Wiley, John & Sons, Incorporated (1998)).

Another aspect of the invention provides methods for screening agents that promote or block the formation of a complex between tim-1 and tim-4. Such methods may be performed in vitro or in a cell, and they may be performed using full-length polypeptides or soluble forms of the one or both of the polypeptides. In some embodiment of the screening methods described herein, soluble polypeptides comprising the IgV domain, and optionally the mucin domain, of tim-1 or of tim-4 may be used. A variety of other reagents may be included in the screening assay. These include reagents like salts, neutral polypeptides, e.g. albumin, detergents, etc. that are used to facilitate optimal polypeptide-polypeptide binding and/or reduce non-specific or background interactions. Reagents that improve the efficiency of the assay, such as protease inhibitors, nuclease inhibitors, anti-microbial agents, etc. may also be used. The mixture of components are added in any order that provides for the requisite binding. Incubations are performed at any suitable temperature, typically between 4° C. and 40° C. Incubation periods are selected for optimum activity, but may also be optimized to facilitate rapid high-throughput screening. Typically between 0.1 and 1 hours will be sufficient for in vitro assays.

The methods for the identification of agents of the present invention are well suited for screening libraries of compounds in multi-well plates (e.g., 96-well plates), with a different test compound or group of test compounds in each well. In particular, the methods may be employed with combinatorial libraries. These methods may be "miniaturized" in an assay system through any acceptable method of miniaturization, including but not limited to multi-well plates, such as 24, 48, 96 or 384-wells per plate, micro-chips or slides. The assay may be reduced in size to be conducted on a micro-chip support, advantageously involving smaller amounts of reagents and other materials. Any miniaturization of the process which is conducive to high-throughput screening is within the scope of the invention.

One specific aspect of the invention provides a method of identifying an agent that modulates the binding between a tim-1 polypeptide and a tim-4 polypeptide comprising: (a) contacting the tim-1 polypeptide and the tim-4 polypeptide in the presence of a test agent; and (b) determining the effect of the test agent on the binding of the tim-1 polypeptide and the tim-4 polypeptide; thereby identifying a agent that modulates the binding between a tim-1 polypeptide and a tim-4 polypeptide.

A related aspect of the invention provides a method of identifying an agent that modulates an immune response, the method comprising (a) contacting the tim-1 polypeptide and the tim-4 polypeptide in the presence of a test agent; and (b) determining the effect of the test agent on the binding of the tim-1 polypeptide and the tim-4 polypeptide; thereby identifying an agent that modulates an immune response.

In some aspect of the invention the agents are identified through in vitro assays. A variety of assay formats will suffice and, in light of the present disclosure, those not expressly described herein will nevertheless be comprehended by one of ordinary skill in the art. Assay formats which approximate such conditions as formation of polypeptide complexes, enzymatic activity, may be generated in many different forms, and include assays based on cell-free systems, e.g. purified polypeptides or cell lysates, as well as cell-based assays which utilize intact cells. Simple binding assays can also be used to detect agents which bind to tim-1 or tim-4. Such binding assays may also identify agents that act by disrupting the interaction between a tim-1 polypeptide and a tim-4 polypeptide. Agents to be tested can be produced, for example, by bacteria, yeast or other organisms (e.g. natural products), produced chemically (e.g. small molecules, including peptidomimetics), or produced recombinantly. Because tim-1 and tim-4 are transmembrane polypeptides, preferred embodiments of the assays and methods described to identify agents which modulate complex formation between tim-1 and tim-4 employ soluble forms of these polypeptides rather than full-length polypeptide. Soluble forms include those lacking the transmembrane domain and/or those comprising the IgV domain or fragments thereof which retain their ability to bind.

In many drug screening programs which test libraries of compounds and natural extracts, high throughput assays are desirable in order to maximize the number of compounds surveyed in a given period of time. Assays of the present invention which are performed in cell-free systems, which may be developed with purified or semi-purified polypeptides or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other polypeptides or changes in enzymatic properties of the molecular target.

In preferred in vitro embodiments of the present assay, a reconstituted tim-1/tim-4 complex comprises a reconstituted mixture of at least semi-purified polypeptides. By semi-purified, it is meant that the polypeptides utilized in the reconstituted mixture have been previously separated from other cellular or viral polypeptides. For instance, in contrast to cell lysates, the polypeptides involved in tim-1/tim-4 complex formation are present in the mixture to at least 50% purity relative to all other polypeptides in the mixture, and more preferably are present at 90-95% purity. In certain embodiments of the subject methods, the reconstituted polypeptide mixture is derived by mixing highly purified polypeptides such that the reconstituted mixture substantially lacks other polypeptides (such as of cellular or viral origin) which might interfere with or otherwise alter the ability to measure tim-1/tim-4 complex assembly and/or disassembly.

Assaying tim-1/tim-4 complexes, in the presence and absence of a test agent, can be accomplished in any vessel suitable for containing the reactants. Examples include microtitre plates, test tubes, and micro-centrifuge tubes. In a screening assay, the effect of a test agent may be assessed by, for example, assessing the effect of the test agent on kinetics, steady-state and/or endpoint of the reaction.

In one embodiment of the present invention, drug screening assays can be generated which detect inhibitory agents on the basis of their ability to interfere with assembly or stability of the tim-1/tim-4 complex. In an exemplary binding assay, the compound of interest is contacted with a mixture comprising a tim-1/tim-4 complex. Detection and quantification of tim-1/tim-4 complexes provides a means for determining the compound's efficacy at inhibiting (or potentiating) interaction between the two polypeptides. The efficacy of the compound can be assessed by generating dose response curves from data obtained using various concentrations of the test compound. Moreover, a control assay can also be performed to provide a baseline for comparison. In the control assay, the formation of complexes is quantitated in the absence of the test compound.

Complex formation may be detected by a variety of techniques. For instance, modulation in the formation of complexes can be quantitated using, for example, detectably labeled polypeptides (e.g. radiolabeled, fluorescently labeled, or enzymatically labeled), by immunoassay, or by chromatographic detection. Surface plasmon resonance systems, such as those available from Biacore© International AB (Uppsala, Sweden), may also be used to detect polypeptide-polypeptide interaction The polypeptides and peptides described herein may be immobilized. Often, it will be desirable to immobilize the peptides and polypeptides to facilitate separation of complexes from uncomplexed forms of one of the polypeptides, as well as to accommodate automation of the assay. The peptides and polypeptides can be immobilized on any solid matrix, such as a plate, a bead or a filter. The peptide or polypeptide can be immobilized on a matrix which contains reactive groups that bind to the polypeptide. Alternatively or in combination, reactive groups such as cysteines in the polypeptide can react and bind to the matrix. In another embodiment, the polypeptide may be expressed as a fusion polypeptide with another polypeptide which has a high binding affinity to the matrix, such as a fusion polypeptide to streptavidin which binds biotin with high affinity.

In an illustrative embodiment, a fusion polypeptide can be provided which adds a domain that permits the polypeptide to be bound to an insoluble matrix. For example, a GST-TIM-1-IgV-domain fusion polypeptide, which comprises the IgV domain of tim-1 fused to glutathione transferase, can be adsorbed onto glutathione sepharose beads (Sigma Chemical, St. Louis, Mo.) or glutathione derivatized microtitre plates, which are then combined with tim-4 or a soluble fragment thereof, e.g. an $^{35}$S-labeled polypeptide, and the test compound and incubated under conditions conducive to complex formation. Following incubation, the beads are washed to remove any unbound interacting polypeptide, and the matrix bead-bound radiolabel determined directly (e.g. beads placed in scintillant), or in the supernatant after the complexes are dissociated, e.g. when microtitre plate is used. Alternatively, after washing away unbound polypeptide, the complexes can be dissociated from the matrix, separated by SDS-PAGE gel, and the level of interacting polypeptide found in the matrix-bound fraction quantitated from the gel using standard electrophoretic techniques.

It will be understood that various modifications of the above-described assay are included within the scope of the present invention. For example, the roles of the polypeptides can be switched—that is, the tim-4 polypeptide may be immobilized to the solid support and a solution containing the a tim-1 polypeptide may be contacted with the bound tim-4 polypeptide. Additionally, the immobilized polypeptide or the free polypeptide may be exposed to a test compound prior to the binding assay, and the effects of this pre-exposure may be assessed relative to controls. Compounds identified in this manner also inhibit the binding of the tim-1 to tim-4 or vice versa. Alternatively, the test compound may be added subsequent to the mixing of tim-1 and tim-4. A compound effective to reduce the level of binding in such an assay displaces tim-1 polypeptide from the tim-4 polypeptide or vice versa.

In addition to Western blots, other, more rapid, detection schemes, such as multi-well ELISA-type approaches, may be employed. For example, a partially-purified (e.g., by the GST methods above) tim-1 polypeptide may be attached to the bottoms of wells in a multi-well plate (e.g., 96-well plate) by introducing a solution containing the polypeptide into the plate and allowing the polypeptide to bind to the plastic. The excess polypeptide-containing solution is then washed out, and a blocking solution (containing, for example, bovine serum albumin (BSA)) is introduced to block non-specific binding sites. The plate is then washed several more times and a solution containing an tim-4 polypeptide and, in the case of experimental (vs. control) wells, a test compound added. Different wells may contain different test compound, different concentrations of the same test substance, different tim-1 polypeptides or tim-4 polypeptide, or different concentrations of tim-1 polypeptide or tim-4 polypeptide. Further, it will be understood that various modifications to this detection scheme may be made. For example, the wells of a multi-well plate may be coated with a polypeptide containing the tim-4 polypeptide, rather than the tim-1 polypeptide, and binding interactions assayed upon addition of a free tim-1 polypeptide. The wells may also be pre-coated with compound(s) that enhance attachment of the polypeptide to be immobilized and/or decrease the level of non-specific binding. For example, the wells may be derivatized to contain glutathione and may be pre-coated with BSA, to promote attachment of the immobilized polypeptide in a known orientation with the binding site(s) exposed.

Detection methods useful in such assays include antibody-based methods (i.e., an antibody directed against the "free" polypeptide), direct detection of a reporter moiety incorporated into the "free" polypeptide (such as a fluorescent label), and proximity energy transfer methods (such as a radioactive "free" polypeptide resulting in fluorescence or scintillation of molecules incorporated into the immobilized polypeptide or the solid support).

Yet another variation of the methods of the present invention for identifying a compound capable of affecting binding of a tim-1 polypeptide to a tim-4 polypeptide is through the use of affinity biosensor methods. Such methods may be based on the piezoelectric effect, electrochemistry, or optical methods, such as ellipsometry, optical wave guidance, and surface plasmon resonance (SPR). SPR is particular advantageous for monitoring molecular interactions in real-time, enabling a sensitive and comprehensive analysis of the effects of test compounds on the binding interactions between two polypeptides than the methods discussed above. This advantage is somewhat offset, however, by the lower throughput of the technique (as compared with multi-well plate-based methods).

As hereinbefore mentioned, a test compound can be said to have an effect on the binding between a tim-1 polypeptide and a tim-4 polypeptide if the compound has any effect on the binding of tim-1 to the tim-4 polypeptide (i.e., if the compound increases or decreases the binding), and the effect exceeds a threshold value (which is set to a desired level by the practitioner of the invention as described above; e.g., several-fold increase or several-fold decrease in binding). Preferably the effect on binding is a significant effect. The term "significant" as used herein, specifically in terms of a "significant effect", refers to a difference in a quantifiable parameter between two groups being compared that is statistically-significant using standard statistical tests. In some embodiments of the methods described herein, step (b) comprises comparing formation of a tim-1/tim-4 complex in the presence of the test agent with an suitable control. In some embodiments, the suitable control comprises the formation of a complex between the first polypeptide and the second polypeptide in the absence of the agent or compound being tested.

Therefore, in an embodiment of the present invention, there is provided a method of screening for compounds that affect the binding between a tim-1 polypeptide and a tim-4 polypeptide comprising: (a) contacting the tim-1 polypeptide and the tim-4 polypeptide in the presence of a test compound; (b) determining the effect of the test compound on the binding of the tim-1 polypeptide and the tim-4 polypeptide; and (c) identifying the compound as effective if its measured effect on the extent of binding is above a threshold level.

The term "affect the binding between a tim-1 polypeptide and a tim-4 polypeptide" means the test compound produces a difference in the binding between the tim-1 polypeptide and the tim-4 polypeptide in its presence as compared to the binding between the tim-1 polypeptide and the tim-4 polypeptide in its absence (control). Preferably this difference in binding is a significant difference. In a specific embodiment, a significant difference comprises at least a 10%, 20%, 30%, 40%, 50%, 75%, 100%, 150%, 200% or 500% increase or decrease in binding. The compound may inhibit or enhance the binding, or in terms of the affect on tim-1, act as an antagonist, an agonist or act as a compound which enhances the effects of other agonists or antagonists. The type of measurement used to quantify the effect of a test compound on the binding between a tim-1 polypeptide and a tim-4 polypeptide will depend on the type of assay and detection methods used and this can be readily determined by a person having skill in the art. For example, when using a biological screen that employs Western blotting as the means for detection, the binding can be measured using densitometry. The densitometry values may be normalized and a threshold level may be set based on the amount of variation in the signal between a series of control samples (i.e. without test compound). The smaller the variation, the smaller the effect of a test compound that can be reliably detected.

In still further embodiments of the present assays, the tim-1/tim-4 complex is generated in whole cells, taking advantage of cell culture techniques to support the subject assay. For example, as described below, the tim-1/tim-4 complex can be constituted in a eukaryotic cell culture system, such as a mammalian cell and a yeast cell. Other cells know to one skilled in the art may be used. Advantages to generating the subject assay in a whole cell include the ability to detect inhibitors which are functional in an environment more closely approximating that which therapeutic use of the inhibitor would require, including the ability of the agent to gain entry into the cell. Furthermore, certain of the in vivo embodiments of the assay, such as examples given below, are amenable to high through-put analysis of test agents. The components of the tim-1/tim-4 complex can be endogenous to the cell selected to support the assay. Alternatively, some or all of the components can be derived from exogenous sources. For instance, fusion polypeptides can be introduced into the cell by recombinant techniques (such as through the use of an expression vector), as well as by microinjecting the fusion polypeptide itself or mRNA encoding the fusion polypeptide.

In yet another embodiment, the tim-1 and tim-4 polypeptides can be used to generate an interaction trap assay (see also, U.S. Pat. Nos. 6,200,759 and 5,925,523; Zervos et al. (1993) Cell 72:223-232; Madura et al. (1993) J. Biol Chem 268:12046-12054; Bartel et al. (1993) Biotechniques 14:920-924; and Iwabuchi et al. (1993) Oncogene 8:1693-1696), for subsequently detecting agents which disrupt binding of the polypeptides to one and other.

The yeast two-hybrid polypeptide interaction assay may also be employed to identify compounds that affect the binding of a tim-1 polypeptide to a tim-4 polypeptide. The assay is based on the finding that most eukaryotic transcription activators are modular, i.e., that the activators typically contain activation domains that activate transcription, and DNA binding domains that localize the activator to the appropriate region of a DNA molecule.

In a two hybrid system, a first fusion polypeptide contains one of a pair of interacting polypeptides fused to a DNA binding domain, and a second fusion polypeptide contains the other of a pair of interacting polypeptides fused to a transcription activation domain. The two fusion polypeptides are independently expressed in the same cell, and interaction between the "interacting polypeptide" portions of the fusions reconstitute the function of the transcription activation factor, which is detected by activation of transcription of a reporter gene. At least two different cell-based two hybrid polypeptide-polypeptide interaction assay systems have been used to assess binding interactions and/or to identify interacting polypeptides. Both employ a pair of fusion hybrid polypeptides, where one of the pair contains a first of two "interacting" polypeptides fused to a transcription activation domain of a transcription activating factor, and the other of the pair contains a second of two "interacting" polypeptides fused to a DNA binding domain of a transcription activating factor.

In another embodiment, one of the polypeptides is expressed on a cell, such as on the cell surface, whereas the other polypeptide is a native or a recombinant polypeptide that is purified or partially purified and contacted with the cell, such as to allow formation of a complex.

In some embodiments, the agents identified as modulating the binding interaction between tim-1 and tim-4 may be further evaluated for functional effects, such as their effect on the induction of a Th1/Th2 response by T cells in vitro or in vivo, such as by using the assays described in the experimental section.

The test agent or test compound can be any agent or compound which one wishes to test including, but not limited to, polypeptides (including antibodies), peptides, nucleic acids (including RNA, DNA, antisense oligonucleotide, peptide nucleic acids), carbohydrates, organic compounds, inorganic compounds, natural products, library extracts, bodily fluids and other samples that one wishes to test for affecting the binding between a tim-1 and tim-4 polypeptide. In particular the test compound may be a peptide mimetic of a tim-1 polypeptide or a fragment thereof. In some embodiments the test agent is purified or partially purified agent, whereas in other embodiments it is not purified.

Test agents encompass numerous chemical classes, though typically they are organic molecules, preferably small organic compounds having a molecular weight of more than 50 and less than about 2,500 Daltons. test agents comprise functional groups necessary for structural interaction with polypeptides, particularly hydrogen bonding, and typically include at least an amine, carbonyl, hydroxyl or carboxyl group, preferably at least two of the functional chemical groups. The test agents often comprise cyclical carbon or heterocyclic structures and/or aromatic or polyaromatic structures substituted with one or more of the above functional groups. test agents are also found among biomolecules including, but not limited to: peptides, saccharides, fatty acids, steroids, purines, pyrimidines, derivatives, structural analogs or combinations thereof.

Test agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Libraries of small organic/peptide may be generated using combinatorial techniques such as those described in Blondelle et al. (1995) Trends Anal. Chem. 14:83; the Affymax U.S. Pat. Nos. 5,359,115 and 5,362,899; the Ellman U.S. Pat. No. 5,288,514; the Still et al. PCT publication WO 94/08051; Chen et al. (1994) JACS 116:2661; Kerr et al. (1993) JACS 115:252; PCT publications WO92/10092, WO93/09668 and WO91/07087; and the Lerner et al. PCT publication WO93/20242.

Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

In other embodiments, the test agents are peptidomimetics of tim-1, tim-4 or fragments thereof. Peptidomimetics are compounds based on, or derived from, peptides and polypeptides. Peptidomimetics that may be used in the present invention typically can be obtained by structural modification of a known analog peptide sequence using unnatural amino acids, conformational restraints, isosteric replacement, and the like. The subject peptidomimetics constitute the continuum of structural space between peptides and non-peptide synthetic structures; analog peptidomimetics may be useful, therefore, in delineating pharmacophores and in helping to translate peptides into nonpeptide compounds with the activity of the parent analog peptides.

Moreover, as is apparent from the present disclosure, mimetopes of the subject tim-1 and tim-4 sequences can be provided. Such peptidomimetics can have such attributes as being non-hydrolyzable (e.g., increased stability against proteases or other physiological conditions which degrade the corresponding peptide), increased specificity and/or potency, and increased cell permeability for intracellular localization of the peptidomimetic. For illustrative purposes, peptide analogs of the present invention can be generated using, for example, benzodiazepines (e.g., see Freidinger et al. in Peptides: Chemistry and Biology, G. R. Marshall ed., ESCOM Publisher: Leiden, Netherlands, 1988), substituted gamma lactam rings (Garvey et al. in *Peptides: Chemistry and Biology*, G. R. Marshall ed., ESCOM Publisher: Leiden, Netherlands, 1988, p 123), C-7 mimics (Huffman et al. in *Peptides: Chemistry and Biology*, G. R. Marshall ed., ESCOM Publisher: Leiden, Netherlands, 1988, p. 105), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), α-aminoalcohols (Gordon et al. (1985) *Biochem Biophys Res Commun* 126: 419; and Dann et al. (1986) *Biochem Biophys Res Commun* 134:71), diaminoketones (Natarajan et al. (1984) *Biochem Biophys Res Commun* 124:141), and methyleneamino-modified (Roark et al. in *Peptides: Chemistry and Biology*, G. R. Marshall ed., ESCOM Publisher: Leiden, Netherlands, 1988, p 134). Also, see generally, Session III: Analytic and synthetic methods, in *Peptides: Chemistry and Biology*, G. R. Marshall ed., ESCOM Publisher: Leiden, Netherlands, 1988).

In addition to a variety of sidechain replacements that can be carried out to generate the subject analog peptidomimetics, the present invention specifically contemplates the use of conformationally restrained mimics of peptide secondary structure. Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides.

In some embodiments, the test agents are preselected for their ability to bind to a tim-1 or a tim-4 polypeptide prior to determining if they can affect the binding between a tim-1 or a tim-4 polypeptide. In one embodiment, test agent may first be selected for its ability to bind a tim-1 or a tim-4 polypeptide. The test agent may be preselected by screening a library of test agents, such as a peptide library or a phage display library.

VI. Methods of Identifying Tim-1 and Tim-4 Variants and Analogs

Another aspect of the invention provides a methods of identifying variant forms of tim-1 or tim-4 polypeptides with altered binding activity, or with altered function. In one aspect, the invention provides methods of identifying tim-4 polypeptides with altered binding properties relative to wild-type tim-4. In one embodiment, tim-4 polypeptides containing truncations at their N- or C-termini, or at both, are tested for binding to a tim-1 polypeptides. Such an approach would allow, for example, to identify a minimal tim-4 fragment which retains its ability to bind to tim-1. The tim-4 fragments may be fused to a second polypeptide, such as an Ig domain or a GST fusion polypeptide for the assays. In addition, mutations, such as but not limited to, those resulting in deletions, insertions, or substitutions at one or more amino acid positions may be introduced into a DNA segment encoding (a) a full-length tim-4 polypeptide or (b) a tim-4 fragment capable of binding to a tim-1 polypeptide, and the ability of the mutant tim-4 fragments are tested to determine if the mutant polypeptide has an altered binding affinity towards a tim-1 polypeptide. In another aspect, the invention provides methods of identifying tim-1 polypeptides with altered binding properties relative to wild-type tim-1, similar to the identification of tim-4 polypeptides with altered binding properties relative to wild-type tim-4.

The generation of tim-4 and tim-1 mutants may achieved, for example, by generating a library of mutant polypeptides through any technique known to one skilled in the art. Techniques for in vitro mutagenesis of cloned genes are known. Examples of protocols for scanning mutations may be found in Gustin et al., Biotechniques 14:22 (1993); Barany, Gene 37:111-23 (1985); Colicelli et al., Mol Gen Genet 199:537-9 (1985); and Prentki et al., Gene 29:303-13 (1984). Methods for site specific mutagenesis can be found in Sambrook et al., Molecular Cloning: A Laboratory Manual, CSH Press 1989, pp. 15.3-15.108; Weiner et al., Gene 126:35-41 (1993); Sayers et al., Biotechniques 13:592-6 (1992); Jones and Winistorfer, Biotechniques 12:528-30 (1992); Barton et al., Nucleic Acids Res 18:7349-55 (1990); Marotti and Tomich, Gene Anal Tech 6:67-70 (1989); and Zhu Anal Biochem 177:120-4 (1989). Amino acid substitutions may be made on the basis of similarity in polarity, charge, solubility, hydrophobicity, hydrophilicity, and/or the amphipathic nature of the residues involved. In other embodiments, the mutation(s) are generated randomly.

Tim-1 or tim-4 polypeptides having altered binding properties refer to polypeptides which have an altered affinity for tim-4 or tim-1, respectively. In some specific embodiments, the mutant polypeptides have the same binding affinity under some physiological conditions as the non-mutant forms but a different affinity under others. For example, a tim-4 polypeptide consisting of (a) tim-4 IgV domain with at least one amino acid substitution; (b) optionally a tim-4 mucin domain; and (c) optionally a human Ig domain or an affinity tag, may be tested for binding to a tim-1 polypeptide. This tim-4 polypeptide might be found to bind to tim-1 with the same binding affinity at 37° C. as the equivalent tim-4 polypeptide not having the mutation, but show a different binding affinity at 35° C. Similarly, the mutant peptide may show a differential activity when another parameter is changed, such as pH or the presence or absence of monovalent or divalent ions.

Another aspect of the invention provides a method of identifying an amino acid residue in tim-4 which contributes to binding of tim-4 to tim-1, the method comprising (a) contacting (i) a polypeptide comprising a tim-4 IgV domain, wherein said tim-4 IgV domain has between one and ten amino acid substitutions relative to a tim-4 IgV domain as set forth in residues 31-133 of SEQ ID NO:3; and (ii) a tim-1 polypeptide, wherein said tim-1 polypeptide is capable of binding to tim-4; (b) detecting formation of a complex between the polypeptide and the tim-1 polypeptide; and (c) comparing the formation of the complex to a suitable control, wherein an amino acid is identified as contributing to binding to tim-1 if the extent of complex formation differs from the suitable control.

In one embodiment, the suitable control comprises the formation of a complex between (i) the tim-1 polypeptide, and (ii) a control polypeptide comprising the amino acid sequence of a tim-4 IgV domain as set forth in SEQ ID NO:3.

In another embodiment, the suitable control comprises a predetermined threshold level. In another embodiment, the tim-1 polypeptide comprises a sequence that is at least 80%, 85%, 90%, 95%, 96%, 97%, 98% or 99% identical or similar to the amino acid sequence of a tim-1 IgV domain as set forth in residues 21-126 of SEQ ID NO:1. In another embodiment, the polypeptide further comprises a tim-4 mucin domain. In a related embodiment, the polypeptide comprises a sequence that is at least 90% identical or similar to the amino acid sequence of a tim-4 mucin domain.

Another aspect of the invention provides a method of identifying an amino acid residue in tim-1 which contributes to binding of tim-1 to tim-4, the method comprising (a) contacting (i) a polypeptide comprising a tim-1 IgV domain, wherein said tim-1 IgV domain has between one and ten amino acid substitutions relative to a tim-1 IgV domain as set forth in residues 21-126 of SEQ ID NO:1; and (ii) a tim-4 polypeptide or fragment thereof, wherein said tim-4 polypeptide or fragment thereof is capable of binding to tim-2; (b) detecting formation of a complex between the polypeptide and the tim-41 polypeptide; and (c) comparing the formation of the complex to a suitable control, wherein an amino acid is identified as contributing to binding to tim-4 if the extent of complex formation differs from the suitable control.

A related aspect of the invention provides a method of determining if a test polypeptide binds to a tim-1 polypeptide, wherein the test polypeptide comprises an amino acid sequence that is at least 90% identical or similar to amino acids 31-133 of SEQ ID NO: 3, the method comprising (a) contacting the test polypeptide with a tim-1 polypeptide; and (b) detecting formation of a complex between the test polypeptide and the tim-1 polypeptide; wherein the test polypeptide is determined to bind to the tim-1 polypeptide if a complex is detected. In one embodiment, the test polypeptide comprises a sequence that is at least 70%, 80%, 90% or 95% identical or similar to a tim-4 IgV domain as set forth in residues 31-133 SEQ ID NO:3 or residues 31-134 of SEQ ID NO: 4. In another embodiment, the test polypeptide comprises a sequence that is at least 70%, 80%, 90% or 95% identical or similar to a tim-4 polypeptide comprising an amino acid sequence selected from the group consisting of SEQ ID NO: 3, SEQ ID NO: 4, SEQ ID NO: 9, SEQ ID NO: 10, SEQ ID NO:11 and SEQ ID NO: 12

In another embodiment, the test polypeptide comprises a polypeptide sequence which facilities its purification, or which confers enhanced stability or activity in vivo, such as an Fc immunoglobulin domain or an affinity tag.

Another aspect of the invention provides a method of determining if a test polypeptide binds to a tim-4 polypeptide, wherein the test polypeptide comprises an amino acid sequence that is at least 90% identical or similar to amino acids 21-126 of SEQ ID NO: 1, the method comprising (a) contacting the test polypeptide with a tim-4 polypeptide; and (b) detecting formation of a complex between the test polypeptide and the tim-4 polypeptide; wherein the test polypeptide is determined to bind to the tim-4 polypeptide if a complex is detected. In one embodiment, the test polypeptide comprises a sequence that is at least 70%, 80%, 90% or 95% identical or similar to a tim-1 IgV domain as set forth in residues 21-126 SEQ ID NO:1 or residues 21-129 of SEQ ID NO:2. In another embodiment, the test polypeptide comprises a which facilities its purification, or which confers enhanced stability or activity in vivo, such as an Fc immunoglobulin domain or an affinity tag.

In one embodiment of the methods described herein for determining if a test polypeptide binds to a tim-1 or to a tim-4 polypeptide, the test polypeptide is a peptidomimetic of tim-1 or tim-4, such as those described in the previous section. A computer program useful in designing potentially bioactive peptidomimetics is described in U.S. Pat. No. 5,331,573, the disclosure of which is incorporated by reference herein.

VII. Formulations

The therapeutic agents described herein may be formulated into pharmaceutical compositions. Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, by aerosol, intravenous, oral or topical route. The administration may comprise intralesional, intraperitoneal, subcutaneous, intramuscular or intravenous injection; infusion; liposome-mediated delivery; topical, intrathecal, gingival pocket, per rectum, intrabronchial, nasal, transmucosal, intestinal, oral, ocular or otic delivery.

An exemplary composition of the invention comprises an RNAi mixed with a delivery system, such as a liposome system, and optionally including an acceptable excipient. In a preferred embodiment, the composition is formulated for injection.

Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. in addition, detergents may be used to facilitate permeation. Transmucosal administration may be through nasal sprays or using suppositories. For topical administration, the oligomers of the invention are formulated into ointments, salves, gels, or creams as generally known in the art. A wash solution can be used locally to treat an injury or inflammation to accelerate healing.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

For therapies involving the administration of nucleic acids, the oligomers of the invention can be formulated for a variety of modes of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, intranodal, and subcutaneous for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as generally known in the art.

Toxicity and therapeutic efficacy of the agents and compositions of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic induces are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In one embodiment of the methods described herein, the effective amount of the agent is between about 1 mg and about 50 mg per kg body weight of the subject. In one embodiment, the effective amount of the agent is between about 2 mg and about 40 mg per kg body weight of the subject. In one embodiment, the effective amount of the agent is between about 3 mg and about 30 mg per kg body weight of the subject. In one embodiment, the effective amount of the agent is between about 4 mg and about 20 mg per kg body weight of the subject. In one embodiment, the effective amount of the agent is between about 5 mg and about 10 mg per kg body weight of the subject.

In one embodiment of the methods described herein, the agent is administered at least once per day. In one embodiment, the agent is administered daily. In one embodiment, the agent is administered every other day. In one embodiment, the agent is administered every 6 to 8 days. In one embodiment, the agent is administered weekly.

As for the amount of the compound and/or agent for administration to the subject, one skilled in the art would know how to determine the appropriate amount. As used herein, a dose or amount would be one in sufficient quantities to either inhibit the disorder, treat the disorder, treat the subject or prevent the subject from becoming afflicted with the disorder. This amount may be considered an effective amount. A person of ordinary skill in the art can perform simple titration experiments to determine what amount is required to treat the subject. The dose of the composition of the invention will vary depending on the subject and upon the particular route of administration used. In one embodiment, the dosage can range from about 0.1 to about 100,000 ug/kg body weight of the subject. Based upon the composition, the dose can be delivered continuously, such as by continuous pump, or at periodic intervals. For example, on one or more separate occasions. Desired time intervals of multiple doses of a particular composition can be determined without undue experimentation by one skilled in the art.

The effective amount may be based upon, among other things, the size of the compound, the biodegradability of the compound, the bioactivity of the compound and the bioavailability of the compound. If the compound does not degrade quickly, is bioavailable and highly active, a smaller amount will be required to be effective. The effective amount will be known to one of skill in the art; it will also be dependent upon the form of the compound, the size of the compound and the bioactivity of the compound. One of skill in the art could routinely perform empirical activity tests for a compound to determine the bioactivity in bioassays and thus determine the effective amount. In one embodiment of the above methods, the effective amount of the compound comprises from about 1.0 ng/kg to about 100 mg/kg body weight of the subject. In another embodiment of the above methods, the effective amount of the compound comprises from about 100 ng/kg to about 50 mg/kg body weight of the subject. In another embodiment of the above methods, the effective amount of the compound comprises from about 1 ug/kg to about 10 mg/kg body weight of the subject. In another embodiment of the above methods, the effective amount of the compound comprises from about 100 ug/kg to about 1 mg/kg body weight of the subject.

As for when the compound, compositions and/or agent is to be administered, one skilled in the art can determine when to administer such compound and/or agent. The administration may be constant for a certain period of time or periodic and at specific intervals. The compound may be delivered hourly, daily, weekly, monthly, yearly (e.g. in a time release form) or as a one time delivery. The delivery may be continuous delivery for a period of time, e.g. intravenous delivery. In one embodiment of the methods described herein, the agent is administered at least once per day. In one embodiment of the methods described herein, the agent is administered daily. In one embodiment of the methods described herein, the agent is administered every other day. In one embodiment of the methods described herein, the agent is administered every 6 to 8 days. In one embodiment of the methods described herein, the agent is administered weekly.

In some embodiments of the methods described herein in which an agent comprising a polypeptide is administered to a subject, the polypeptide is administered to the subject by administering a gene encoding such polypeptide. Expression constructs of the therapeutic polypeptides (such as a polypeptide comprising a wildtype or mutant tim-4 IgV domain) may be administered in any biologically effective carrier, e.g. any formulation or composition capable of effectively transfecting cells in vivo with a recombinant fusion gene. Approaches include insertion of the subject fusion gene in viral vectors including recombinant retroviruses, adenovirus, adeno-associated virus, and herpes simplex virus-1, or recombinant bacterial or eukaryotic plasmids. Viral vectors can be used to transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or CaPO$_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) Blood 76:271). Thus, recombinant retrovirus can be constructed in which part of the retroviral coding sequence (gag, pol, env) has been replaced by nucleic acid encoding a CKI polypeptide, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis, et al. (1985) *Science* 230:1395-1; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging polypeptides on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env polypeptide (Roux et al. (1989) PNAS 86:9079-9083; Julan et al. (1992) J. Gen Virol 73:3251-3255; and Goud et al. (1983) Virology 163:251-254); or coupling cell surface ligands to the viral env polypeptides (Neda et al. (1991) J Biol Chem 266:14143-14146). Coupling can be in the form of the chemical cross-linking with a polypeptide or other variety (e.g. lactose to convert the env polypeptide to an asialoglycopolypeptide), as well as by generating fusion polypeptides (e.g. single-chain antibody/env fusion polypeptides). This technique, while useful to limit or otherwise direct the infection to certain tissue types, and can also be used to convert an ecotropic vector in to an amphotropic vector.

In addition to viral transfer methods, such as those illustrated above, non-viral methods can also be employed to cause expression of a the subject polypeptides in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the gene by the targeted cell. Exemplary gene delivery systems of this type include liposomal derived systems, poly-lysine conjugates, and artificial viral envelopes.

In a representative embodiment, a gene encoding one of the subject polypeptides can be entrapped in liposomes bearing positive charges on their surface (e.g., lipofectins) and (optionally) which are tagged with antibodies against cell surface antigens of the target tissue (Mizuno et al. (1992) No Shinkei Geka 20:547-551; PCT publication WO91/06309; Japanese patent application 1047381; and European patent publication EP-A-43075). For example, lipofection of neuroglioma cells can be carried out using liposomes tagged with monoclonal antibodies against glioma-associated antigen (Mizuno et al. (1992) Neurol. Med. Chir. 32:873-876).

In clinical settings, the gene delivery systems can be introduced into a patient by any of a number of methods, each of which is familiar in the art. For instance, a pharmaceutical preparation of the gene delivery system can be introduced systemically, e.g. by intravenous injection, and specific transduction of the target cells occurs predominantly from specificity of transfection provided by the gene delivery vehicle, cell-type or tissue-type expression due to the transcriptional regulatory sequences controlling expression of the gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3054-3057).

Description of Sequence Listings

SEQ ID NO: 1 is Tim-1Human Polypeptide. This sequence is listed as Genbank Deposit No. NP_036338.

SEQ ID NO: 2 is Tim-1 Mouse Polypeptide. This sequence is listed as Genbank Deposit No. NP_599009.

SEQ ID NO: 3 is Tim-4 Human Polypeptide Variant #1.

SEQ ID NO: 4 is Tim-4 Mouse Polypeptide. This sequence is listed as Genbank Deposit No. NP_848874.

SEQ ID NO: 5 is Tim-1Human Nucleic Acid. This sequence is listed as Genbank Deposit No. NM_012206.

SEQ ID NO: 6 is Tim-1 Mouse Nucleic Acid. This sequence is listed as Genbank Deposit No. NM_134248.

SEQ ID NO: 7 is Tim-4 Human Nucleic Acid Variant #1.

SEQ ID NO:8 is Tim-4 Mouse Nucleic Acid. This sequence is listed as Genbank Deposit No. NM_178759.

SEQ ID NO:9 is a soluble form of mouse tim-4 lacking exons 6 and 7.

SEQ ID NO:10 is an isoform of mouse tim-4 lacking exons 6. Deletion of exon 6 results in a frameshift following exon 5.
SEQ ID NO:11 is a soluble form of human tim-4, similar to the mouse soluble form of tim-4 lacking the exons 6 and 7.
SEQ ID NO:12 is a Tim-4 Mouse Polypeptide Variant.
SEQ ID NO:13 is Tim-2 mouse polypeptide (NP_599010).

Exemplification

The invention now being generally described, it will be more readily understood by reference to the following examples, which are included merely for purposes of illustration of certain aspects and embodiments of the present invention, and are not intended to limit the invention, as one skilled in the art would recognize from the teachings hereinabove and the following examples, that other DNA microarrays, cell types, agents, constructs, or data analysis methods, all without limitation, can be employed, without departing from the scope of the invention as claimed.

The contents of any patents, patent applications, patent publications, or scientific articles referenced anywhere in this application are herein incorporated in their entirety.

Summary of Experimental Section

The Examples described herein demonstrate that Tim-2 is preferentially upregulated on Th2 cells. In order to address the functional role of Tim-2, a monoclonal antibody directed at tim-2 and a fusion polypeptide comprising domains of Tim-2 and an Fc immunoglobin chain were generated. The examples show that administration of Tim-2Ig induces T cell activation and the production of Th2 cytokines. Moreover, when Tim-2Ig is administered during the induction of a Th1 mediated disease such as experimental autoimmune encephalomyelitis (EAE), clinical signs of disease are significantly reduced. When administered during the induction of peripheral tolerance Tim-2Ig is able to promote transplantation tolerance. Taken together, these data suggest that Tim-2 is expressed on Th2 differentiated cells, and that blocking the interaction between Tim-2 and its ligand expands a Th2 response, which delays the onset and severity of the autoimmune disease EAE, and enhances transplantation tolerance. Further, the examples show that administration of a Tim1/Fc fusion polypeptides facilitates allograft tolerance in a mouse islet transplantation model.

The examples also demonstrate that Tim-4 is the natural ligand for Tim-1, and show that Tim-4 expression is limited to the immune compartment, within which expression of Tim-4 is restricted to macrophages and dendritic cells (DCs). Using soluble Ig fusion polypeptides, Tim-4 was found to specifically bind to Tim-1 and that this interaction is inhibited by an anti-Tim-1 antibody. Furthermore, in vivo administration of Tim-1-Ig resulted in the preferential expansion of $T_H2$ cells, while Tim-4-Ig stimulated T cell proliferation. These examples support the model that the Tim-4-Tim-1 interaction delivers a signal necessary for expansion of T cells.

Experimental Procedures

Antibodies, Mice, and Ig Fusion Polypeptides

All animal experiments were done in compliance with the approval of the Harvard Medical Area Standing Committee on Animals (protocol 696). All mice were purchased from Jackson Laboratories. Antibodies used in FACS analysis from BD Pharmingen were: FITC-labeled anti-mouse: B220, CD3ε, CD11b, CD11c, and CD4; PE-labeled anti-mouse: IFN-γ, IL-4, IL-10; streptavidin-PE, and specific isotype controls. Secondary PE-labeled detection reagents goat F(ab')2 anti-human IgG, goat anti-rat Ig (H+L), and goat anti-mouse IgG2a were from Southern Biotechnology. Anti-HA-biotin (clone 12CA5) was from Roche. Anti-Tim-3 (2C12) has been previously described (Monney et al. (2002). Nature 415, 536-541), and anti-Tim-1 (3B3) has recently been generated. All Ig fusion polypeptides were made by Chimerigen, fusing the extracellular regions of the polypeptides of interest to a huIgG1 Fc tail.

$T_H1$ and $T_H2$ Cell Lines and Clones

AE7, a pigeon cytochrome c specific $T_H1$ clone, and D10.G4, a conalbumin A specific $T_H2$ clone, were maintained in a rest-stimulation protocol as previously described (Sabatos et al. (2003). Nat Immunol 4, 1102-1110). DO11.10 TcR Tg $T_H1$ and $T_H2$ cell lines were generated in vitro as previously described and successful polarization was verified after each round of restimulation by intracellular cytokine staining (Monney et al. (2002). Nature 415, 536-541).

Transfectants

Tim-4 and Tim-1 transfectants were made in the pDisplay vector (Invitrogen). Tim-4 was amplified from cloned cDNA using the following primers: 5'-AGTCA-GATCTGGGTTTTTGGGCCAGCCGGTG-3' (BglII site in italics) (SEQ ID NO: 15) and 5'-AGTCCTGCAGTCA-GAGAGTGAAGATCCCG-3' (PstI site in italics) (SEQ ID NO: 16). The amplified product lacked the Tim-4 signal sequence to avoid cleavage of the vector's N-terminal HA tag and take advantage of the vector's signal sequence. The Tim-4-pDisplay construct was transfected using GeneJuice (Novagen) into CHO or HEK293 cells, and stable transfectants were selected with 1.5 µg/ml G-418 (Gibco). Tim-1 was amplified from cloned cDNA using the following primers: 5'-AGTCAGATCTATGAATCAGATTCAAGTCTTC-3' (BglII site in italics) (SEQ ID NO: 17) and 5'-AGTCCTG-CAGAGGTCTATCTTCAACAATG-3' (PstI site in italics) (SEQ ID NO: 18), and the Tim-1-pDisplay construct was transfected into HEK293 cells as above. CHO-Tim-1 cells were made by cotransfecting CHO-K1 cells with pEF6 containing murine Tim-1 cDNA and a puromycin-resistance gene using FuGENE (Roche). Cells were selected with puromycin and blasticidin and sorted by flow cytometry for Tim-1 expression using polyclonal rat anti-Tim-1 serum, and then subcloned. CHO-Tim-3 transfectants have been previously described (Monney et al. (2002). Nature 415, 536-541).

Cell Separation and Stimulation

CD11b+, CD11c+, and B220+ cells were purified from spleens and lymph nodes through positive selection by MACS Sort magnetic beads in MACS LS Separation columns (Miltenyi Biotec), and CD3+ T cells were purified by negative selection columns (R&D Systems). The purity of cells was checked by flow cytometry.

Total splenocytes or purified CD11b+ or CD11c+ populations were stimulated with 1 ng/ml LPS (Sigma) and 10 ng/ml IFN-γ (R&D) for 42-48 h. To activate T cells, total splenocytes or purified CD3+ T cells were stimulated 42-48 h with 1 µg/ml concanavalin A (ConA) (Sigma). Purified CD3+ T cells were also stimulated 42-48 h in 24-well plates coated with 0.5 µg/well anti-CD3 (clone 145-2C11, BD Pharmingen) and 0.5 µg/well anti-CD28 (clone 37.51, BD Pharmingen) for 2 h at 37° C. All stimulations were performed in the complete medium, lacking rIL-2, previously described (Sabatos et al. (2003). Nat Immunol 4, 1102-1110).

DC Generation

For in vitro DC generation, bone marrow cells were flushed from CB6F1 femurs, RBCs were lysed, and remaining cells were plated at $10^6$/ml with 20 ng/ml GM-CSF or 200 ng/ml Flt3L. After 5 d for GM-CSF stimulation or 8 d for Flt3L stimulation, 40 ng/ml LPS was added to some cultures for 12-14 h. Cells were harvested after a total of 6 d for GM-CSF and 9 d for Flt3L. Mature myeloid cells were separated from GM-CSF-induced DCs by positive selection for CD86+ cells using MACS magnetic beads as above. Flt3L-induced cells were depleted of granulocytes by MACS negative selection with Gr-1 antibody (resulting in a mainly CD11c+ population). Some Flt3L-induced DCs were depleted of the B220+ plasmacytoid fraction by MACS.

For in vivo DC generation, CB6F1 mice were injected subcutaneously with 2×10⁶ Flt3L-secreting CMS5 cells (generous gift of Devin Turner). Spleens were harvested after 9 d, the total CD11c+ population was obtained by granulocyte depletion as above, and DC types were separated by cell surface markers using MACS positive selection.

Quantitative TaqMan RT-PCR

Total RNA was extracted from cells using the Trizol method (Invitrogen). RNA was then subjected to digestion with 0.6 units/μg DNAse 1 (Qiagen) for 15 minutes at room temperature, using an RNeasy Mini Kit (Qiagen). Reverse transcription was performed on 1-2 μg of digested RNA using ABI Prism Taqman® reverse transcription reagents (with both random hexamers and oligo dT as primers). The expression levels of Tim-4 and internal reference GAPDH were simultaneously measured by multiplex PCR using probes labeled with 6-carboxyfluorescein (FAM) or VIC® (Applied Biosystems) respectively, and with TAMRA as a quencher. Taqman primers/probe were designed using Primer Express v1.0 software (Applied Biosystems) to cover the Tim-4 exon 3: exon 4 junction. The primers were: 5'-CACCTGGCTCCT-TCTCACAA-3' (SEQ ID NO: 19) and 5'-TGATTGGATG-CAGGCAGAGTT-3' (SEQ ID NO: 20), and the probe was 6FAM-5'-AAAAGGGTCCGCCATCACTACAGAATCAG-3'-TAMRA (SEQ ID NO: 21). The GAPDH primer and probe set was purchased from Applied Biosystems. PCRs were performed using Taqman® Universal PCR Master Mix (Applied Biosystems) and the ABI PRISM 7700 Sequence Detection System. A comparative threshold cycle (CT) was used to determine gene expression. For each sample, the Tim-4 CT value was normalized using the formula $\Delta C_T = C_{T\ TIM-4} - C_{T\ GAPDH}$. To determine relative expression, the mean ΔCT was determined, and relative Tim-4 expression was calculated using the expression $2^{-\Delta CT}$.

Blocking with Anti-Tim-1

Cells expressing Tim-4 were stained with 5 μg/ml Tim-1-Ig that was pre-incubated 1 h on ice with 350 μg/ml anti-Tim-1 or anti-Tim-3. Anti-mouse IgG2a-PE was used for detection. Cells expressing Tim-1 were incubated 1 h on ice with 350 μg/ml anti-Tim-1 or anti-Tim-3 before 1 μg/ml Tim-4-Ig was added to the mix and detected with anti-huIgG-PE.

Proliferation Assays and ELISAs

Female SJL/J mice (6-12 weeks old) were injected subcutaneously in each flank with 50-100 μg PLP 139-151 peptide (HSLGKWLGHPDKF) (SEQ ID NO: 22) (Quality Controlled Biochemicals) emulsified in complete Freund's adjuvant (CFA) (Difco). Mice were injected intraperitoneally (i.p.) every other day (beginning the same day as immunization, day 0, and continuing through day 8) with either 100 μg Tim-1-Ig or Tim-4-Ig, 100 μg control hIgG1 (Sigma), or PBS (in same volume as Ig fusion polypeptide). Mice were sacrificed on day 10, and spleens were removed. Cells were plated at 5×10⁵ cells/well in round bottom 96 well plates (BD Falcon) in complete medium with PLP 139-151 added at 0-100 μg/ml. After 48 h, culture supernatants were removed for cytokine ELISAs, and plates were pulsed with 1 μCi ³[H] thymidine/well for 16-18 h. The incorporated radiolabeled thymidine was measured utilizing a Beta Plate scintillation counter (Perkin Elmer Wallac Inc). The data are presented as mean counts per minute (c.p.m.) in triplicate wells. Cytokine production was measured by quantitative capture ELISA as previously described (Sabatos et al. (2003). Nat Immunol 4, 1102-1110).

To determine which cells were proliferating, total splenocytes were separated into B220+, CD11b+, and CD3+ populations as above. Cells were then recombined, using 10⁵ T cells with 2×10⁵ of each type of APC in a total volume of 200 μl/well in triplicate wells. Proliferation was measured after 48 h as above.

Costimulation Assays

CD3+ T cells were purified from total lymph node cells and were then plated on tissue culture dishes for 1 h at 37° C. to remove any residual APCs. Non-adherent cells were removed and 10⁵ cells were seeded per well on flat-bottom 96-well plates coated with antibodies or fusion polypeptides at concentrations indicated in the text. Plates were coated at 37° C. for 2 h and then washed 2-3 times with PBS. After 48 h, plates were pulsed with 1 μCi ³[H]thymidine/well for 16-18 h and proliferation of T cells was determined by ³[H]thymidine incorporation in triplicate wells. Statistical significance was determined by a Mann-Whitney test, using data from all repeat experiments.

EXAMPLE 1

Identification of Tim-2 Expression in Th2 Cells

Figure 1A:
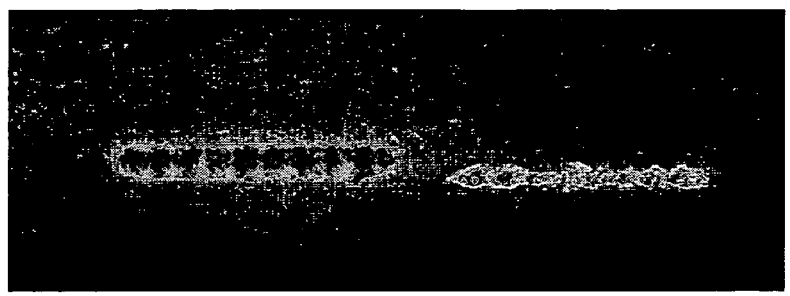
FIG. 1 shows that Tim-2 mRNA is preferentially expressed in Th2 cells. (A) cDNA generated from Th1 (AE7) and Th2 (D10G4) clones were subjected to RT-PCR using Tim-2 and Tim-3 primers. Products were resolved on a 1.2% agarose gel. (B) D011.10 TCR transgenic CD4 T cells were stimulated with OVA 323-339 in the presence of Th1 or Th2 polarizing conditions. RNA was extracted at the end of each stimulation round and cDNA generated. CDNA was subjected to cycle-sample PCR using specific Tim-2 primers. Products were resolved on a 1.5% agarose gel.
Figure 1A:
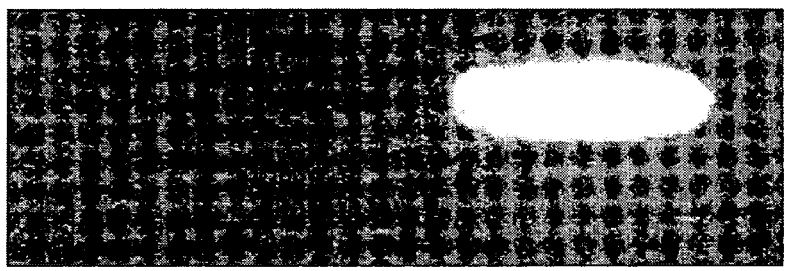
Figure 1B:
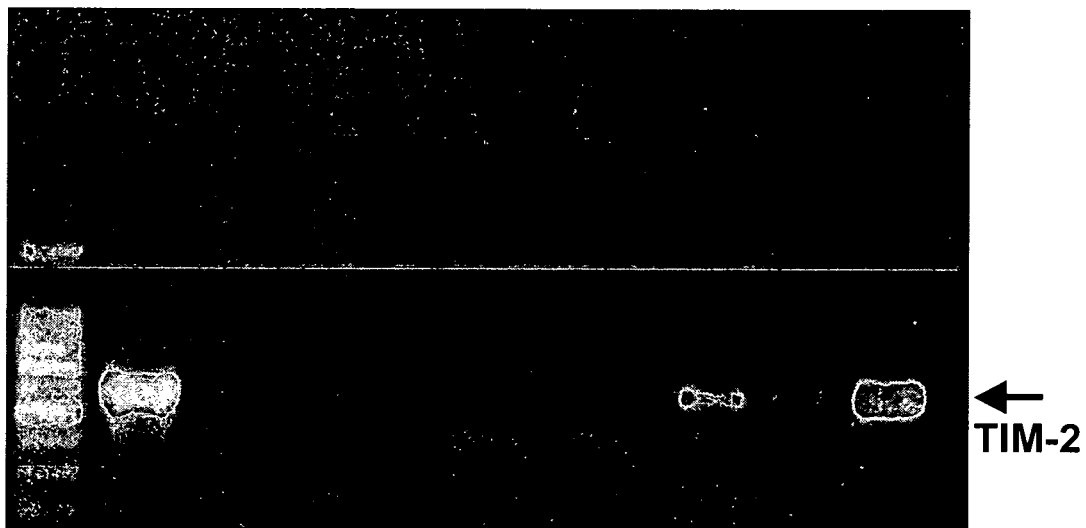

In order to determine the expression of Tim-2 at the RNA level applicants utilized cycle sample semi-quantitative PCR. Tim-2 was expressed in unstimulated Th2 cells clones and not in Th1 (FIG. 1A). The level of Tim-2 message increased upon polarization of DO11.10 CD4+ T cells toward a Th2 phenotype (FIG. 1B). In contrast, the amount of Tim-2 message was undetectable to low in cells polarized down the Th1 pathway (FIG. 1B). These data suggest that Tim-2 is differentially expressed on Th2 cells rather than Th1 cells.

EXAMPLE 2

Construction of Tim-1Ig and Tim-2Ig Fusion Polypeptides

To identify potential ligands of Tim-1 and Tim-2 and to address the functional in vivo relationship between Tim-1 and Tim-2 and their ligand(s) applicants constructed Tim-1Ig and Tim-2Ig fusion polypeptides. In each case, the cDNA encoding the extracellular IgV and mucin domain was fused to the cDNA encoding the human IgG1 Fc tail. The Tim-2 construct was stably transfected into NS.1 cells, and the Tim-1 construct was stably transfected into CHO cells. The fusion polypeptides were purified from the resultant supernatant by column chromatography.

EXAMPLE 3

Expression of Tim-1 and Tim-2 Ligand on Activated Antigen Presenting Cells

Figure 2A:
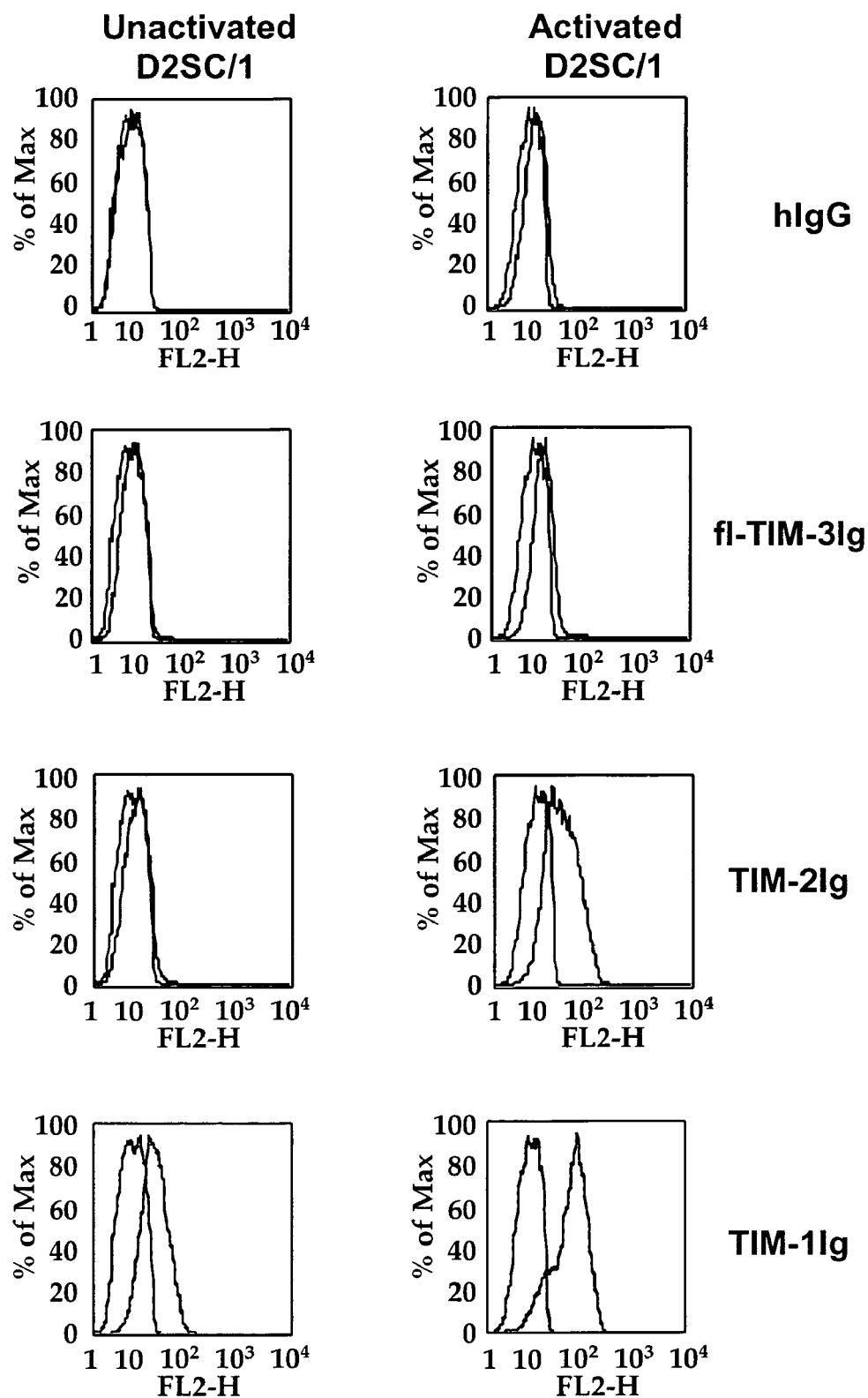
FIG. 2 shows that Tim-2 Ligand is expressed on activated APCs. Dendritic cell line, D2SC/1, and macrophage cell line, RAW 264, were incubated with or without 20 ng/mL LPS and 5 ng/mL IFNγ. 48 hours post-activation, cells were harvested and stained with either biotinylated Tim-2Ig, biotinylated Tim-1Ig, biotinylated Tim-3Ig or biotinylated hIgG and streptavidin-PE as a secondary detection reagent. Cells were analyzed by flow cytometry.
Figure 2B:
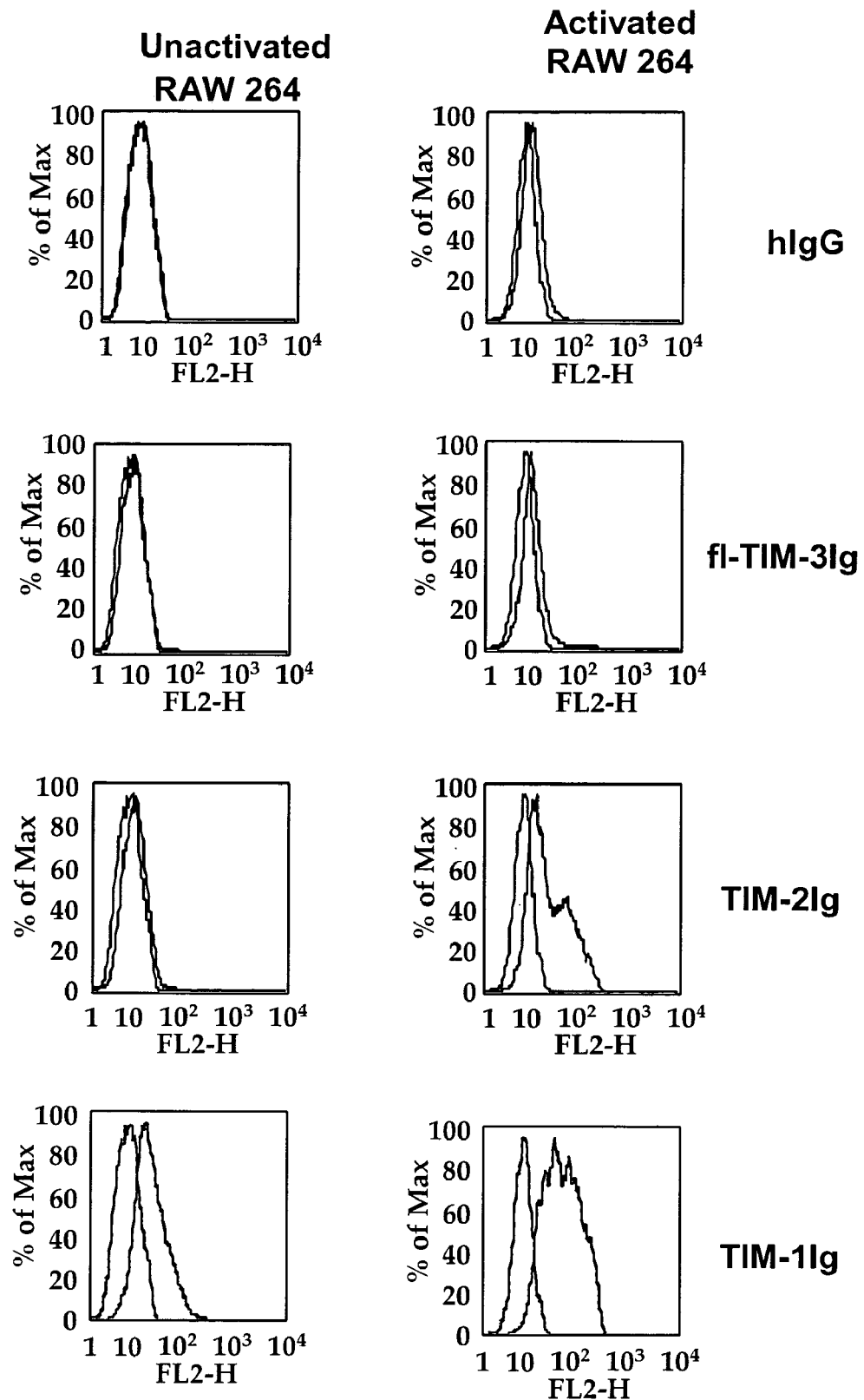

In order to investigate the role of Tim-1 and Tim-2, applicants utilized the Tim-2 fusion polypeptide to identify cell populations expressing the Tim-2 ligand. Various cell lines were stained with both the Tim-1Ig and Tim-2Ig fusion polypeptides. Both unactivated dendritic cells, and macrophages demonstrated low expression of Tim-1 ligand(s). Interestingly, no quiescent populations expressed the Tim-2 ligand. However, when activated with LPS and interferon gamma (IFNγ), dendritic and macrophage cell lines upregulated the expression of the Tim-1 Ligand and induced the expression of Tim-2 ligand (FIGS. 2A and 2B). The increase in expression of Tim-1 and Tim-2 ligands was concurrent with the upregulation of MHC class II, and B7-1 and B7-2 expression on these cellular subsets. All purified T cell populations examined, whether naïve or specifically activated, stained negatively for both the Tim-1 and Tim-2 ligand. Taken together, this data indicates that the Tim-1 and Tim-2 ligand(s) is expressed on activated dendritic cells and macrophages suggesting that the interaction involves a T cell and activated antigen-presenting cell.

EXAMPLE 4

Figure 3:
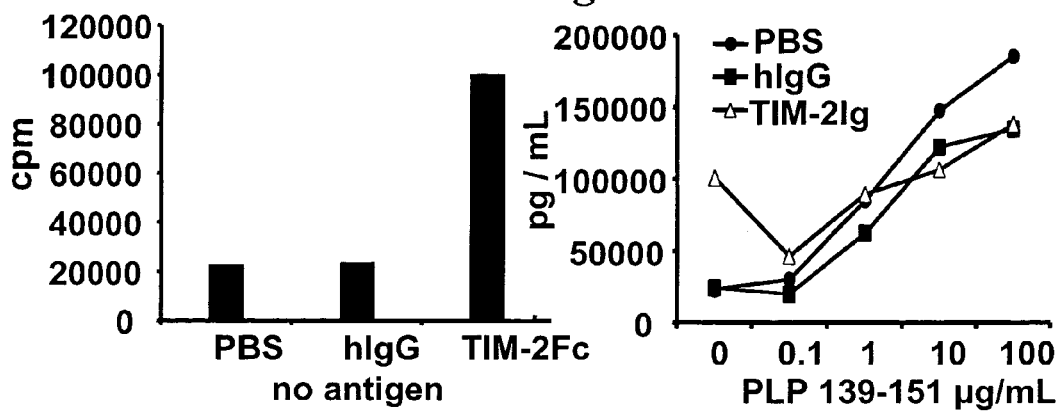
FIG. 3 Administration of Tim-2Ig induces hyperproliferation and the induction of Th2 cytokines SJL mice were immunized with PLP 139-151 and treated with either Tim-2Ig, or hIgG or PBS as controls. Organs were harvested 10 days post-immunization and assessed for proliferation and cytokine production. Tim-2Ig (open triangles); PBS (closed circles); hIgG (closed squares). (A) Whole spleen cells were cultured in the absence of antigen for 48 hours. Proliferation was assessed by the incorporation of $H^3$-thymidine. (B) Whole spleen cells were cultured with increasing concentrations of PLP 139-151 peptide for 48 hours. Proliferation was measured by $H^3$-thymidine incorporation. (C) Supernatants were collected from cultures described in 3(A) and (B), and IL-2, IFNγ, IL-4 and IL-10 expression assessed by ELISA
Figure 3:
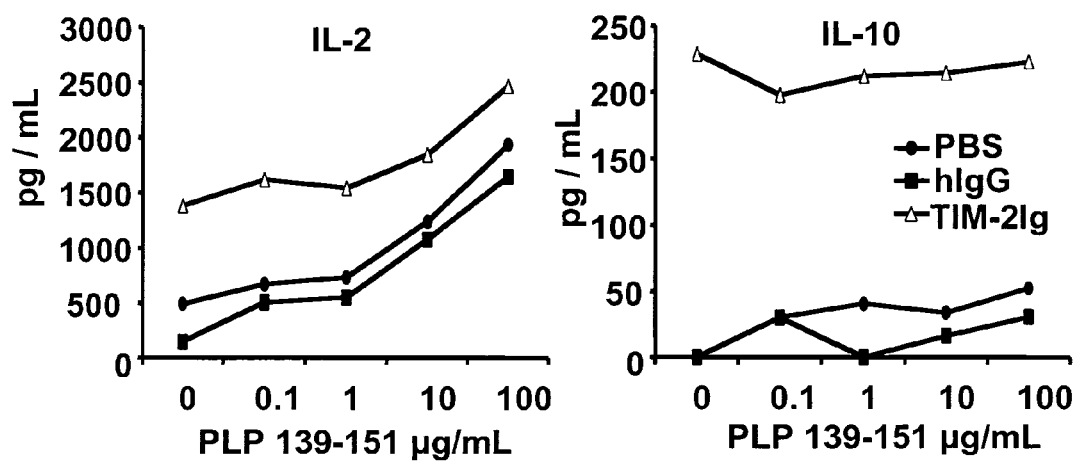
Figure 3:
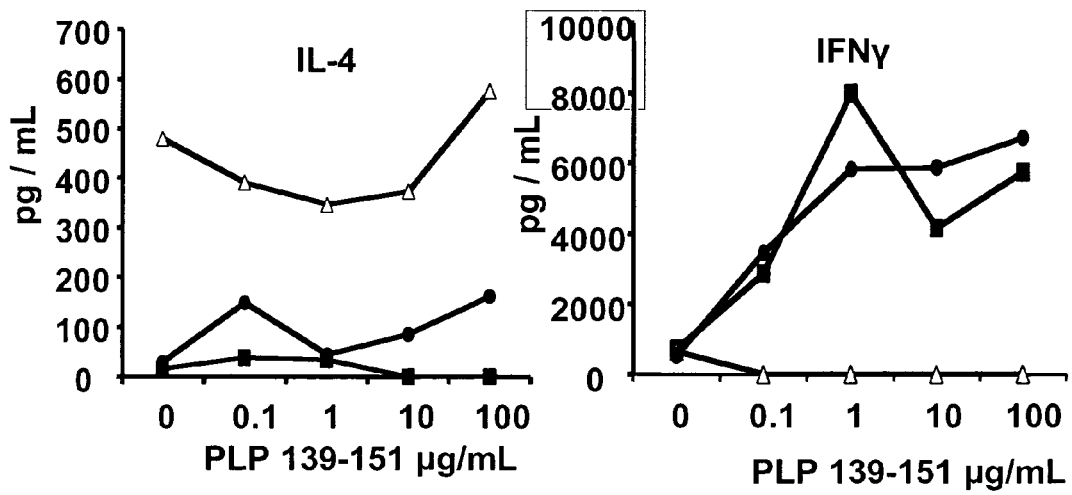
Figure 4:
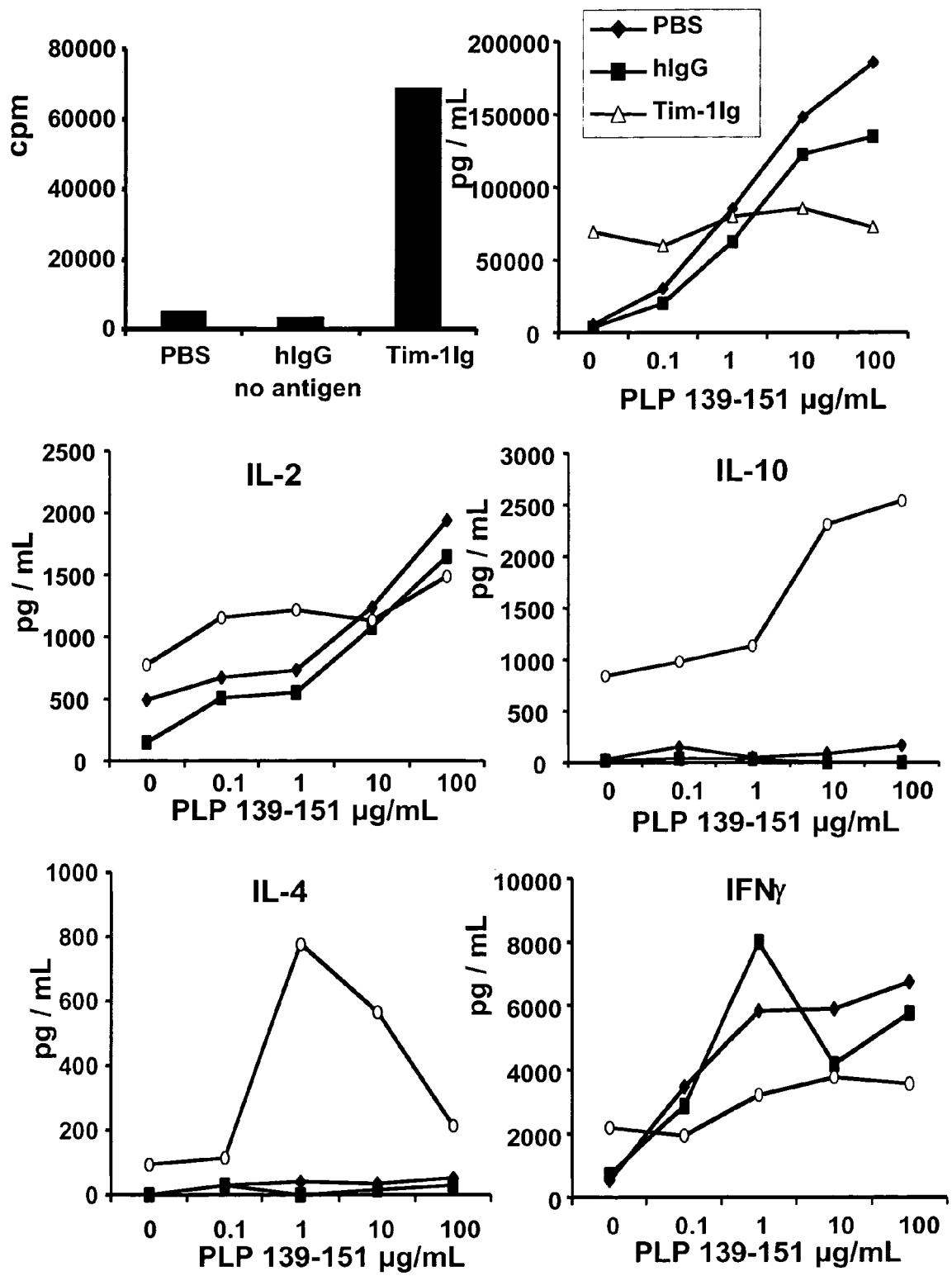
FIG. 4 shows that administration of Tim-1Ig induces hyperproliferation and the induction of Th2 cytokines SJL mice were immunized with PLP 139-151 and treated with either Tim-1Ig, or hIgG or PBS as controls. Organs were harvested 10 days post-immunization and assessed for proliferation and cytokine production. Tim-1Ig (open circles); PBS (closed diamonds); hIgG (closed squares). (A) Whole spleen cells were cultured in the absence of antigen for 48 hours. Proliferation was assessed by the incorporation of $H^3$-thymidine. (B) Whole spleen cells were cultured with increasing concentrations of PLP 139-151 peptide for 48 hours. Proliferation was measured by $H^3$-thymidine incorporation. (C) Supernatants were collected from cultures described in 4(A) and (B), and IL-2, IFNγ, IL-4 and IL-10 expression assessed by ELISA

Induction by Tim-1 and Tim-2 Fusion Polypeptides of T Cell Proliferation and Production of Th2 Cytokines Since Tim-1 and Tim-2 are expressed on Th2 cells, applicants were interested in the role of these molecules within an in vivo immune response. In order to address this, SJL/J mice were immunized with PLP 139-151 in CFA and administered with the Tim-1 g, Tim-2Ig, human IgG or PBS (diluent control). Spleens and lymph nodes were harvested and re-stimulated in vitro to examine the proliferative response and cytokine profiles in the presence of the fusion polypeptide. Splenocytes from the control mice demonstrated a dose-dependent increase in proliferation to PLP 139-151 (FIGS. 3B and 4B). In contrast, the mice treated with either the Tim-1Ig or Tim-2Ig demonstrated a significantly higher basal proliferative response in the absence of antigen (FIGS. 3A and 4A) and demonstrated a shallow dose-dependent increase in proliferation in the presence of PLP 139-151 (FIGS. 3B and 4B). These data suggest that treatment with Tim-1 μg or Tim-2Ig results in the hyperactivation of cells in vivo, such that they continue to proliferate in the absence of antigen in vitro.

Supernatants from these experiments were analyzed 48 hours post restimulation by ELISA for the production of IL-2, IFNγ, IL-4 and IL-10. Whole spleen cells from Tim-1Ig and Tim-2Ig treated mice secreted high amounts of IL-2 consistent with the high basal proliferation observed (FIGS. 3C and 4C). Interestingly, high quantities of IL-4 and IL-10, and little to no IFNγ were also detected in the supernatants from both Tim-1Ig and Tim-2Ig treated mice (FIGS. 3C and 4C). Cells from both the hIgG and PBS treated mice demonstrated a Th1 profile with expression of IL-2 and IFNγ (FIGS. 3C and 4C) In the absence of antigen no detectable levels of cytokines were present in the supernatants. Cells from the Tim-1Ig and Tim-2Ig treated mice demonstrated IL-2 secretion, and low levels of IL-4 and IL-10, although these were markedly increased upon antigenic re-stimulation (FIGS. 3C and 4C). In comparison, cells from control mice demonstrated little to no IL-2 and no detectable IFNγ in the absence of antigen (FIGS. 3C and 4C). Taken together, these results suggest that Tim-1Ig and Tim-2Ig are able to generate the expansion of a Th2 type T cells and cytokines. Moreover, the administration of these two fusion polypeptides generates a Th2 response in a heavily biased Th1 animal model.

Purification of broad antigen presenting cell populations and T cells from the spleens and lymph nodes of Tim-2Ig, hIgG or PBS mice demonstrated that no cell subset (T, B, macrophage or DC) was responsible for the high basal level of proliferation in the absence of antigen alone. Moreover, neither cell subset was responsible for cytokine profiles observed in the absence of antigen. The background proliferative response observed in cells from Tim-2Ig treated mice could be reconstituted with Tim-2Ig T cells in the presence of antigen presenting cells from either Tim-2Ig treated animals or from the control animals. Incubating APC populations from the Tim-2Ig treated mice with T cells from the control mice did not produce high basal proliferative responses indicating that the APC were not responsible for the high proliferative background observed. Furthermore, cytokine production was only detected when T cells were cultured with antigen presenting cells suggesting that the proliferation and Th2 cytokine production observed in cells from TIM-2Ig treated mice is dependent on an interaction between T cells and APCs.

EXAMPLE 5

Figure 5:
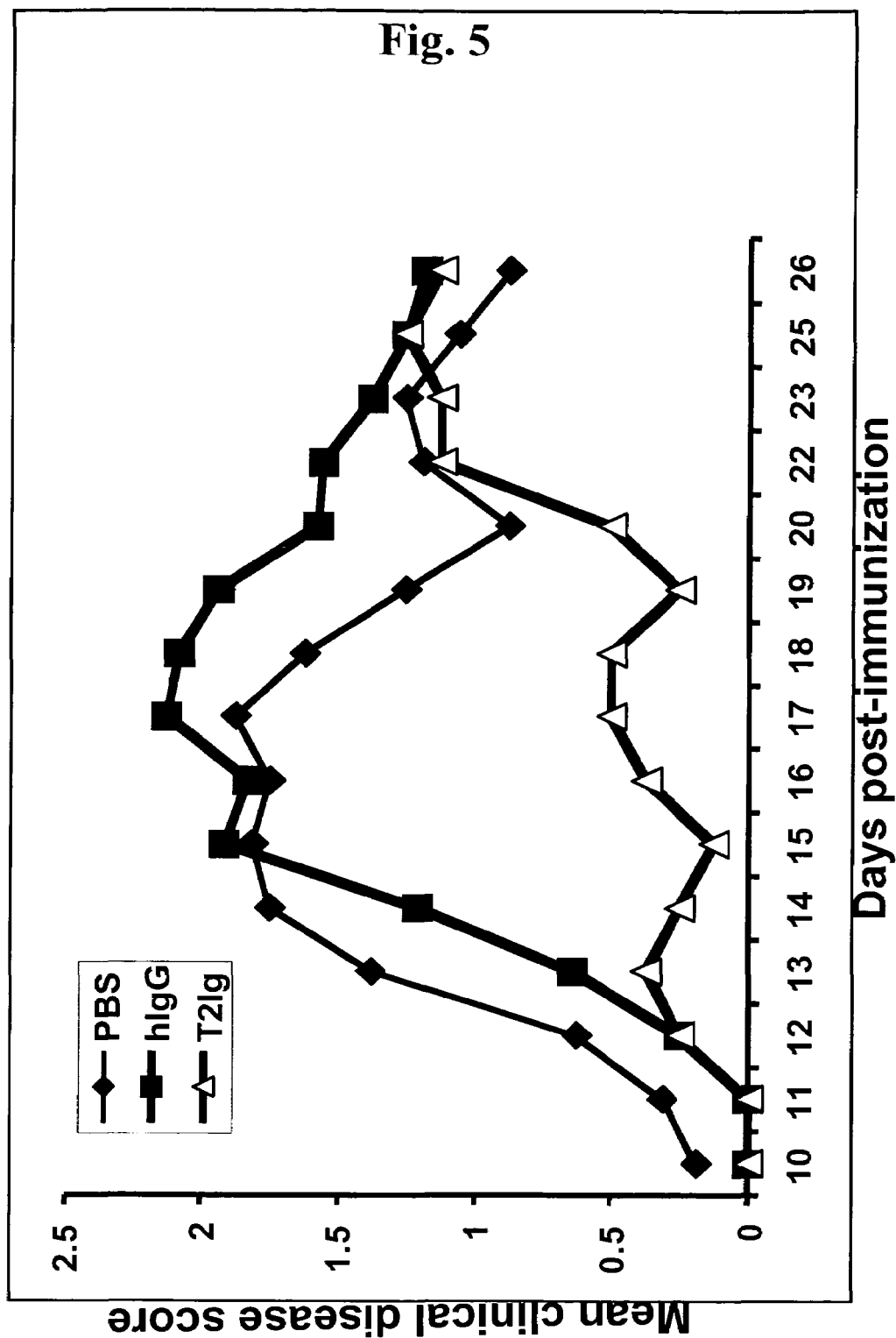
FIG. 5 shows that administration of Tim-2Ig during the induction of EAE delays the onset and severity of disease SJL/J mice were immunized with 75 ug PLP 139-151 peptide in CFA, and intravenously injected with pertussis toxin. Mice were treated with either Tim-2Ig, or PBS or hIgG as controls every alternate day from day 0 to day 8. Mice were monitored for clinical signs of EAE.
Figure 6:
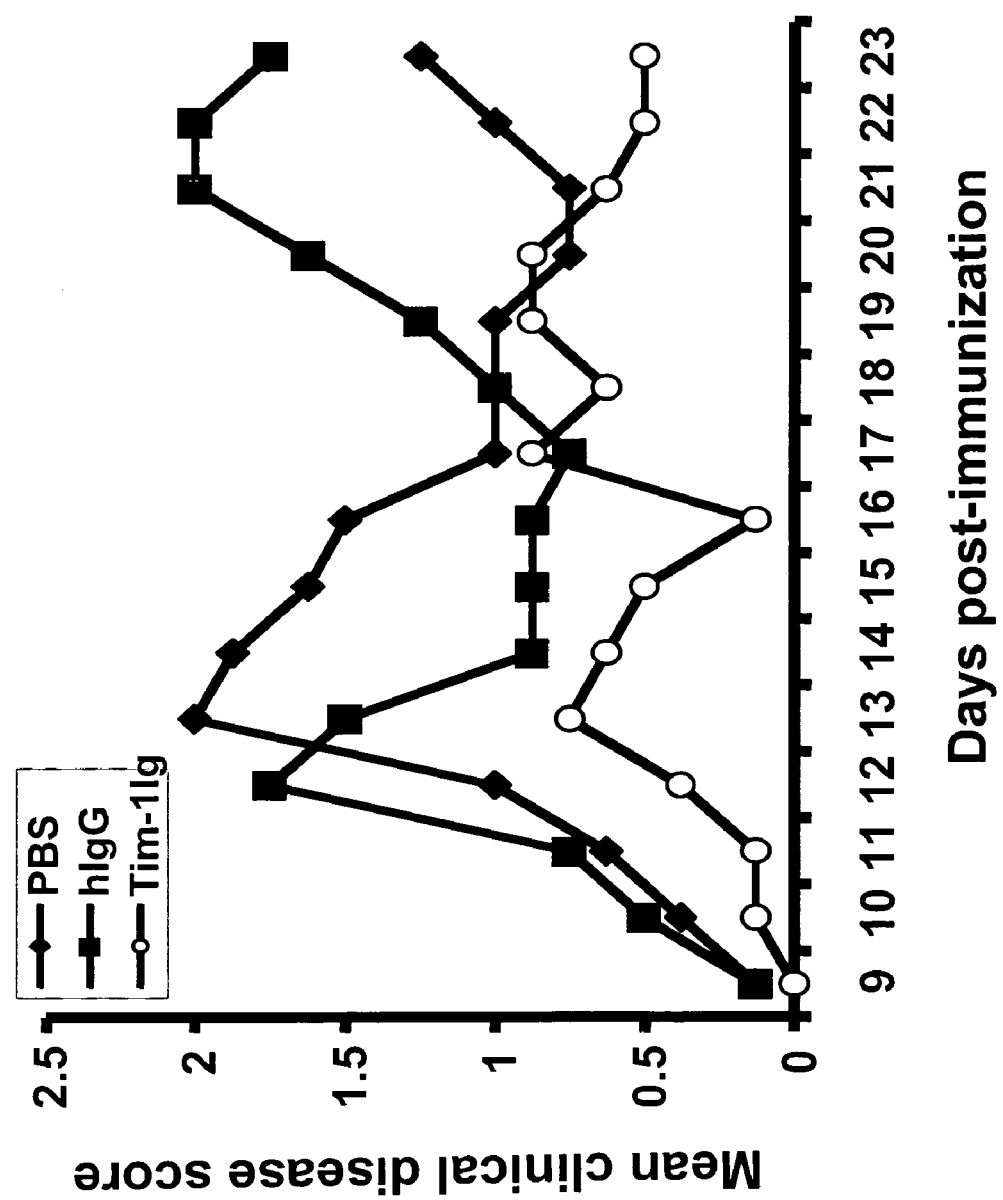
FIG. 6 shows that administration of Tim-1Ig during the induction of EAE delays the onset and severity of disease SJL/J mice were immunized with 75 ug PLP 139-151 peptide in CFA, and intravenously injected with pertussis toxin. Mice were treated with either Tim-1Ig, or PBS or hIgG as controls every alternate day from day 0 to day 8. Mice were monitored for clinical signs of EAE.

Administration of Tim-1 or Tim-2 Fusion Polypeptide to Delay the Onset and Severity of EAE Due to the ability of Tim-1Ig and Tim-2Ig to generate a Th2 biased immune response in a Th1 based environment applicants were interested in the influence that the Tim-1-Tim-1 ligand, and Tim-2-Tim-2 ligand, interaction would have on the induction and pathogenesis of a Th1-based autoimmune disease. To approach this question applicants immunized SJL/J mice with the encephalogenic peptide PLP 139-151 to induce experimental autoimmune encephalomyelitis (EAE), a Th1-mediated autoimmune disease and mouse model for the human disease multiple sclerosis. SJL/J mice were immunized with PLP 139-151 in complete freund's adjuvant to induce disease. Mice immunized for disease were also administered with Tim-1Ig, Tim-2Ig, hIgG, or PBS and monitored for clinical signs over a thirty-day period. Mice given hIgG or PBS demonstrated the expected relapsing-remitting disease course (FIGS. 5 and 6). In contrast, the Tim-2Ig fusion polypeptide administered mice demonstrated mild to no paralysis until day 24 post-immunization. The Tim-2Ig treated mice showed a peak clinical disease score of 1.5, significantly lower than that of the control treated mice (FIG. 5). The Tim-1 Ig treated mice demonstrated a slight delay in the onset of disease, and also showed a significantly lower severity of disease (FIG. 6).

Taken together, these data demonstrate that Tim-1 and Tim-2 are differentially expressed on Th2 cells, and that in vivo administration of these fusion polypeptides generates a Th2 response, even in a Th1 biased system. Furthermore, treating mice with Tim-1Ig or Tim-2Ig during the induction of a Th1 mediated autoimmune disease delays the onset and severity of clinical symptoms, providing a possible target for therapeutic manipulation.

EXAMPLE 6

Tim-2 is Differentially Expressed on Th2 Cells

Figure 7:
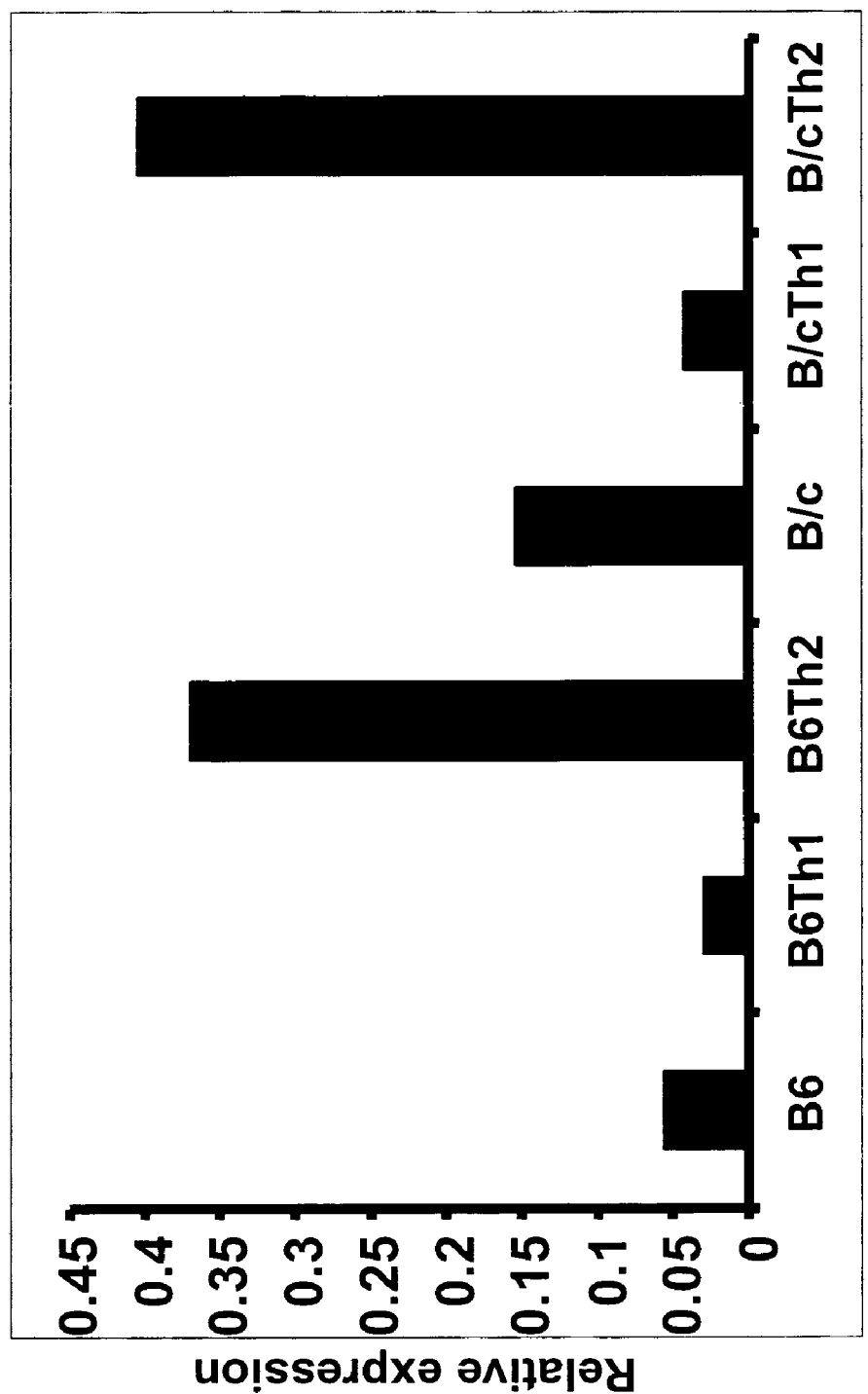
FIG. 7 shows that Tim-1 and Tim-2 Ligand(s) are expressed on activated antigen presenting cells. B220 (B cells), CD11b (macrophages and dendritic cells) and CD11c (dendritic cells) were purified from spleens of Balb/c mice and activated with LPS and interferon gamma. Twenty-four hours post-activation cells were stained with either hIgG (red line), Tim-1Ig biotinylated (green line), or Tim-2Ig biotinylated (blue line). Streptavidin-PE was used as a secondary detection reagent. All samples were analyzed by flow cytometry. Both Tim-1 ligand and Tim-2 ligand expression was upregulated on activated antigen presenting cells.

Naïve T cells from C57BL/6 and Balb/c mice were polarized using anti-CD3/CD28 stimulation in the presence of IL-12 and anti-Il-4 (Th1) or IL-4 and anti-IL-12 (Th2) conditions. RNA was extracted from cells and cDNA generated. Using specific Taqman primers and probes Tim-2 expression was determined relative to GAPDH. Tim-2 expression was preferentially upregulated in Th2 cells in comparison to Th1 cells (FIG. 7).

EXAMPLE 7

Figure 8:
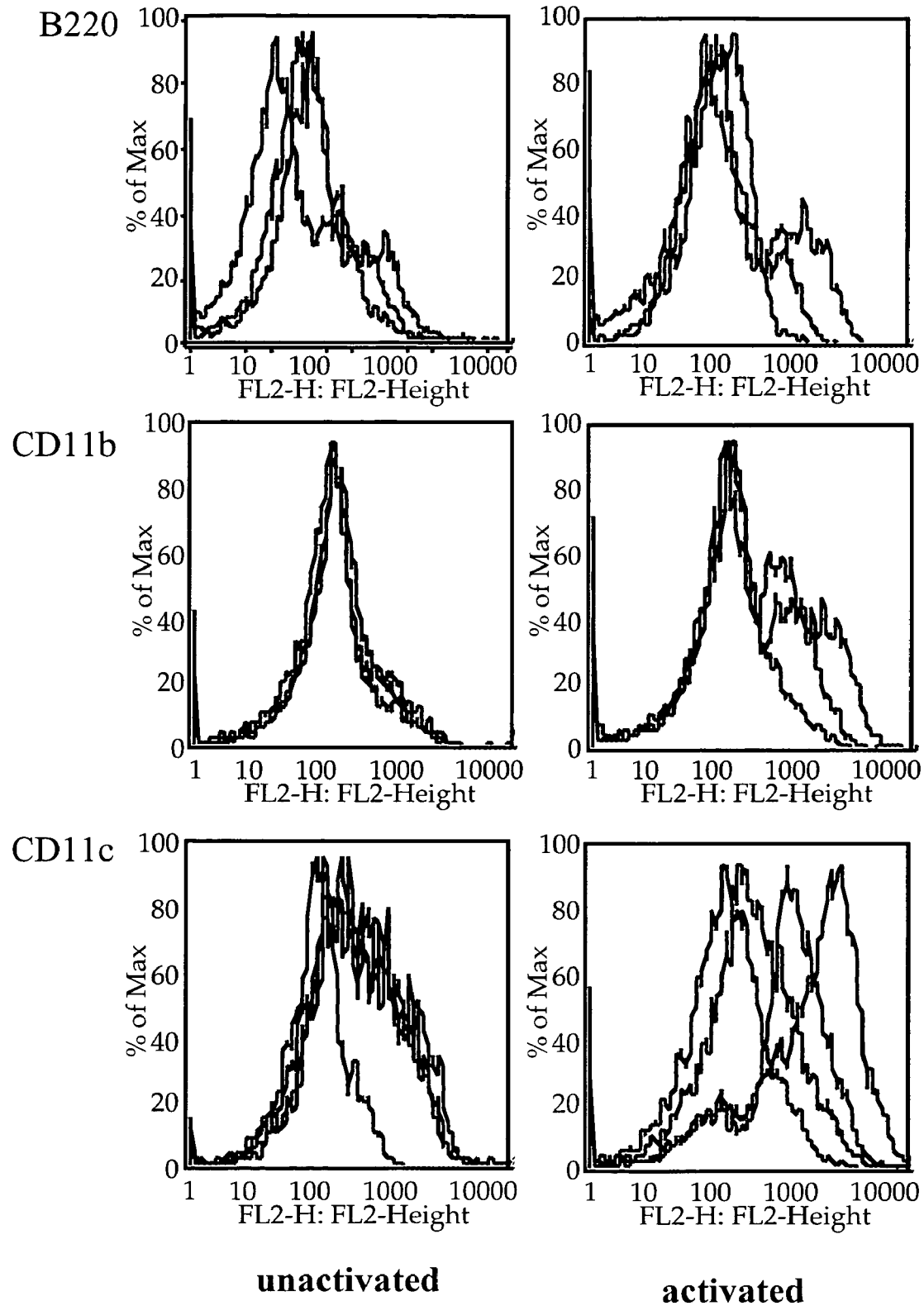
FIG. 8 shows expression of Tim-2 in Th1 and Th2 polarized cell lines. Naïve T cells from C57BL/6 and Balb/c mice were polarized using anti-CD3/CD28 stimulation in the presence of IL-12 and anti-Il-4 (Th1) or IL-4 and anti-IL-12 (Th2) conditions. RNA was extracted from cells and cDNA generated. Using specific Taqman primers and probes Tim-2 expression was determined relative to GAPDH. Tim-2 expression was preferentially upregulated in Th2 cells in comparison to Th1 cells.

Tim-1 and Tim-2 Ligand(s) are Expressed on Activated Antigen Presenting Cells B220 (B cells), CD11b (macrophages and dendritic cells) and CD11c (dendritic cells) were purified from spleens of Balb/c mice and activated with LPS and interferon gamma. Twenty-four hours post-activation cells were stained with either hIgG (red line), Tim-1Ig biotinylated (green line), or Tim-2Ig biotinylated (blue line). Streptavidin-PE was used as a secondary detection reagent. All samples were analyzed by flow cytometry. Both Tim-1 ligand and Tim-2 ligand expression was upregulated on activated antigen presenting cells (FIG. 8).

EXAMPLE 8

Administration of Tim1/Fc Fusion Polypeptides Facilitates Allograft Tolerance in a Mouse Islet Transplantation Model The outcome of T cell dependent alloimmune response, rejection or tolerance, often depends on the balance between i) cytopathic versus ii) immunoregulatory T cells. Our previous studies indicate that the mechanisms of Th1 to Th2 immune deviation to facilitate allograft tolerance lie on, at least in part, enhancing the T regulatory function. Since administration of Tim1/Fc or Tim2/Fc can induce Th1 to Th2 immune deviation, applicants hypothesize that Tim1/Fc and Tim2/Fc treatment will facilitate allograft tolerance.

Figure 9:
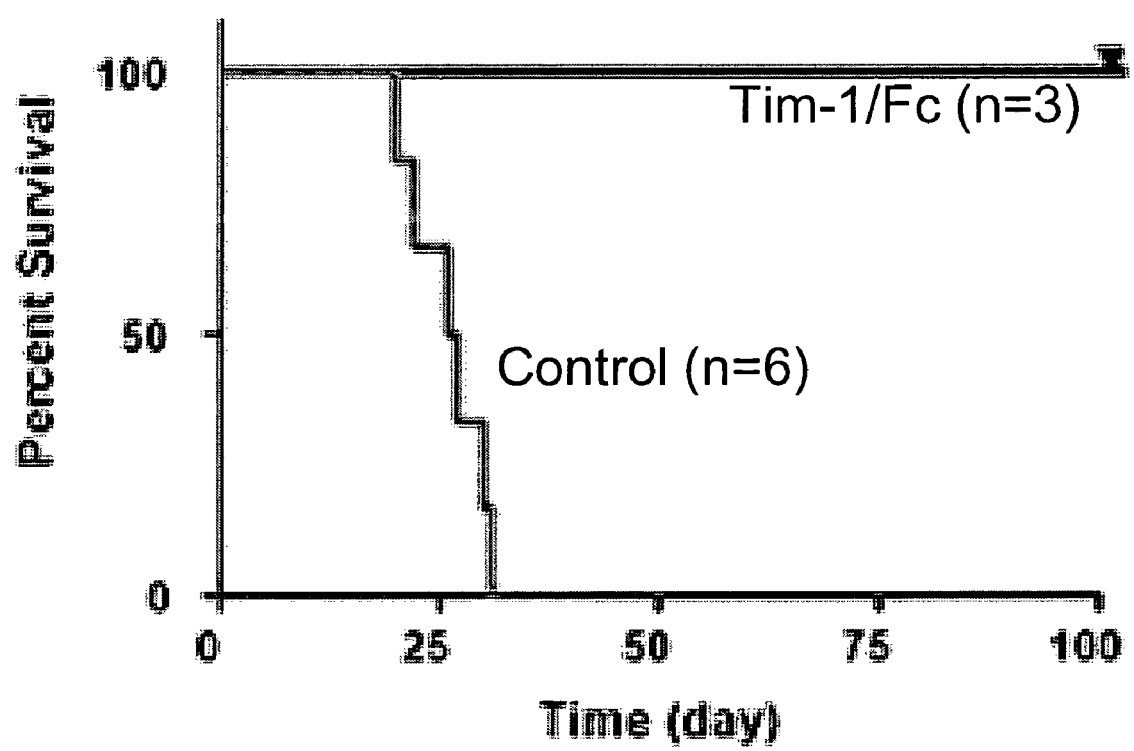
FIG. 9 shows that Tim1/Fc mono-therapy permits engraftment of minor mismatched islet allografts. Balb/c mice were rendered diabetes by single i.p. injection of Streptocotocin at a dose of 240 mg/kg. Islet allografts from DBA/2 donors were transplanted under the renal capsule of right kidney. The recipients were treated with Tim1/Fc at a dose of 0.25 mg/mouse on day 0, 2, and 4 of transplantation.
Figure 10:
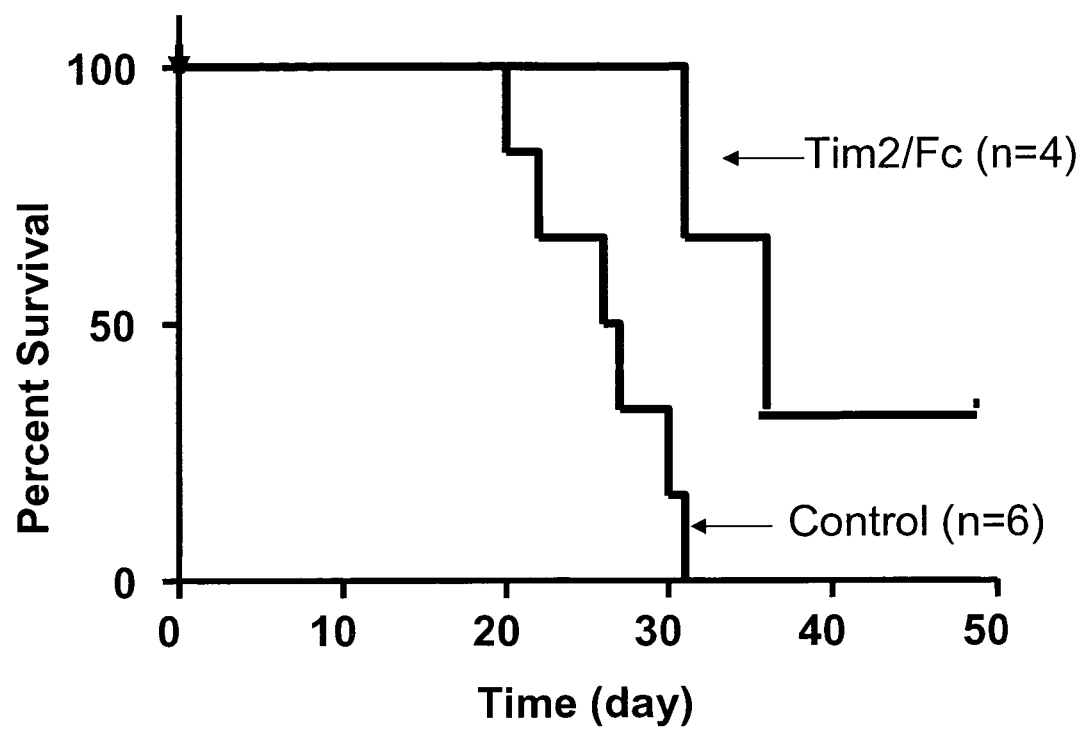
FIG. 10 shows that Tim2/Fc mono-therapy delays rejection and permits engraftment of minor mismatched islet allografts. Balb/c mice were rendered diabetes by single i.p. injection of Streptocotocin at a dose of 240 mg/kg. Islet allografts from DBA/2 donors were transplanted under the renal capsule of right kidney. The recipients were treated with Tim2/Fc at a dose of 0.25 mg/mouse on day 0, 2, and 4 of transplantation.
Figure 11:
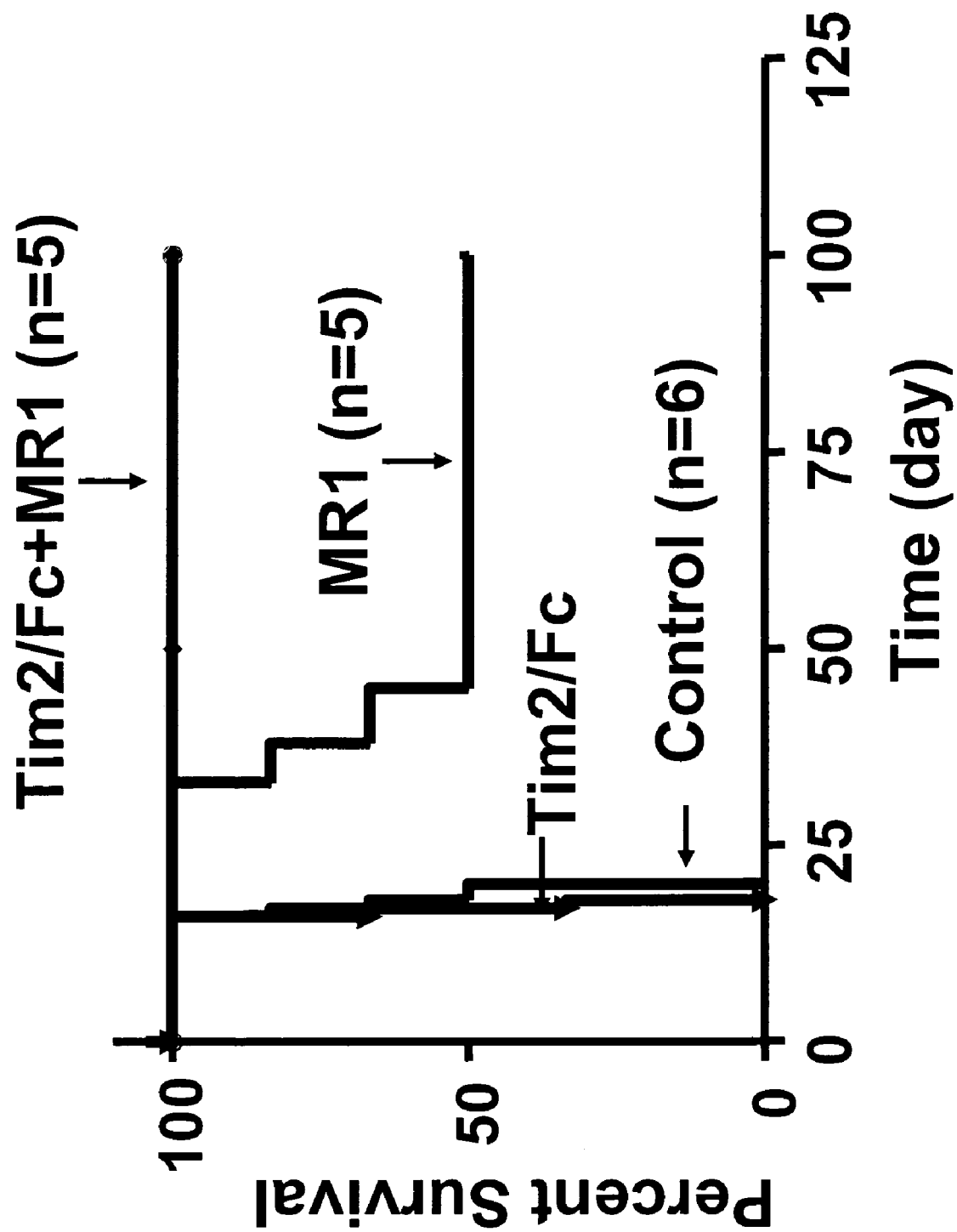
FIG. 11 shows that Tim2/Fc synergizes with anti-CD154 to promote MHC mismatched allograft tolerance. C57BL/6 mice were rendered diabetes by single i.p. injection of Streptocotocin at a dose of 260 mg/kg. Islet allografts from DBA/2 donors were transplanted under the renal capsule of right kidney. The recipients were treated with Tim2/Fc at a dose of 0.25 mg/mouse on day 0, 2, and 4 of transplantation and MR1 at a dose of 0.25 mg/mouse on day 0 and 2 of transplantation.

Applicants utilized an islet allograft model cross minor and major histocompatibility barriers. A short course treatment with Tim1/Fc, as a mono-therapy, is sufficient to prevent rejection and permanent islet allograft survival in all 3 recipients crossing minor histocompatibility barriers, in comparison with the mean graft survival at 28 days in untreated group (FIG. 9). A similar result is observed in Tim2/Fc treated recipients. Administration of Tim2/Fc results in significant delay of islet allograft rejection in 3 recipients and permanent engraftment in 1 recipient (FIG. 10). In addition, Tim2/Fc treatment, in combination with a sub-optimal dose of anti-CD154 (MR1) antibody, confers permanent islet allograft engraftment in all five recipients in a fully MHC-mismatched stringent mouse strain combination (FIG. 11). These data suggest that Tim1/Fc and Tim2/Fc treatment promote Th1 to Th2 immune deviation, enhancing T regulatory function and facilitate allograft tolerance.

EXAMPLE 9

Figure 12A:
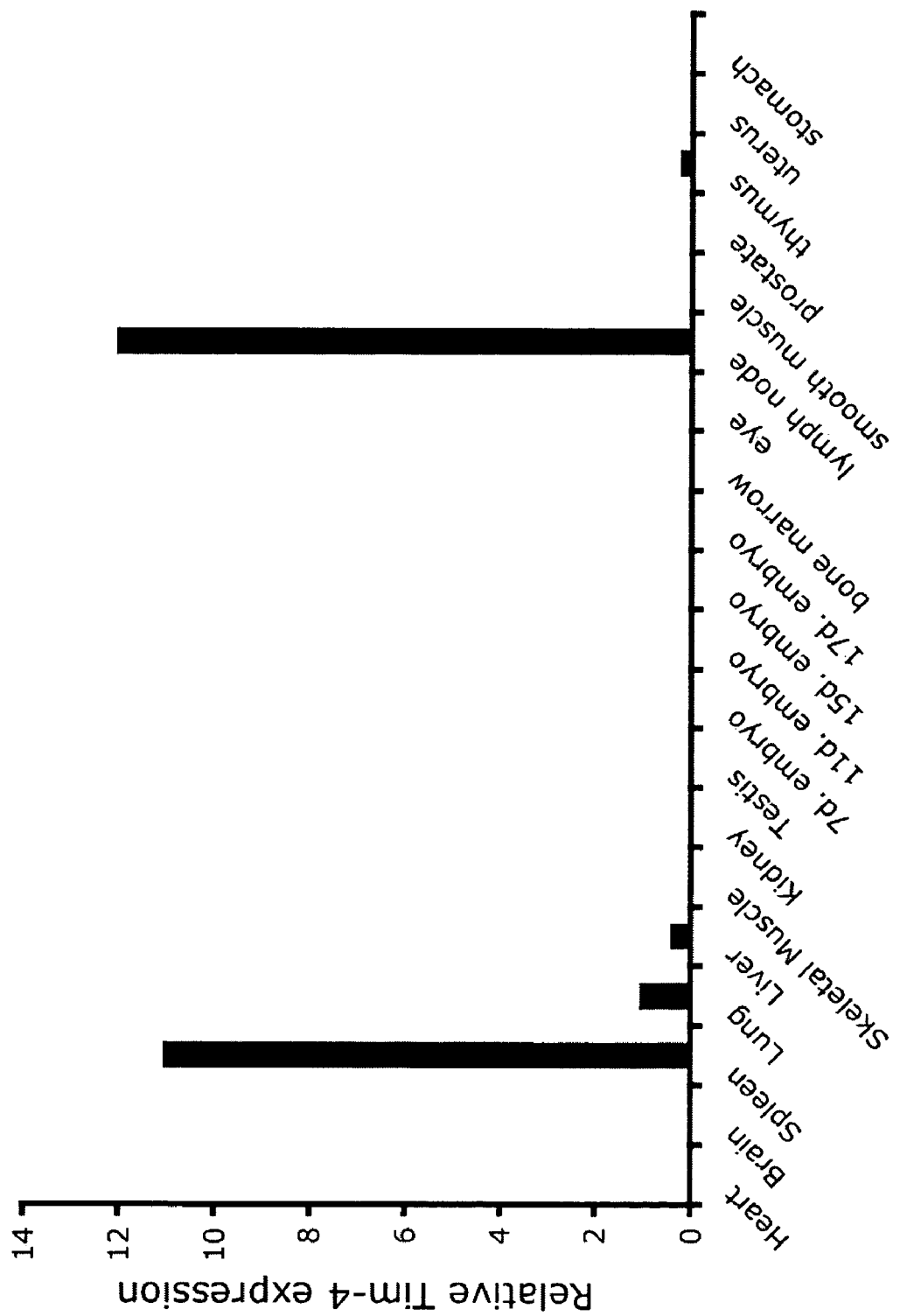
FIG. 12 shows that Tim-4 is expressed in macrophages and mature dendritic cells, but not in T cells. (a) Taqman quantitative PCR was performed on Clontech multiple tissue cDNA panels in duplicate wells to analyze Tim-4 mRNA in various mouse organs. (b) DO11.10 TcR transgenic T cells were polarized in vitro to the $T_H1$ or $T_H2$ lineage, and RNA was prepared from resting cells after each round of restimulation. RNA was also prepared from long-term T cell clones AE7 ($T_H1$) and D10.G4 ($T_H2$), as well as CHO-Tim-4 stable transfectants. Data is representative of 2 experiments. (c) SJL/J spleen and lymph node cells were purified into $CD11b^+$, $CD11c^+$, $B220^+$, and $CD3^+$ populations. Data is representative of over 5 experiments. (d) Dendritic cells were generated in vitro from bone marrow cells using GM-CSF or Flt3L, and some cells were stimulated with LPS. Flt3L-generated cells were depleted of the plasmacytoid fraction. Data is representative of 2 experiments. (e) Dendritic cells were generated in vivo from CB6F1 mice injected with CMS5 Flt3L-producing tumor cells. Splenic cells depleted of T and B cells were separated into the populations indicated. All cell types indicated were subjected to Tim-4 Taqman RT-PCR to quantitate Tim-4 mRNA expression. All data is expressed as Tim-4 expression relative to GAPDH expression, performed in triplicate wells.

Expression of Tim-4 in Macrophages and Mature Dendritic Cells, But not in T Helper Subsets Because the Tim molecules characterized thus far are involved in T cell responses (Kuchroo et al. (2003). Nat Rev Immunol 3, 454-462), applicants first determined whether Tim-4 was also expressed in immune organs. Real-time quantitative PCR on multiple tissue cDNA panels revealed that Tim-4 mRNA was expressed in mouse spleen and lymph node, with very low expression in lung, liver, and thymus (FIG. 12A). This apparent restriction to immune organs suggested that Tim-4 is an immunologically relevant molecule.

Figure 12B:
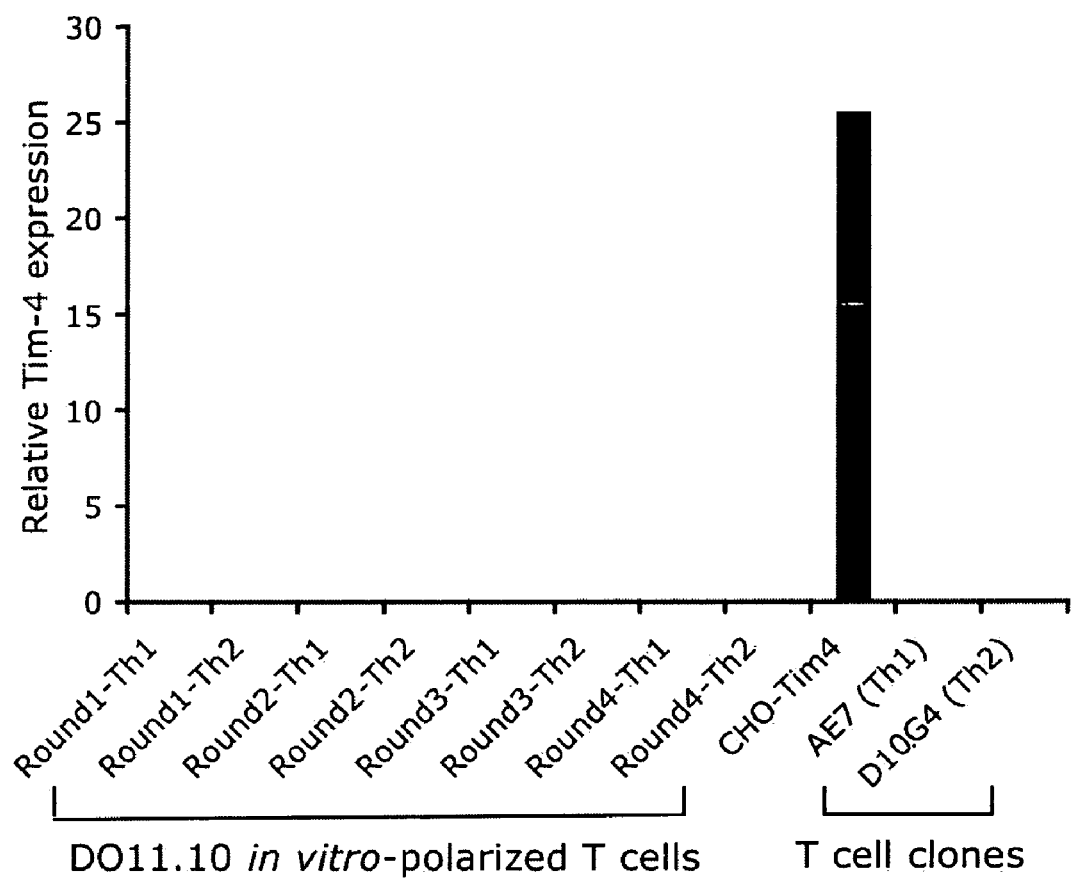
Figure 12C:
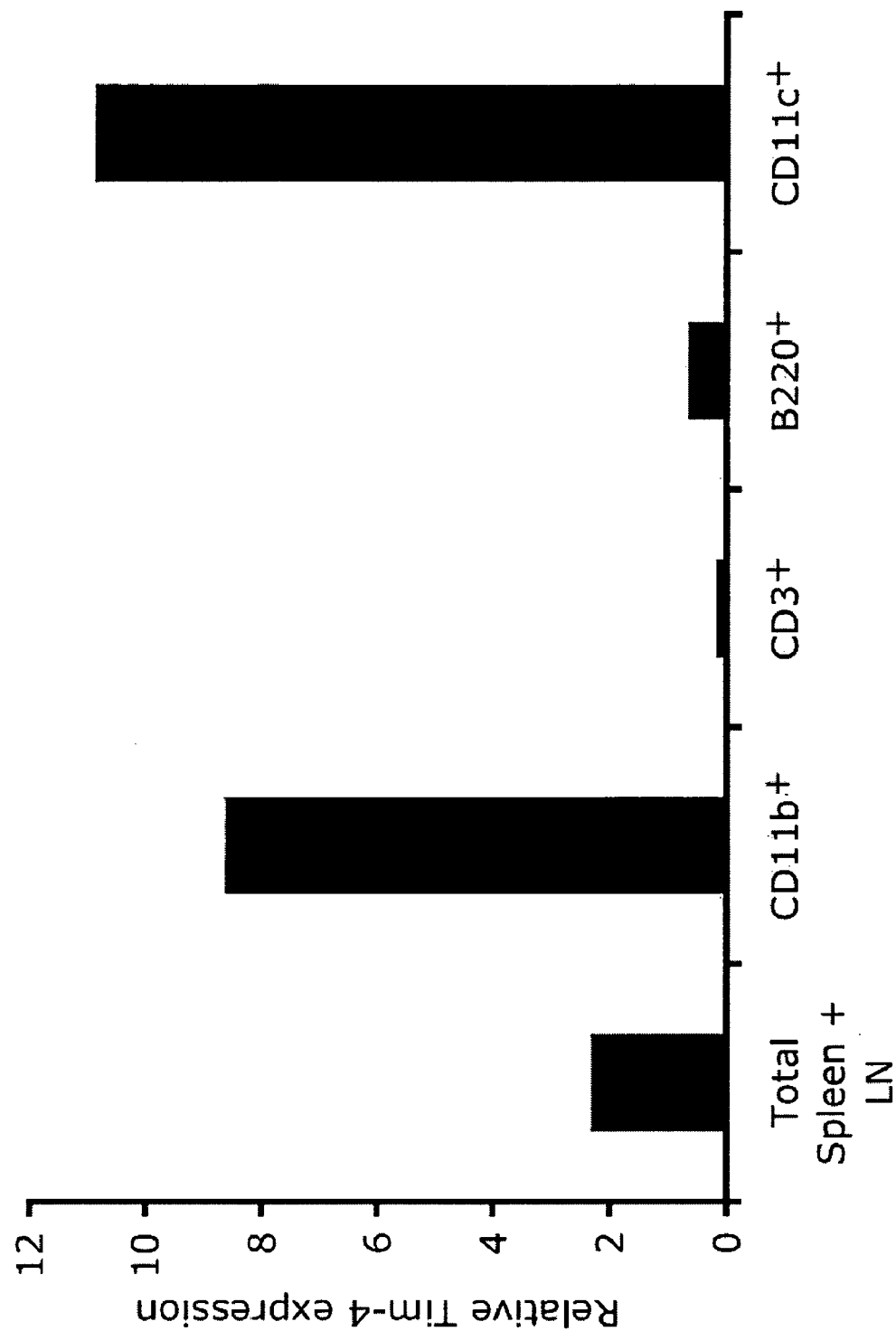

Applicants next analyzed whether Tim-4 could also be differentially expressed in $T_H1$ vs. $T_H2$ subsets. Applicants used quantitative PCR to detect Tim-4 mRNA expression in $T_H1$ (AE7) and $T_H2$ (D10.G4) clones, and in DO11.10 transgenic T cells polarized in vitro to the $T_H1$ or $T_H2$ lineage. These cells were analyzed after each round of polarization to determine the kinetics of Tim-4 expression. Although these $T_H1$ cells specifically express Tim-3 and the $T_H2$ cells specifically express Tim-2 upon the third round of in vitro polarization (Monney et al. (2002). Nature 415, 536-541), Tim-4 mRNA was detected in neither $T_H1$ nor $T_H2$ cells through four rounds of polarization (FIG. 12B). Tim-4 thus appeared to have a different expression pattern within the immune system than those of the other Tim molecules thus far characterized. As Tim-4 mRNA was highly expressed in the spleen, applicants next assayed which cell types within the spleen expressed Tim-4 mRNA. $CD11b^+$, $CD11c^+$, and $B220^+$ cells (mainly representing macrophages, dendritic cells, and B cells, respectively) were isolated by positive selection from the spleens of SJL/J or C57BL/6 mice. Quantitative RT-PCR performed on these cells revealed high Tim-4 mRNA expression in the $CD11b^+$ and $CD11c^+$ cells, and to a lesser extent in the $B220^+$ subset (FIG. 12C). However, applicants did not detect Tim-4 mRNA in T cells. Tim-4 therefore appears to be expressed in splenic antigen presenting cells (APCs), but not in T cells.

Figure 12D:
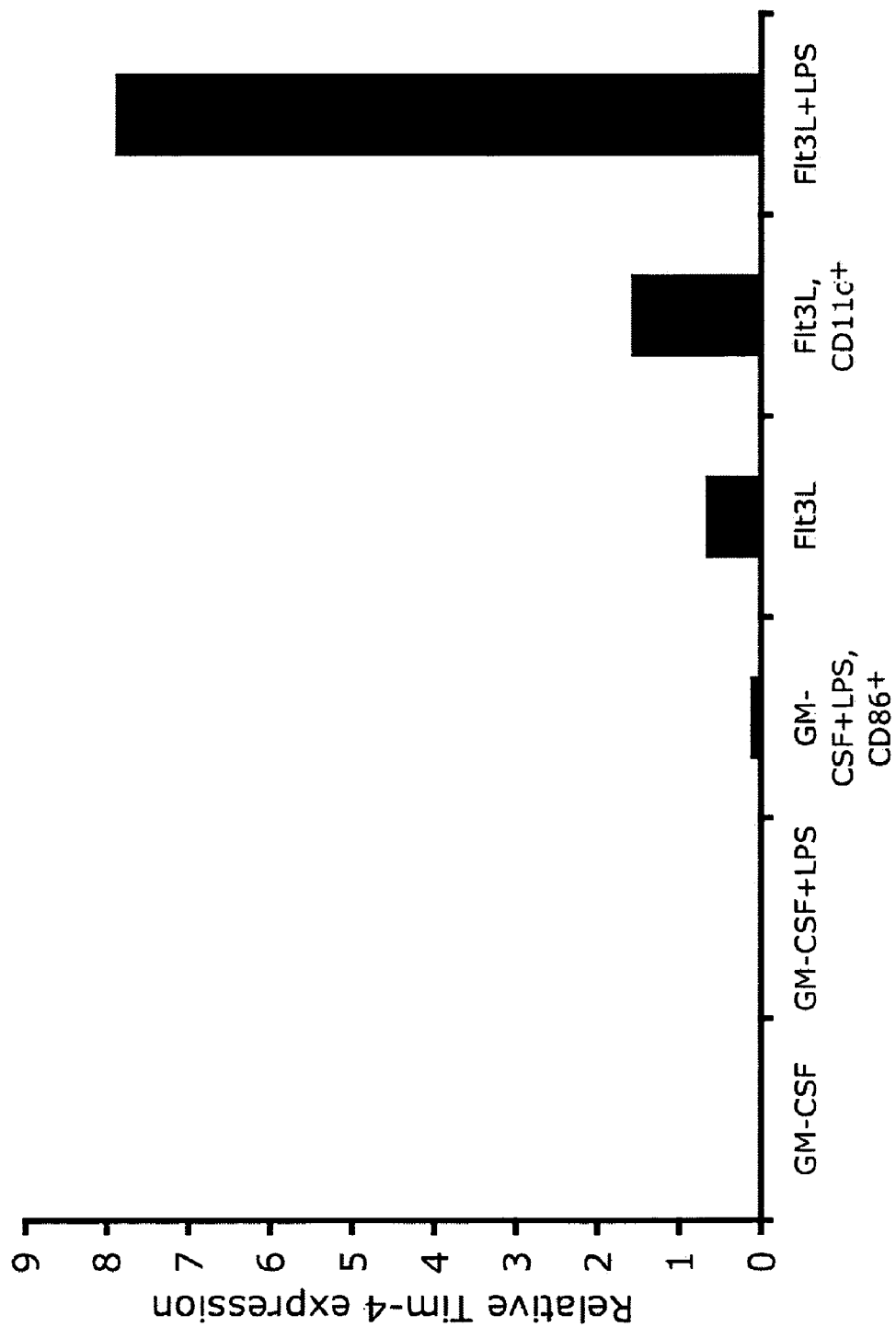
Figure 12E:
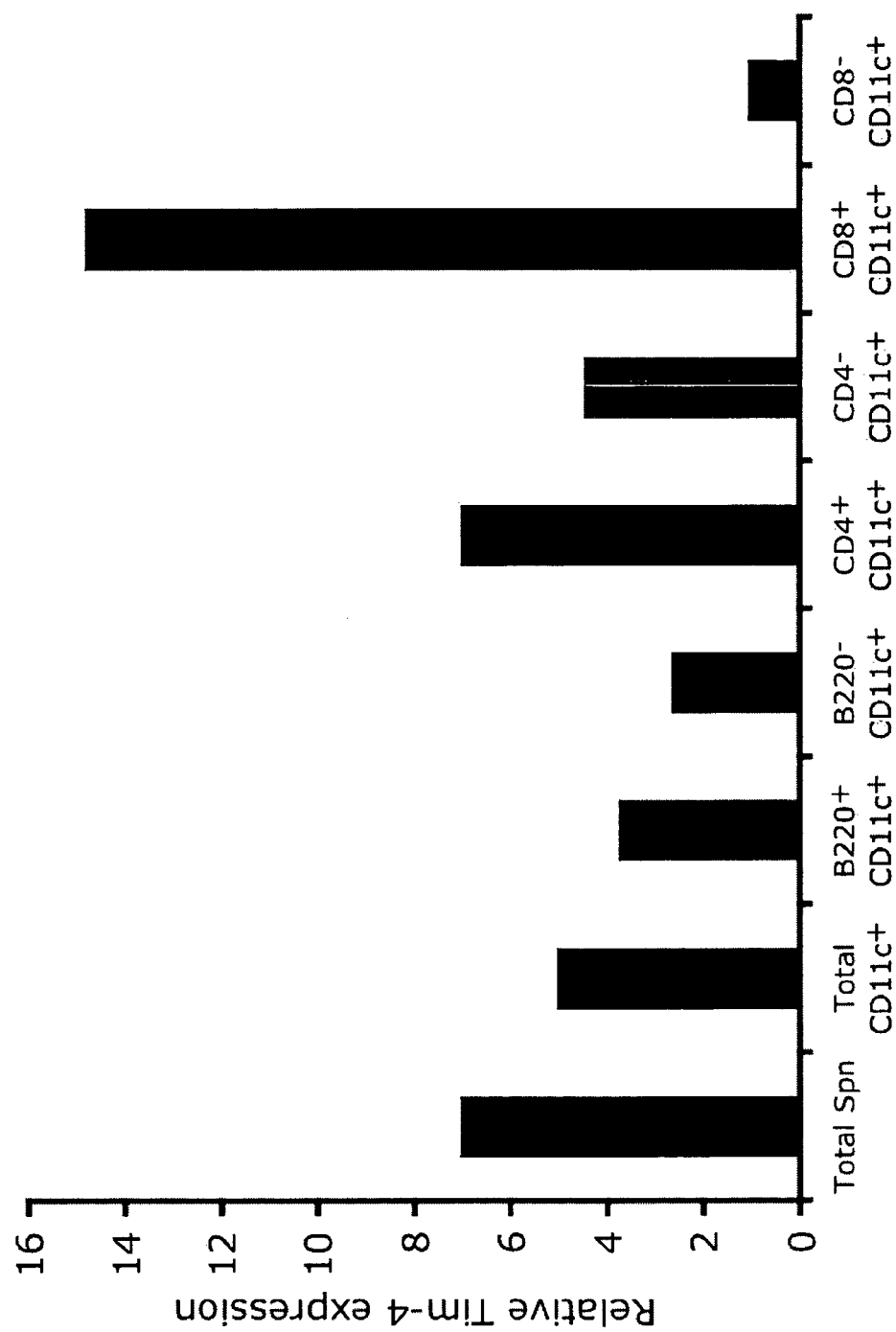

As antigen presenting cells represent an extremely heterogeneous group of cells, applicants sought to identify which types of APCs might predominantly express Tim-4 mRNA. Applicants directed our attention to dendritic cell subsets, as different populations of these professional antigen presenting cells have been reported to preferentially induce different types of T helper cell responses (Eisenbarth et al. (2003). Curr Opin Immunol 15, 620-626; Rissoan et al. (1999). Science 283, 1183-1186). Dendritic cells were generated in vitro from bone marrow cells incubated with granulocyte-macrophage colony-stimulating factor (GM-CSF) or FMS-like tyrosine kinase 3 ligand (Flt3L), with or without addition of lipopolysaccharide (LPS). GM-CSF-derived DCs are mainly of the myeloid lineage, whereas Flt3L treatment generates a mix of myeloid and lymphoid DC types (Brasel et al. (2000). Blood 96, 3029-3039; Gilliet et al. (2002). J Exp Med 195, 953-958; Maraskovsky et al. (1996) J Exp Med 184, 1953-1962). LPS treatment matures the DCs and causes the preferential outgrowth of lymphoid DCs in Flt3L-treated cultures (Brasel et al. (2000). Blood 96, 3029-3039). Tim-4 mRNA was most highly expressed in cells generated by Flt3L and matured with LPS (FIG. 12D). These Tim-4 positive cells were of the lymphoid lineage and not the plasmacytoid lineage, as these populations were depleted of $B220^+$ cells. Expression was seen in neither immature nor mature myeloid-type DCs. To further extend this observation of Tim-4 mRNA expression in mature lymphoid dendritic cells, mice were treated with Flt3L-producing cells, and splenocytes from treated mice were sorted into different populations. Consistent with the previous observation, the highest Tim-4 expression was observed in the most mature dendritic cells, which express both CD11c and CD8 (Martinez del Hoyo et al. (2002). Blood 99, 999-1004) (FIG. 12E). Taken together, these data indicate that, unlike other members of the Tim family, Tim-4 is not expressed in T cells but is instead present in APCs, particularly in mature DCs.

To determine whether Tim-4 can be expressed as a polypeptide, applicants transfected CHO and HEK293 cells with cDNA encoding Tim-4 with an N-terminal HA tag and were able to observe its expression on the surfaces of both cell types by anti-HA antibody staining (FIGS. 14, 15). In addition, applicants were able to demonstrate that a band of 60 kDa could be immunoblotted from these cells with anti-HA.

These data suggest that Tim-4 is not only present at the mRNA level but can be translated into a functional polypeptide.

EXAMPLE 11

Expression of Tim-4 Ligand on Activated T Cells and B Cells

Figure 13:
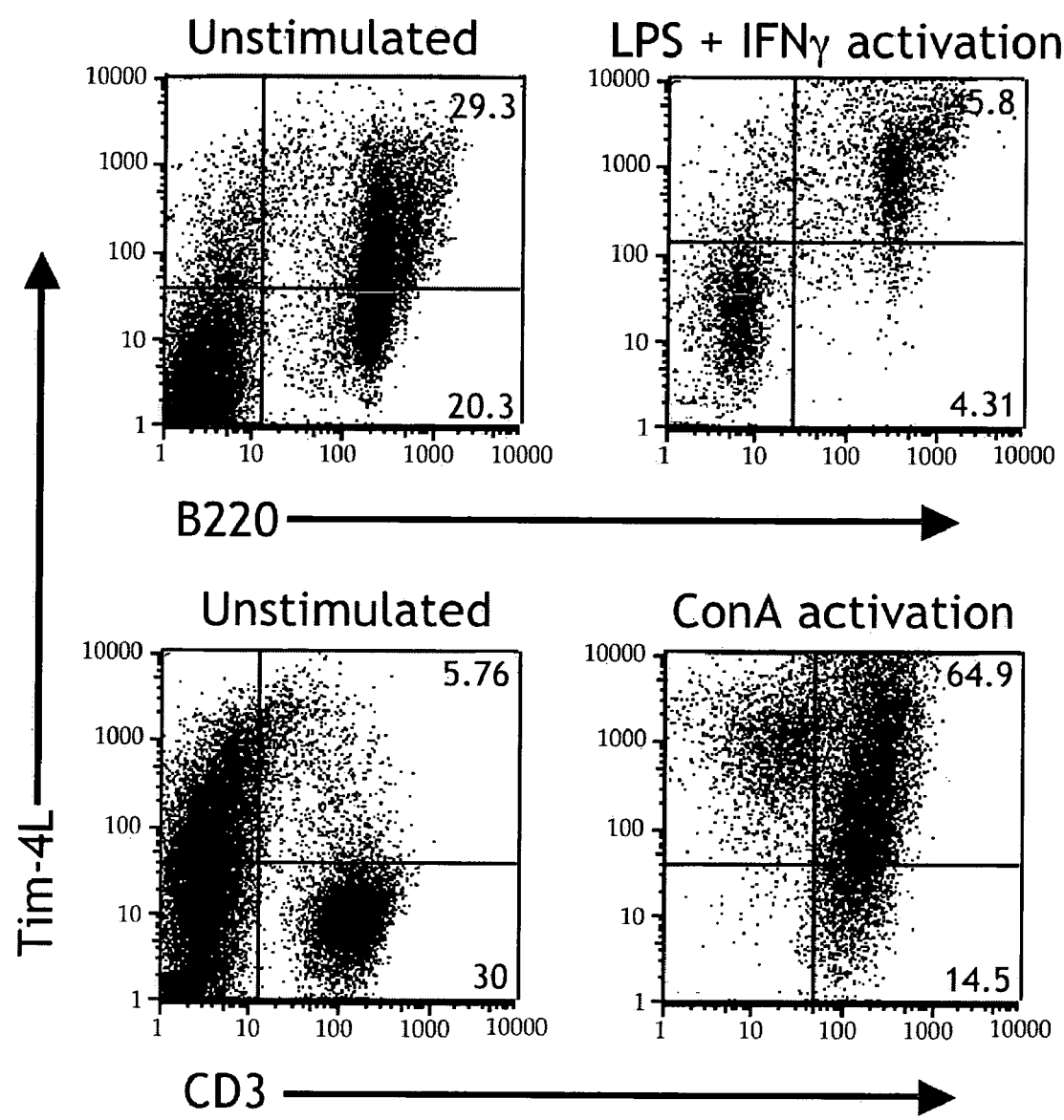
FIG. 13 shows that Tim-4 ligand is expressed on B cells and activated T cells. Total SJL/J spleen cells, either unstimulated or activated with LPS and IFN-γ (for B cells), or with ConA (for T cells), were stained with B220-FITC or CD3-FITC and Tim-4-Ig (with anti-human IgG-PE used for detection). Data is representative of 4 separate experiments.

To identify and analyze the expression pattern of a potential Tim-4 ligand (Tim-4L), applicants generated a soluble Ig fusion polypeptide consisting of the extracellular IgV and mucin domains of Tim-4 fused to a human IgG1 Fc tail (Tim-4-Ig). This fusion polypeptide was used in flow cytometry to detect expression of Tim-4L in SJL/J mouse splenocytes. In unstimulated splenocytes, Tim-4L could be seen on a population of B (B220$^+$) cells but not on T (CD3$^+$) cells; however, upon activation by LPS and interferon (IFN)-γ treatment, Tim-4L was seen on most B cells and on the majority of ConA-activated T cells (FIG. 13). It therefore appeared that, whereas Tim-4 is expressed on antigen presenting cells, Tim-4L is expressed on activated B and T cells. This expression pattern, as well as the structural similarities between the Tim family members, led us to examine whether Tim-4 could interact with one of the previously-identified Tim molecules expressed on activated T cells. Tim-3 is not expressed on all activated T cells, but rather is upregulated only on terminally-differentiated TH 1 cells, and is not expressed on B cells. Tim-3 therefore was unlikely to serve as a ligand for Tim-4, but Tim-1 and Tim-2 remained potential candidates for an interaction with Tim-4.

EXAMPLE 12

Identification of Tim-1 as the Endogenous Ligand for Tim-4

Figure 14A:
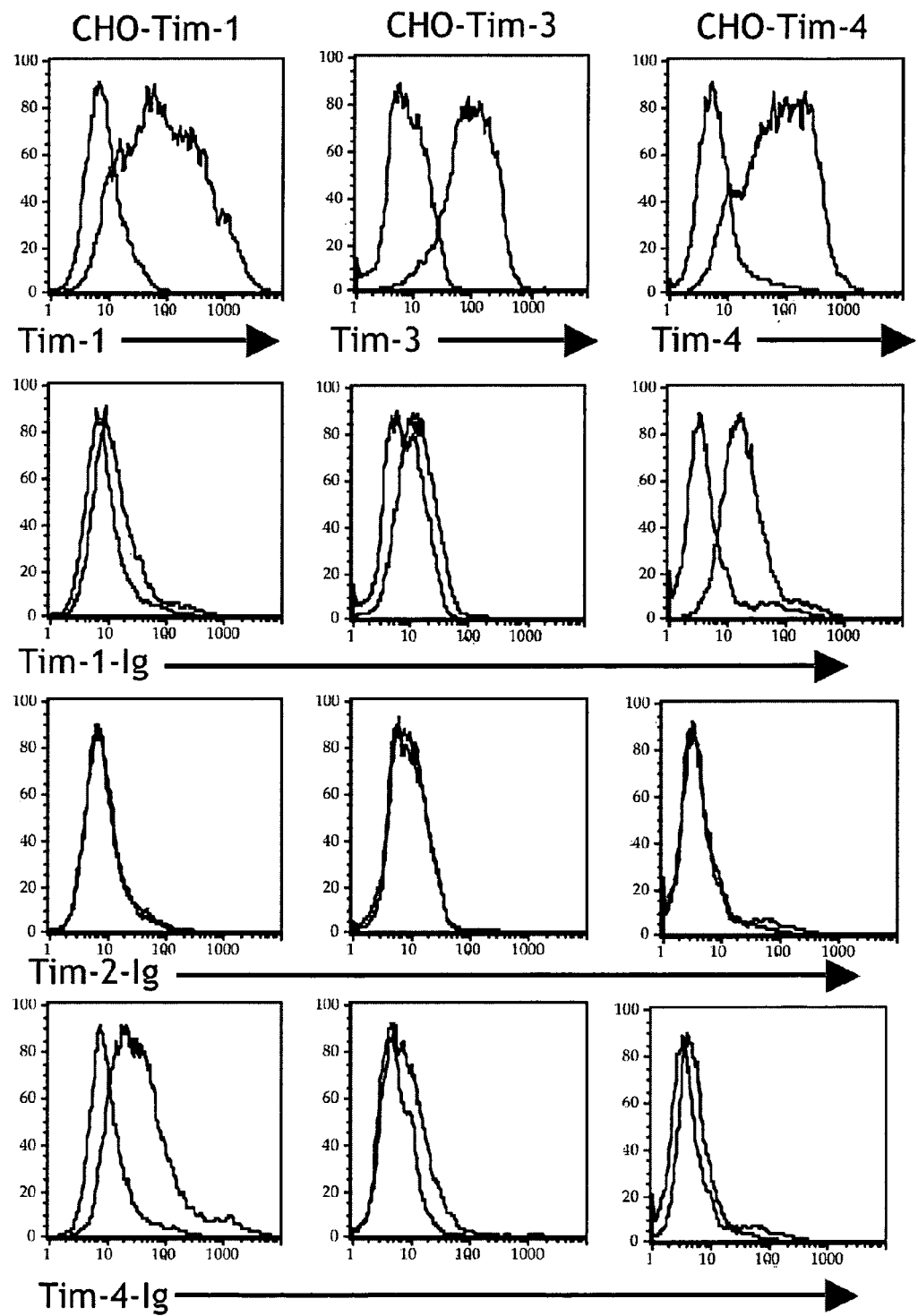
FIG. 14 shows that Tim-4 specifically interacts with Tim-1. (a) CHO cells transfected with Tim-1, Tim-3, or Tim-4 cDNA were stained with Tim-1-Ig (detected with anti-mIgG2a-PE, with secondary antibody alone as control), Tim-2-Ig, or Tim-4-Ig (both detected with anti-hIgG-PE, with hIgG as control). Tim-1 and Tim-3 were visualized on the cell surface with monoclonal anti-Tim-1 or anti-Tim-3, respectively, and Tim-4 was detected with biotinylated anti-HA (visualized with streptavidin-PE; all are compared to isotype controls). Data is representative of over 10 experiments. (b) HEK293 cells transfected with Tim-1 or Tim-4 were stained with Tim-1-Ig or Tim-4-Ig as before. To assess specific staining, Tim-1-Ig was pre-incubated with anti-Tim-1 or anti-Tim-3 and then used to stain Tim-4 transfectants. Additionally, Tim-1 transfectants were pre-incubated with anti-Tim-1 or anti-Tim-3 and then stained with Tim-4-Ig. Data is representative of over 5 experiments.

To determine whether Tim-4 could interact with another Tim molecule, applicants utilized CHO cell transfectants expressing Tim-1, Tim-3, or Tim-4 on the cell surface and used various Tim fusion polypeptides (Tim-1-Ig, Tim-2-Ig, Tim-4-Ig) for cell surface staining. Tim-4-Ig bound to Tim-1 transfectants, but not to Tim-3 or Tim-4 transfectants (FIG. 14A). Conversely, Tim-1-Ig bound to Tim-4 transfectants but not to Tim-1 or Tim-3 transfectants (FIG. 14A). The staining of Tim-4 transfectants with Tim-1-Ig fusion polypeptide was observed whether the full-length Tim-1-Ig, containing the Tim-1 IgV and mucin domains, or a Tim-1-Ig containing only the IgV domain was utilized (FIG. 14A). In contrast, Tim-2-Ig fusion polypeptide (also consisting of the extracellular IgV and mucin domains) did not stain any of the transfectants assayed, and none of the fusion polypeptides bound to CHO-Tim-2 transfectants. This data shows that Tim-4 interacts with Tim-1 and not with Tim-2, which shares homology with Tim-1 (McIntire et al. (2003). Nature 425, 576).

Figure 14B:
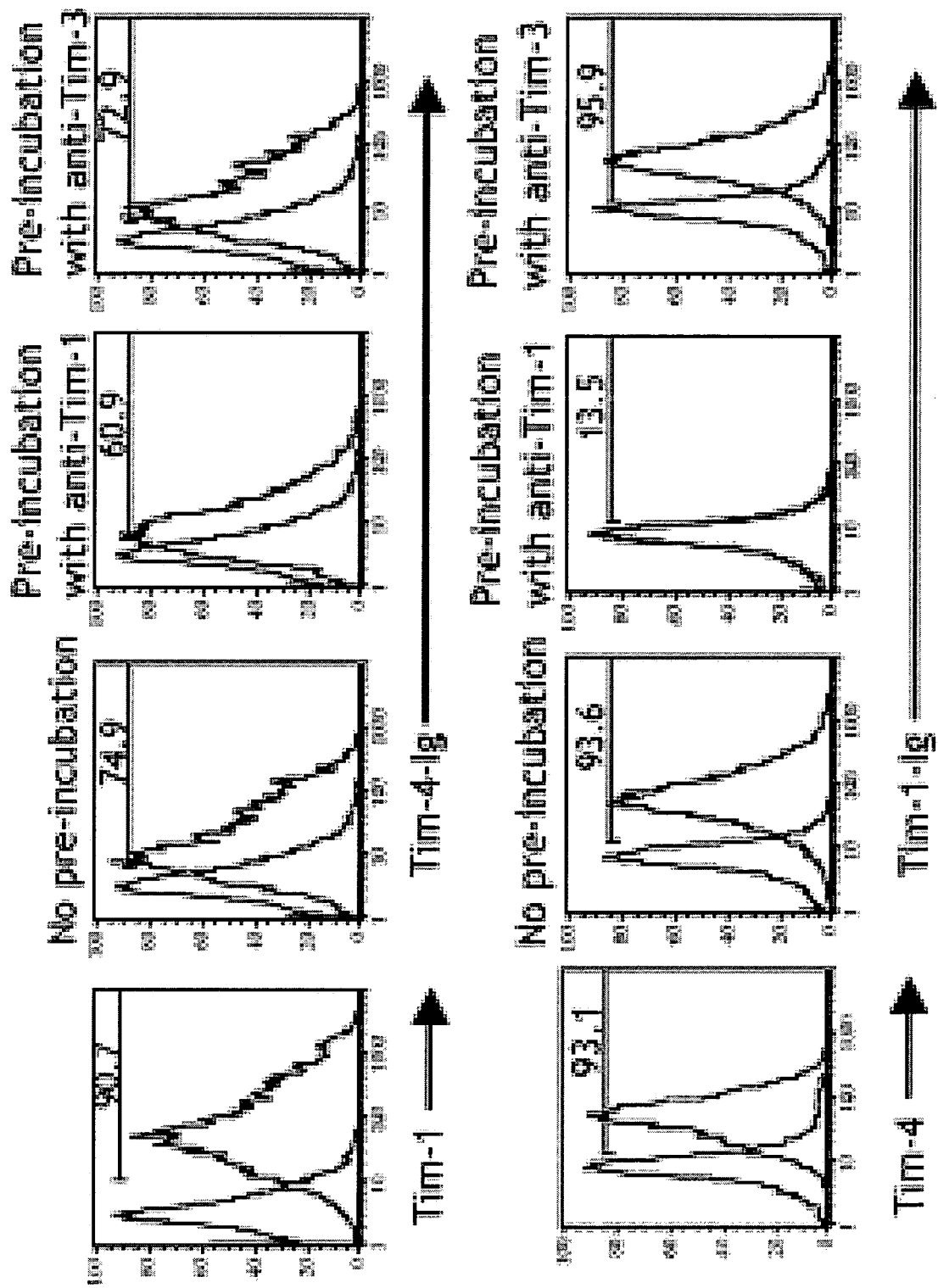

To assess the specificity of this interaction, applicants tested whether an anti-Tim-1 monoclonal antibody could block Tim-1-Tim-4 binding. This antibody was generated against the IgV region of the Tim-1 molecule and therefore should not interact with the Tim-1 mucin domain. First, Tim-1 transfectants expressing full-length Tim-1 were incubated with anti-Tim-1 and subsequently stained with Tim-4-Ig. This pre-incubation with anti-Tim-1 decreased Tim-4-Ig binding to Tim-1 transfectants but did not completely eliminate the binding. In contrast, incubation with anti-Tim-3 (Monney et al. (2002). Nature 415, 536-541) (as a control) had little effect on Tim-4-Ig binding (FIG. 14B). The incomplete nature of this blocking likely stemmed from the fact that the Tim-1 transfectants expressed the full-length Tim-1 molecule, whereas the antibody only bound to the IgV domain, thus indicating that some of the interaction between Tim-4 and Tim-1 could involve the Tim-1 mucin domain. In a reciprocal experiment, Tim-1-Ig fusion polypeptide (containing only the Tim-1 IgV domain) was pre-incubated with anti-Tim-1 and then used to stain Tim-4 transfectants. Incubation of Tim-1-Ig with anti-Tim-1 completely eliminated the binding of the fusion polypeptide to Tim-4 transfectants, whereas incubation with anti-Tim-3 did not alter its binding (FIG. 14B). Taken together, these experiments indicated that the staining seen on transfectants represented a specific interaction between Tim-4 and Tim-1, which could be blocked by prior incubation with anti-Tim-1 antibody.

EXAMPLE 13

Demonstration that Tim-4 Specifically Binds to Tim-1-Bearing T Cells

Figure 15A:
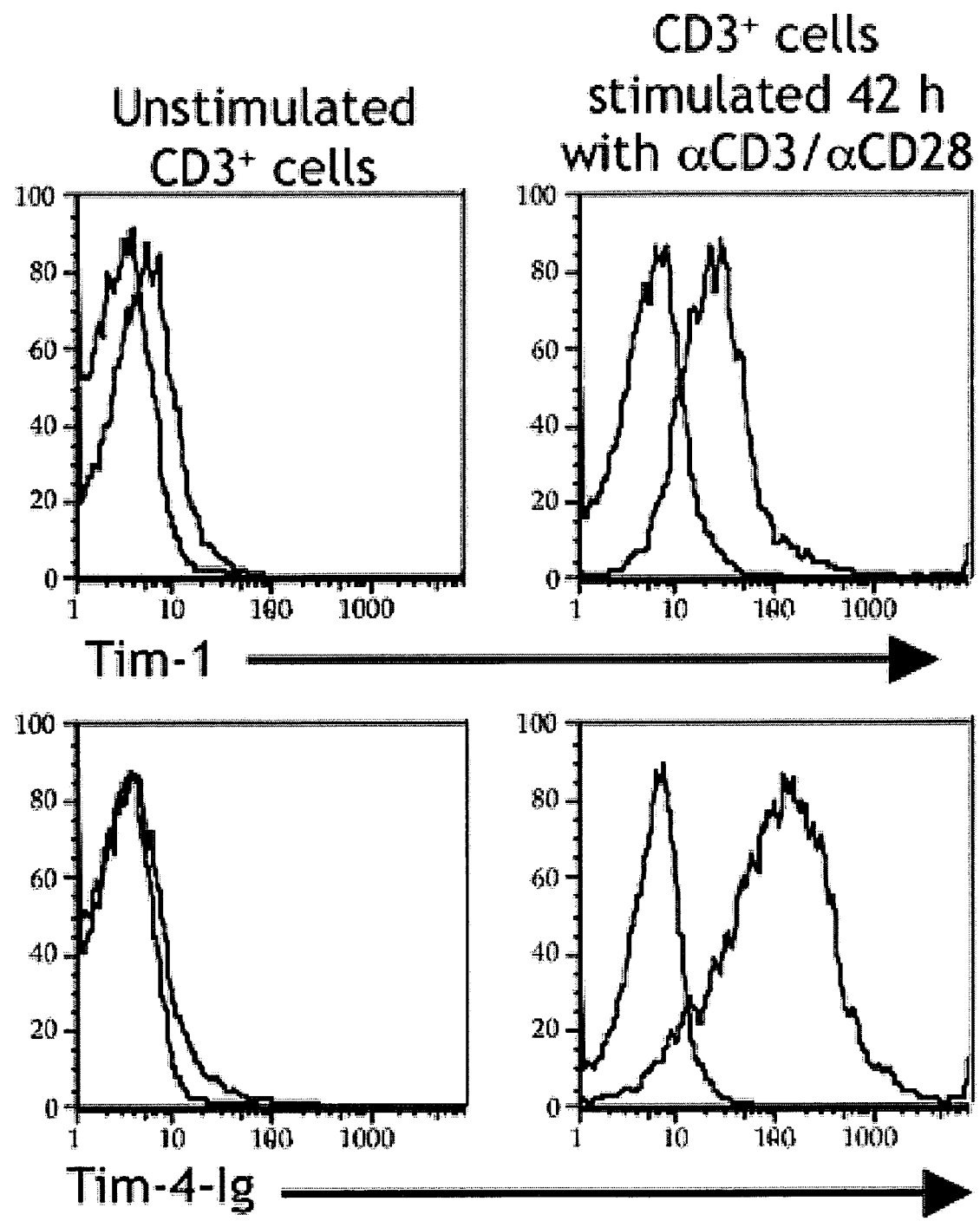
FIG. 15 shows that the Tim-4-Tim-1 interaction can be observed on normal T cells. (a) $CD3^+$ cells were purified from total splenocytes and activated with anti-CD3 and anti-CD28. Cells were stained with anti-Tim-1 or Tim-4-Ig as before. (b) Total splenocytes were stimulated with ConA and stained with anti-CD3 or Tim-4-Ig as before. Cells were preincubated with either anti-Tim-1 or anti-Tim-3 before staining with Tim-4-Ig to assess the Tim-1 specificity of the Tim-4-Ig binding shown. (c, d) DO11.10 TCR transgenic T cells polarized in vitro to the $T_H1$ or $T_H2$ lineage were activated for 3 h with PMA+Ionomycin+Golgi Stop, then stained with anti-Tim-1 or Tim-4-Ig as before. Stimulated cells were also stained extracellularly with anti-CD4 and intracellularly with cytokine antibodies to confirm their polarization to the $T_H1$ or $T_H2$ lineage. All data are representative of at least 4 experiments.
Figure 15B:
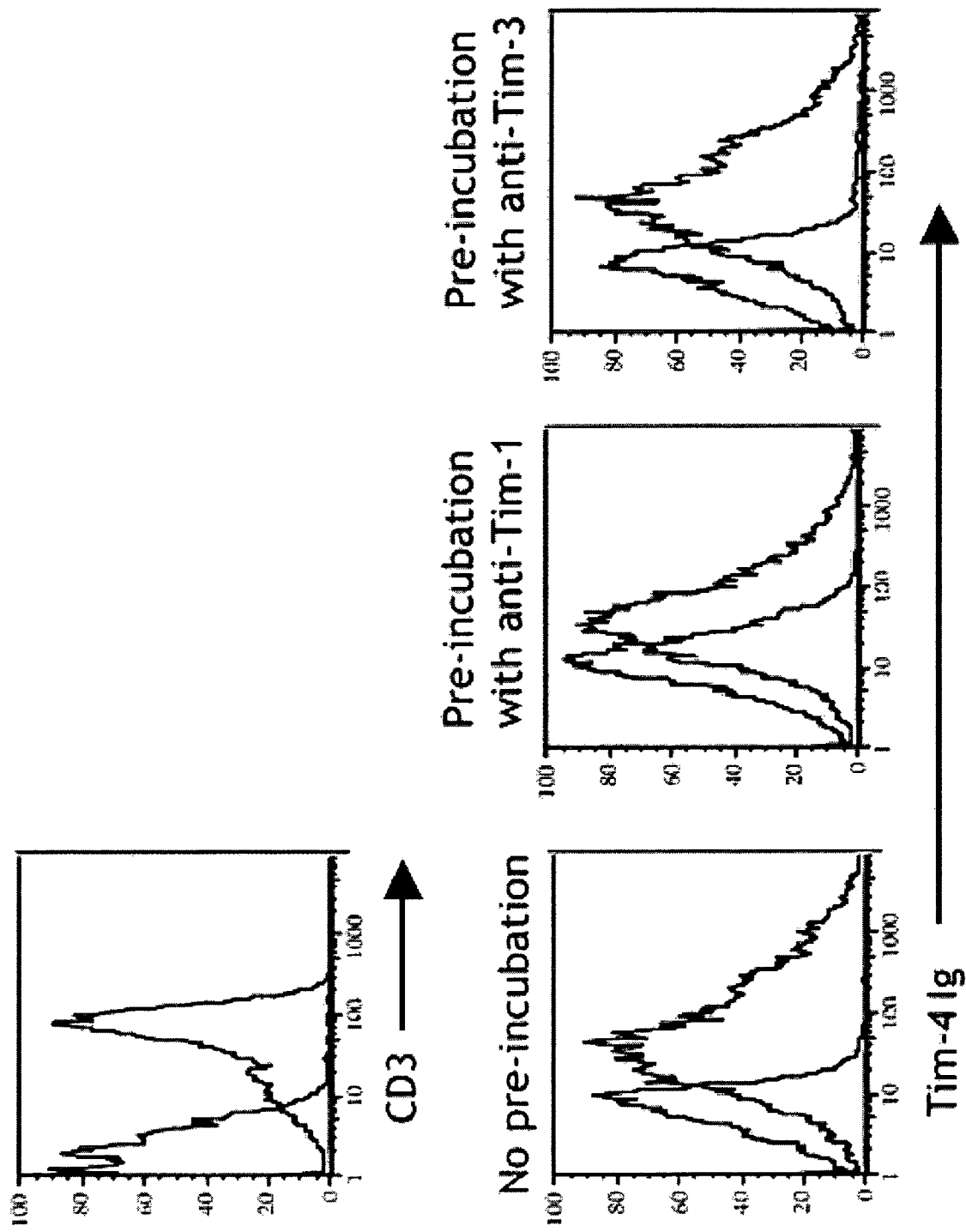

After observing an in vitro interaction between Tim-4 and Tim-1 on transfected cells, applicants wanted to determine whether such an interaction could also occur with naturally expressed Tim-1 on T cells. As applicants had previously observed that Tim-4-Ig stained activated T cells (FIG. 13), CD3$^+$ T cells from naïve SJL/J mice were activated and then assessed for expression of Tim-1 and its ability to bind to Tim-4-Ig. Tim-1 was minimally expressed in unactivated T cells and was upregulated in T cells upon activation (FIG. 15A). This pattern of Tim-1 expression was consistent with that observed by others. Binding of Tim-4-Ig to these T cells directly correlated with Tim-1 expression, in that Tim-4-Ig stained activated but not unactivated T cells. This binding of Tim-4-Ig to activated T cells was partially blocked by anti-Tim-1 but not by anti-Tim-3 (FIG. 15B). As seen with the Tim-1 transfectants, blocking of Tim-4-Ig binding to activated T cells was not complete. This further supports the notion that, in addition to the IgV, the Tim-1 mucin domain is also involved in the Tim-1-Tim-4 interaction, so an antibody binding only the IgV domain could not completely prevent binding of Tim-4-Ig to Tim-1 on activated T cells.

Figure 15C:
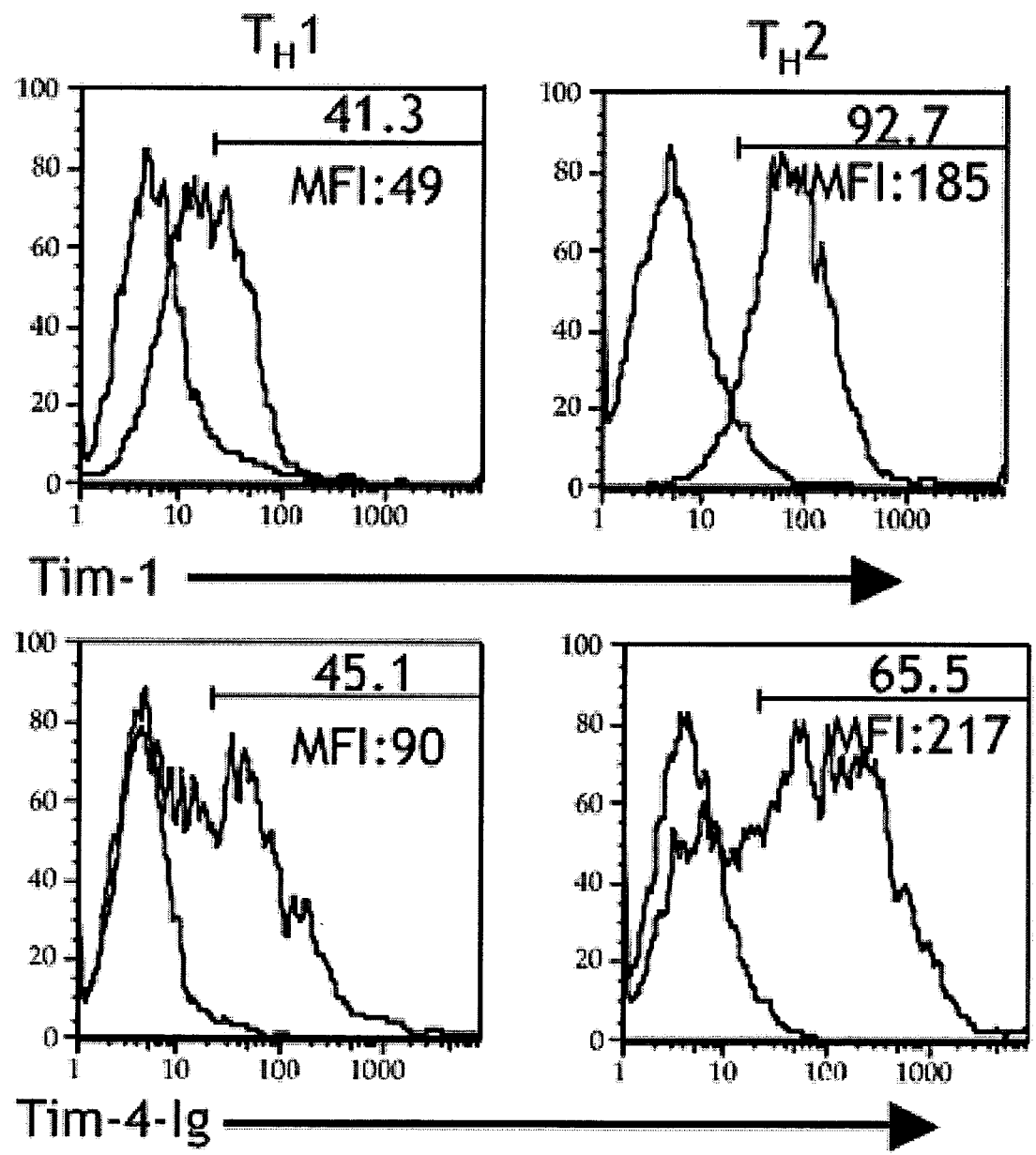
Figure 15D:
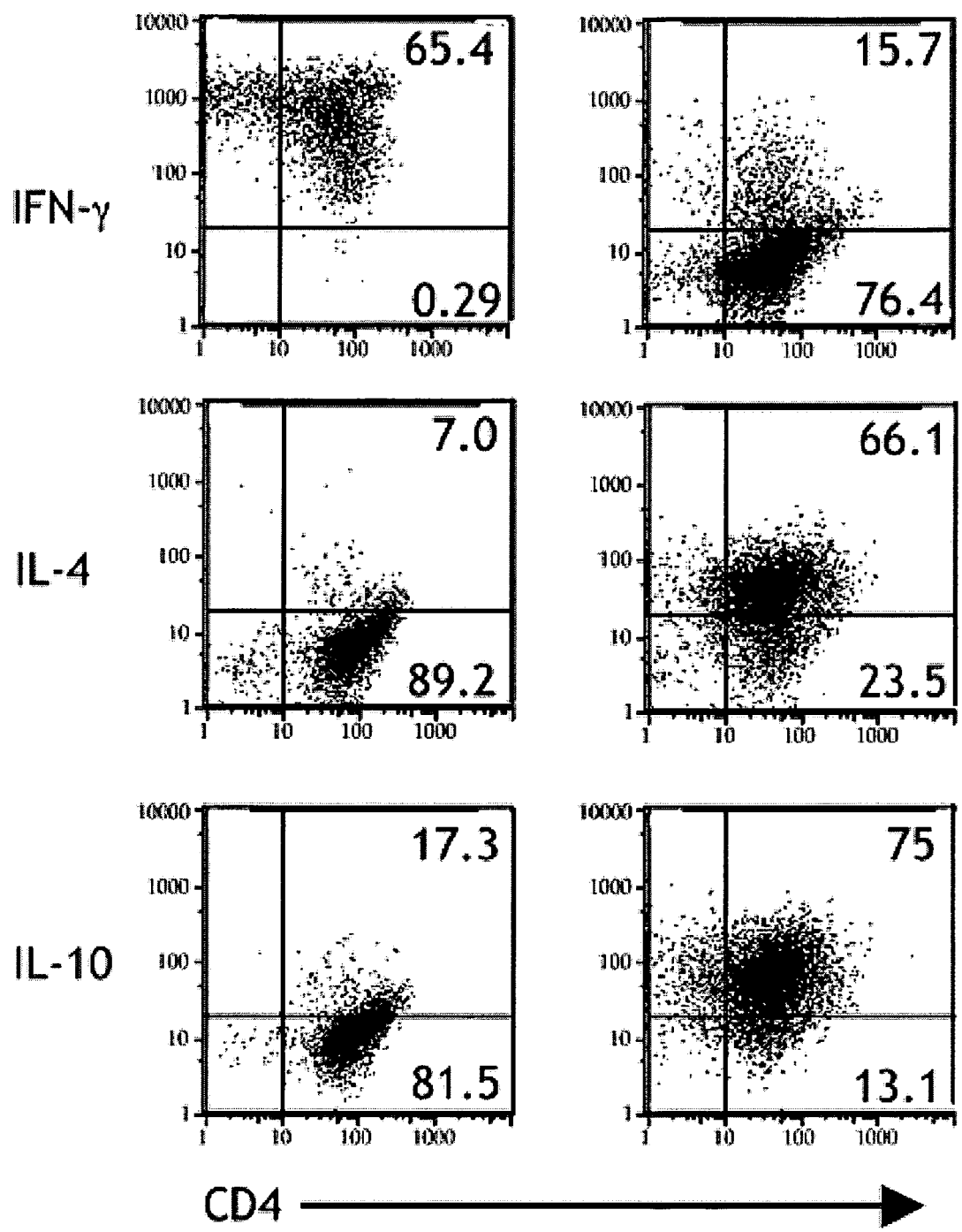

Given the apparent interaction between Tim-4 and Tim-1 on activated T cells, applicants sought to determine whether this interaction occurs preferentially on activated $T_H1$ or $T_H2$ cells. To this end, applicants tested the binding of Tim-4-Ig on activated, in vitro-polarized DO11.10 TCR transgenic $T_H1$ and $T_H2$ cells and examined these cells for expression of Tim-1 in parallel. Although Tim-1 was expressed on both activated $T_H1$ and $T_H2$ cells, it was expressed more highly on activated $T_H2$ versus $T_H1$ cells (FIGS. 15C and 15D). Consistent with the Tim-1 expression, Tim-4-Ig stained higher proportions of $T_H2$ cells than $T_H1$ cells. Successful polarization of these cells into $T_H1$ and $T_H2$ subsets was confirmed by intracellular staining, which demonstrated that polarized TH 1 cells produced large amounts of IFN-γ with very little interleukin (IL)-4 or IL-10; in contrast, $T_H2$ cells produced large amounts of IL-4 and IL-10 but little IFN-γ (FIGS. 15C and 15D). These data demonstrated that Tim-4-Ig could bind activated T cells, and that upon polarization there was higher binding on $T_H2$ than on $T_H1$ cells.

EXAMPLE 14

Expression of Tim-1L on Dendritic Cells and Macrophages

Figure 16:
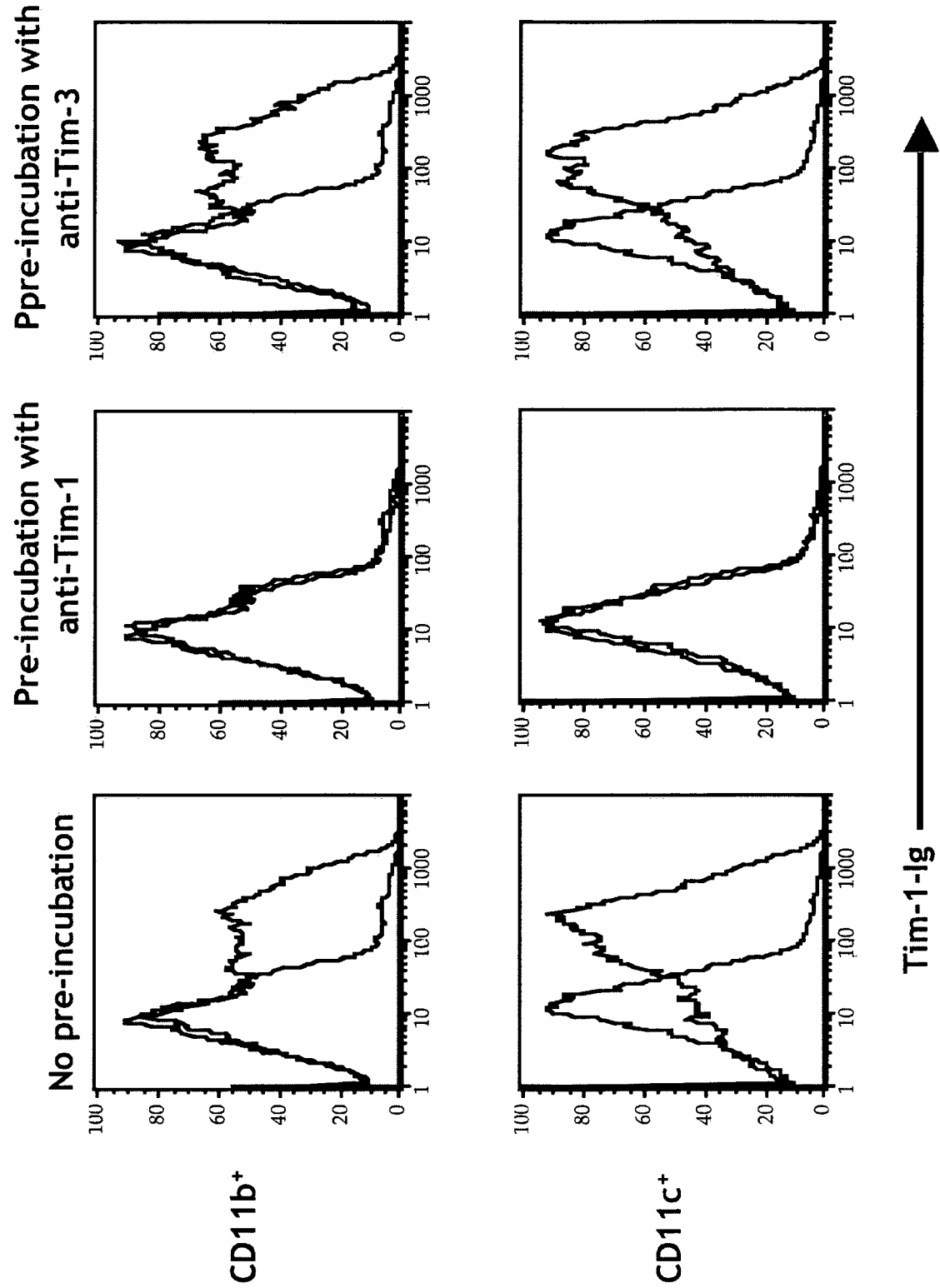
FIG. 16 shows Tim-1-Ig specifically binds activated $CD11b^+$ and $CD11c^+$ cells ex vivo. Splenocytes from DO11.10 TcR transgenic mice or Balb/c mice were stimulated with LPS and IFN-γ. $CD11b^+$ and $CD11c^+$ cells were purified by MACS column purification and stained with biotinylated Tim-1-Ig in the presence or absence of anti-Tim-1 or anti-Tim-3 monoclonal antibodies. Streptavidin-PE was used as a secondary detection reagent. Data is representative of 2 experiments.

Because Tim-4 is expressed in macrophages and DCs but not T cells, applicants analyzed whether soluble Tim-1-Ig would bind normal, in vivo-derived macrophages and DCs. Indeed, in vivo-derived macrophages and DCs (purified CD11b$^+$ and CD11c$^+$ splenic subsets) specifically bound to Tim-1-Ig following activation with LPS and IFN-γ. In contrast, no purified T cell population examined (CD4$^+$ or CD8$^+$), whether unactivated or activated, bound Tim-1-Ig. To ensure that the observed staining was specific, applicants undertook blocking studies with anti-Tim-1, using anti-Tim-3 as a control. Pre-incubation of Tim-1-Ig with anti-Tim-1 inhibited the staining observed on activated CD11b$^+$ and CD11c$^+$ cells (FIG. 16). No inhibition of staining was observed by pre-incubation with anti-Tim-3, confirming that the staining observed was due to a specific interaction between Tim-1 and macrophages and DCs expressing its ligand. These studies demonstrated that Tim-1 and Tim-4 not only interacted when binding was examined on in vitro-derived CHO transfectants, but that Tim-4-Ig bound strongly on activated $T_H2$ cells (although weaker binding to $T_H1$ cells was also observed), while Tim-1-Ig bound in vivo-derived activated macrophages and DCs.

EXAMPLE 15

In Vivo Tim-1-Ig Administration Augments Th2 Responses

Since Tim-1 is expressed on all activated T cells, applicants hypothesized that the Tim-1-Tim-4 interaction may serve to regulate expansion and effector functions of all T cells. However, this effect may be greater on $T_H2$ cells, because Tim-1 is more highly expressed on $T_H2$ cells than on $T_H1$ cells. Tim-1 is expressed in many tissues, and its intracellular tail contains putative tyrosine phosphorylation motifs, whereas Tim-4 mRNA expression is restricted mainly to spleen and lymph node, and its tail lacks putative signaling motifs. Therefore, applicants chose to treat mice with soluble Tim-1-Ig, which would be expected to specifically bind to Tim-4 on the surface of APCs and either co-cluster Tim-4 and enhance the signal delivered to T cells via Tim-1, or block the interaction between Tim-1 and Tim-4. To investigate the functional impact of administering Tim-1-Ig during an in vivo immune response, applicants tested the effects of Tim-1-Ig treatment on the T cell response in SJL/J mice immunized with proteolipid polypeptide (PLP) 139-151 peptide, which induces potent $T_H1$ responses.

Figure 17A:
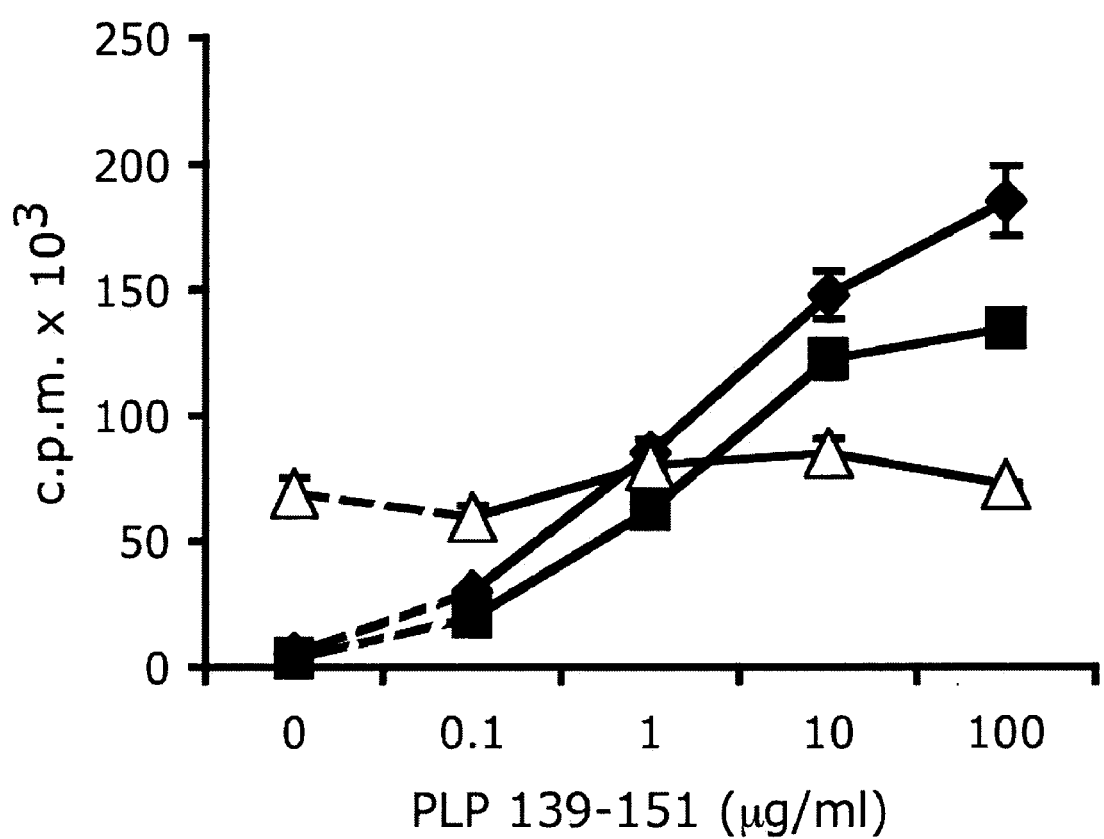
FIG. 17 shows administration of Tim-1-Ig results in T cell hyperproliferation. (a) Spleen cells from immunized SJL/J mice treated in vivo with Tim-1-Ig, or hIgG or PBS as controls, were cultured in vitro for 48 h with PLP139-151 peptide restimulation. Proliferation was measured in triplicate wells after 48 h by $^3$[H]thymidine incorporation. (b) Culture supernatants from the experiment described in 6a were taken after 48 h culture with PLP 139-151 antigenic stimulation in vitro and used in cytokine ELISAs; IL-2, IL-4, IL-10 and IFN-γ production are shown. Splenocytes from individual mice (n=6) were analyzed separately, and mean data for all mice is shown. Error bars represent S.E.M. values. Data are representative of 4 separate experiments. Black diamond, PBS; black square, hIgG; open triangle, Tim-1-Ig treated.

SJL/J mice immunized with PLP 139-151 peptide emulsified in Complete Freund's Adjuvant (CFA) were administered with Tim-1-Ig or control reagents (PBS or human IgG1). Spleen cells from immunized and treated mice were tested in vitro for proliferative and cytokine responses. Spleen cells from mice immunized and treated with control human IgG1 (hIgG) or PBS demonstrated little background proliferation in the absence of antigen. In contrast, cells from Tim-1-Ig-treated mice showed a pronounced basal proliferation even in the absence of in vitro antigenic restimulation (FIG. 6a). Upon restimulation with PLP antigen, cells from both control groups demonstrated specific dose-dependent proliferation to PLP 139-151. However, spleen cells from Tim-1-Ig-treated mice showed only a modest increase in proliferation over the background upon addition of antigen (FIG. 17A). Similarly high background proliferation was observed from mice immunized with CFA alone without any peptide and treated with Tim-1-Ig, indicating that this proliferative response was not limited to a specific antigen. These data suggest that treatment with Tim-1-Ig results in the hyperactivation of cells in vivo, such that the cells continue to proliferate in vitro without antigenic stimulation.

Figure 17B:
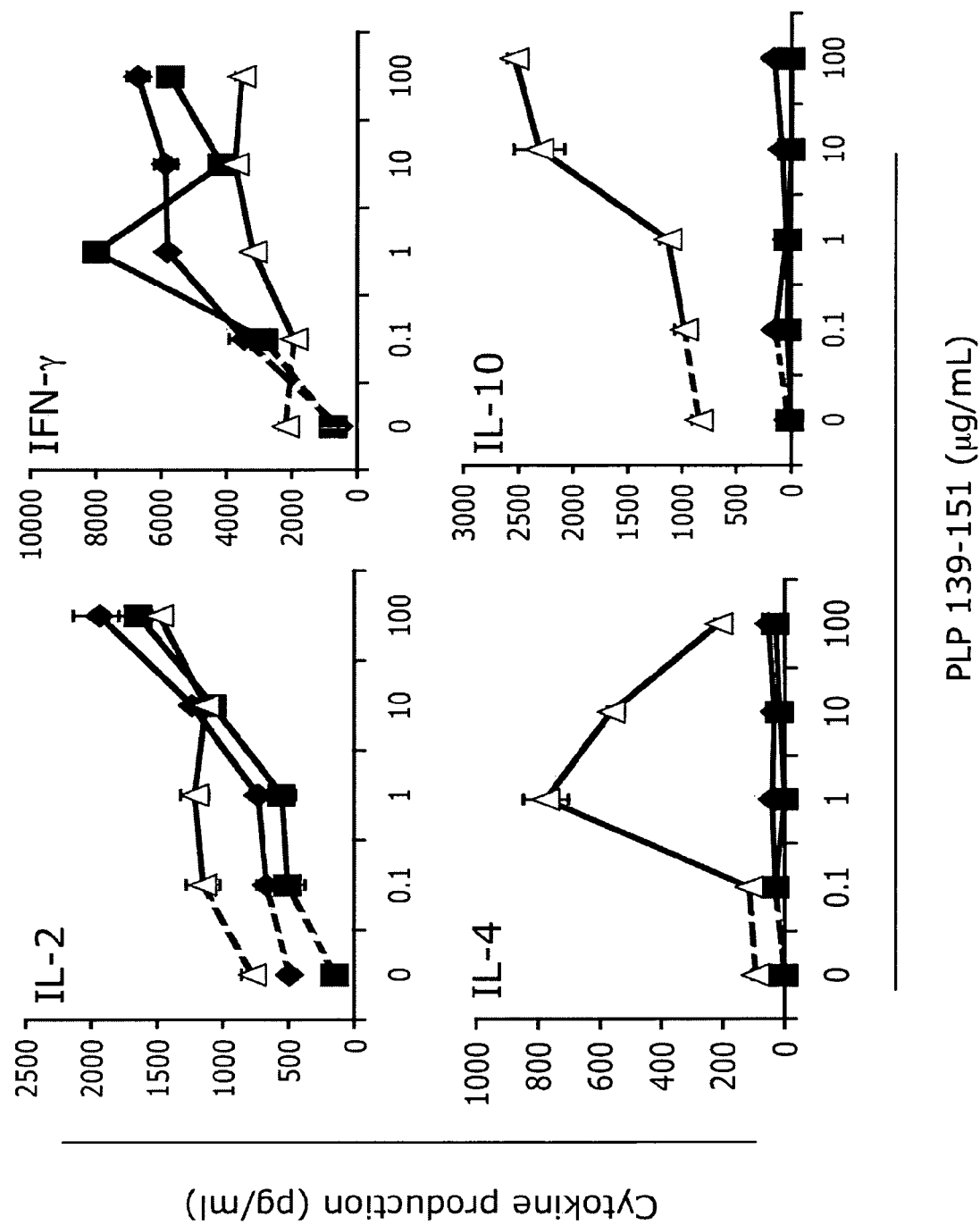

Supernatants from these experiments were analyzed for the production of IL-2, IFN-γ, IL-4, and IL-10 by ELISA. Spleen cells from Tim-1-Ig-treated mice secreted high quantities of IL-2 in the absence of antigenic stimulation, which was consistent with the high basal proliferation observed. Large amounts of IL-10 and IFN-γ were also produced without reactivation, while spleen cells from immunized, control (hIgG and PBS)-treated mice demonstrated much lower background cytokine production in the absence of in vitro antigenic stimulation. Though only a small amount of IL-4 was produced from Tim-1-Ig-treated cells without reactivation, none was detectable from control-treated cells. This may be due to the fact that immunization of SJL/J mice with the PLP peptide induces potent $T_H1$ responses and inhibits $T_H2$ responses. Upon restimulation with PLP 139-151 in vitro, cells from control treated mice demonstrated the expected TH 1 profile with the production of IL-2 and IFN-γ (FIG. 17B). The spleen cells from Tim-1-Ig treated mice continued to produce IL-2 upon restimulation, again consistent with the continued, non-dose-dependent proliferation observed from these cells (FIG. 17C). In contrast to cells from control-treated mice, spleen cells from Tim-1-Ig-treated mice produced large quantities of IL-4 and IL-10 upon antigenic restimulation, indicating that Tim-1-Ig treatment preferentially expanded $T_H2$ cells upon reactivation. Whereas immunization of SJL/J mice with the encephalitogenic PLP peptide resulted in the induction of $T_H1$ cells and cytokines (as seen in the PBS and hIgG-treated control mice), treatment with Tim-1-Ig inhibited antigen-specific IFN-γ production (FIG. 17B). SJL/J mice immunized with PLP139-151 in CFA develop a profound $T_H1$ response, and Tim-1-Ig administered in this setting resulted in the production of $T_H2$ cytokines (IL-4 and IL-10) with inhibition of IFN-γ production.

Figure 19A:
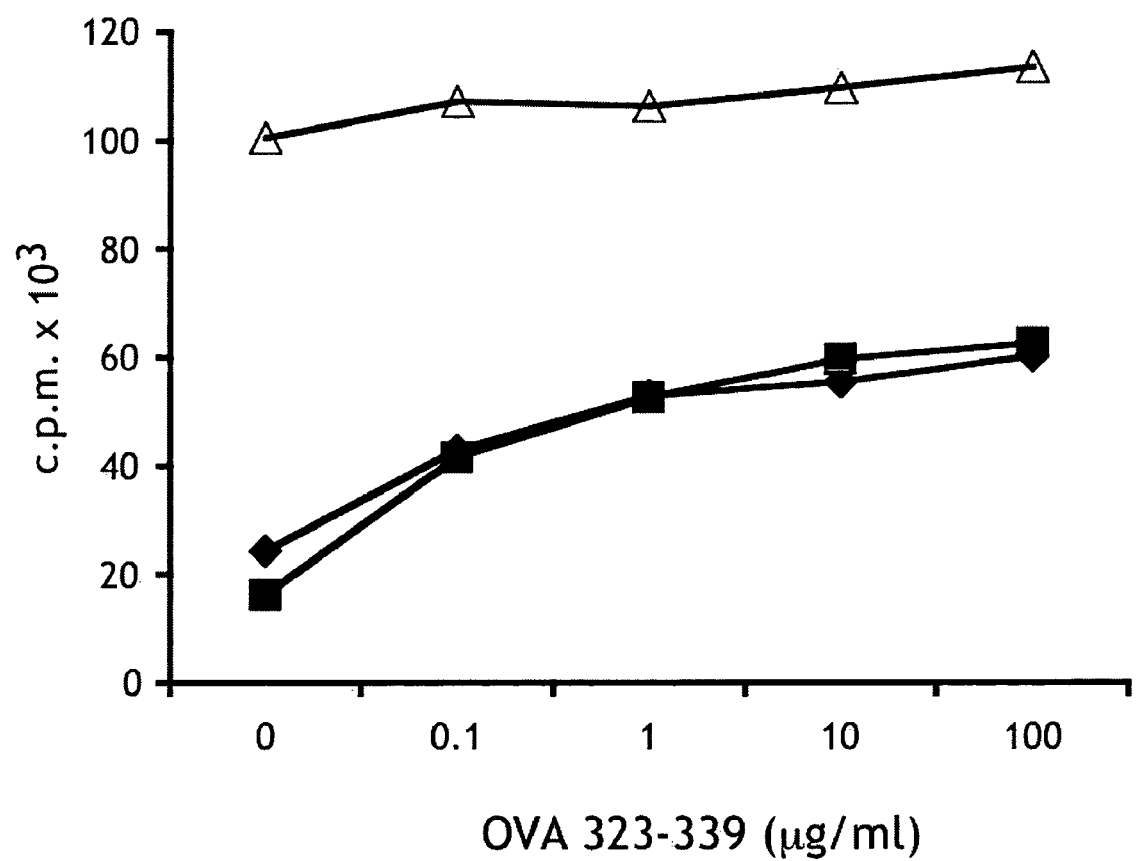
FIG. 19 shows Tim-1-Ig administration in vivo induces hyperproliferation and enhancement of the $T_H2$ response in a $T_H2$-biased system. Female Balb/c mice were injected i.p. with 50 µg OVA 323-339 and 4 mg Imject alum (Pierce) and then boosted i.p. with 50 µg OVA 323-339 and 2 mg alum 7 days later. Mice were injected i.p. five times with 100 μg Tim-1-Ig, hIgG, or 250 μl PBS: 4 h before immunization and 4 h before the day 7 boost, as well as days 2, 4, and 10 following immunization. On day 14, mice were sacrificed and splenocytes were assayed for proliferation and cytokines. (a) Splenocytes were cultured in vitro for 48 h with OVA 323-339 peptide. Proliferation was measured after 48 h by ³[H]thymidine incorporation in triplicate wells. (b) Culture supernatants were taken 48 h post OVA 323-339 restimulation in vitro and used in cytokine ELISAs; IL-2, IL-4, and IL-10 production are shown. No significant IFN-γ production was observed. Splenocytes from individual mice (n=3) were separately analyzed in triplicate wells, and mean values for all 3 mice are shown. Black squares, PBS; black diamonds, hIgG; open triangles, Tim-1-Ig treatment in vivo.
Figure 19B:
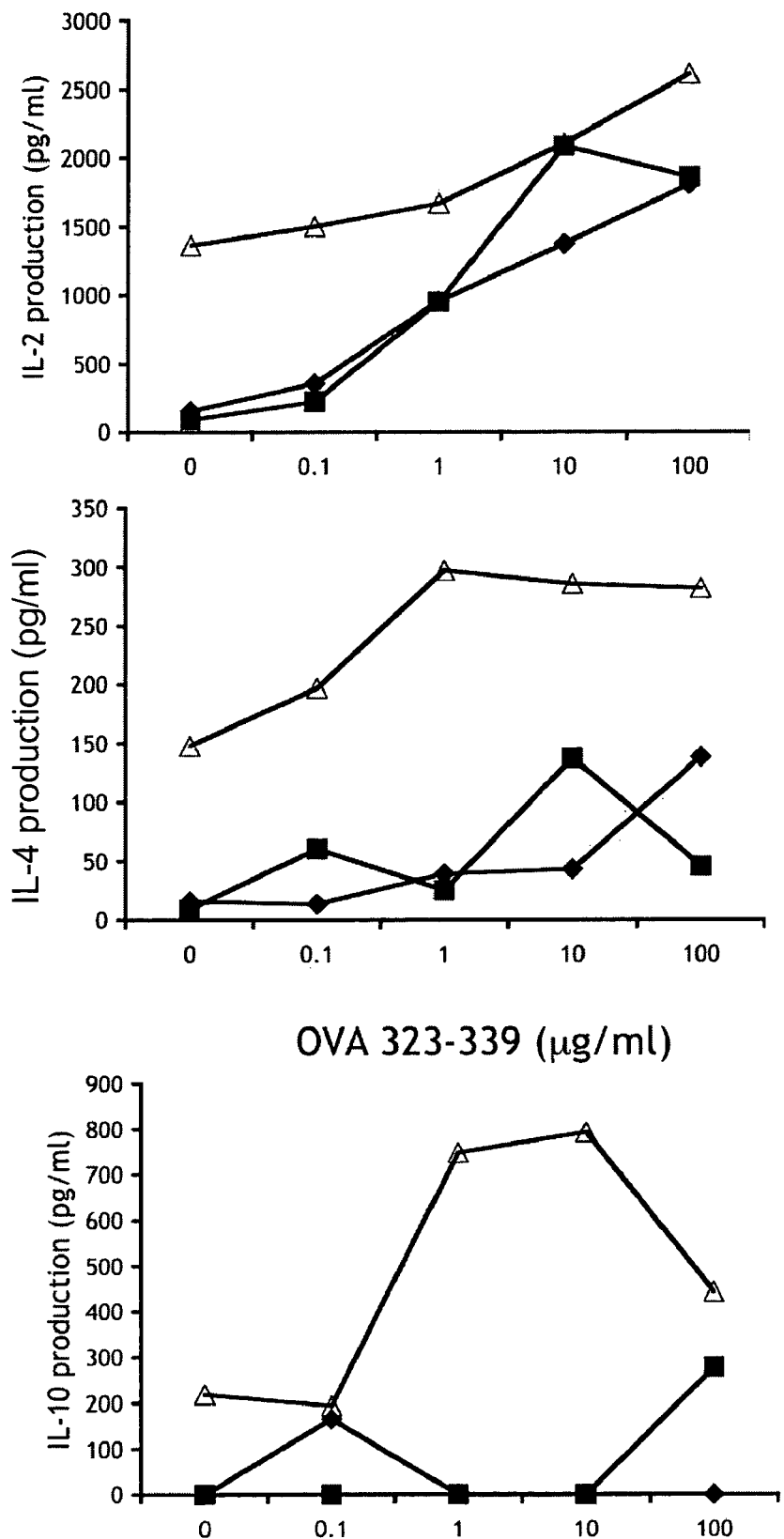

To determine whether this was also true in a $T_H2$-biased immune response, applicants immunized Balb/c mice with OVA 323-339 peptide in alum and administered Tim-1-Ig as above. Under these $T_H2$ biased conditions, Tim-1-Ig also enhanced basal proliferation with increased production of IL-2, IL-4 and IL-10 cytokines but no increase in IFN-γ (FIG. 19). Taken together, these results suggest Tim-1-Ig affected the Tim-1-Tim-4 interaction in vivo, resulting in hyperactivation of T cells such that they continued to proliferate ex vivo and produce both $T_H1$ (IL-2 and IFN-γ) and $T_H2$ (IL-4 and IL-10) cytokines. Although spleen cells from Tim-1-Ig-treated mice without antigenic restimulation continued to produce significant amounts of IL-2, IFN-γ, and IL-10, reactivation of these cells with antigen in vitro resulted in inhibition of $T_H1$ responses and expansion of $T_H2$ cells, even in a $T_H1$-biased immunization protocol. Whether this was because of preferential deletion of $T_H1$ cells due to activation-induced cell death or expansion of $T_H2$ cells remains to be determined. From this data, it was unclear whether Tim-1 was delivering a negative or positive signal in vivo, i.e., whether Tim-1-Ig was blocking a negative interaction or promoting a positive interaction between Tim-1 and Tim-4. Applicants therefore used Tim-4-Ig, which binds Tim-1, to determine what effect a reagent directly binding to Tim-1 might have in vivo and in vitro.

EXAMPLE 16

Tim-4-Ig Costimulates T Cell Expansion

Figure 18A:
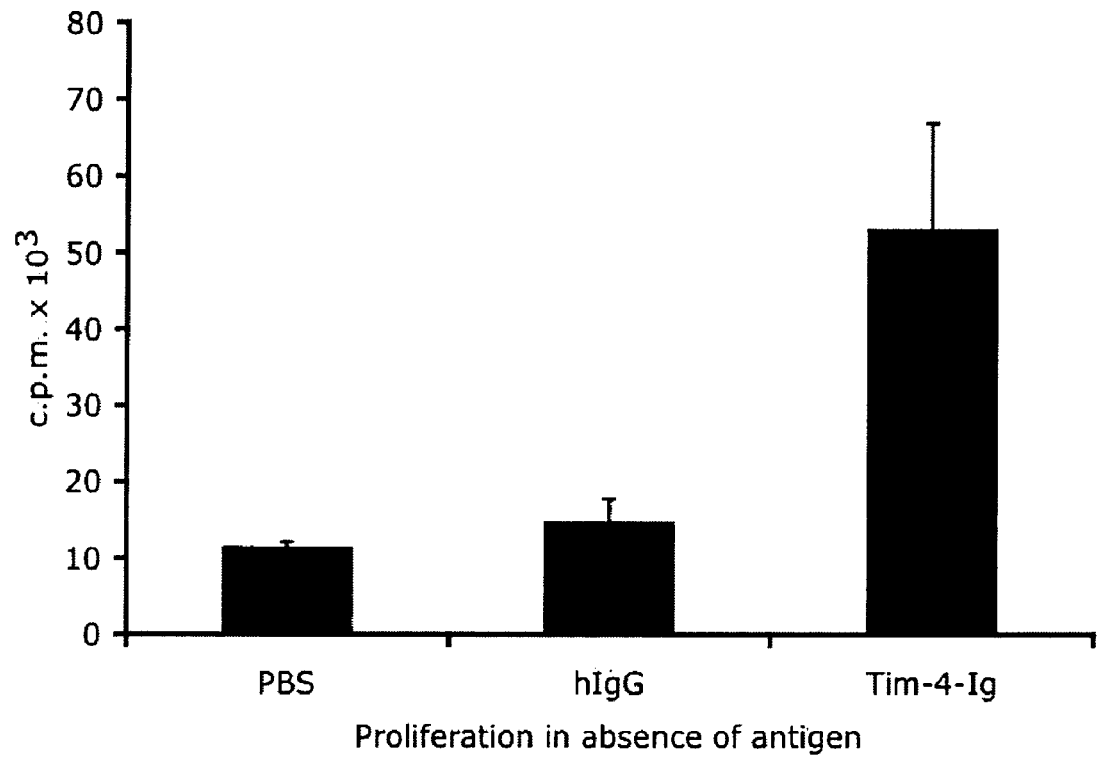
FIG. 18 shows Tim-4-Ig induces hyperproliferation of T cells in vivo and costimulates T cell proliferation in vitro. (a) Spleen cells from immunized SJL/J mice treated in vivo with Tim-4-Ig, or hIgG or PBS as controls, were cultured in vitro for 48 h without peptide restimulation. Proliferation was measured in triplicate wells after 48 h by $^3$[H]thymidine incorporation. Supernatants from these wells were taken after 48 h culture without peptide restimulation in vitro and used in cytokine ELISAs to test the amount of cytokine produced spontaneously without antigenic restimulation. Splenocytes from 2 different mice were each analyzed in triplicate, and mean values are shown. (b) Spleen cells pooled from 2 immunized SJL/J mice treated in vivo with Tim-4-Ig (T4) or hIgG (Hu) were separated into $CD11b^+$ (Mac), $B220^+$ (B), and $CD3^+$ (T) populations and recombined without peptide restimulation. Proliferation was measured after 48 h by $^3$[H] thymidine incorporation. (c) Purified SJL/J T cells were stimulated on plates coated with anti-CD3, anti-CD28, and Tim-4-Ig or control Igs at the indicated concentrations. Proliferation was measured after 48 h by $^3$[H]thymidine incorporation in triplicate wells. Data are representative of 2 identical experiments (left panel) or 5 identical experiments (right panel). All error bars represent S.E.M. values from replicate wells.
Figure 18A:
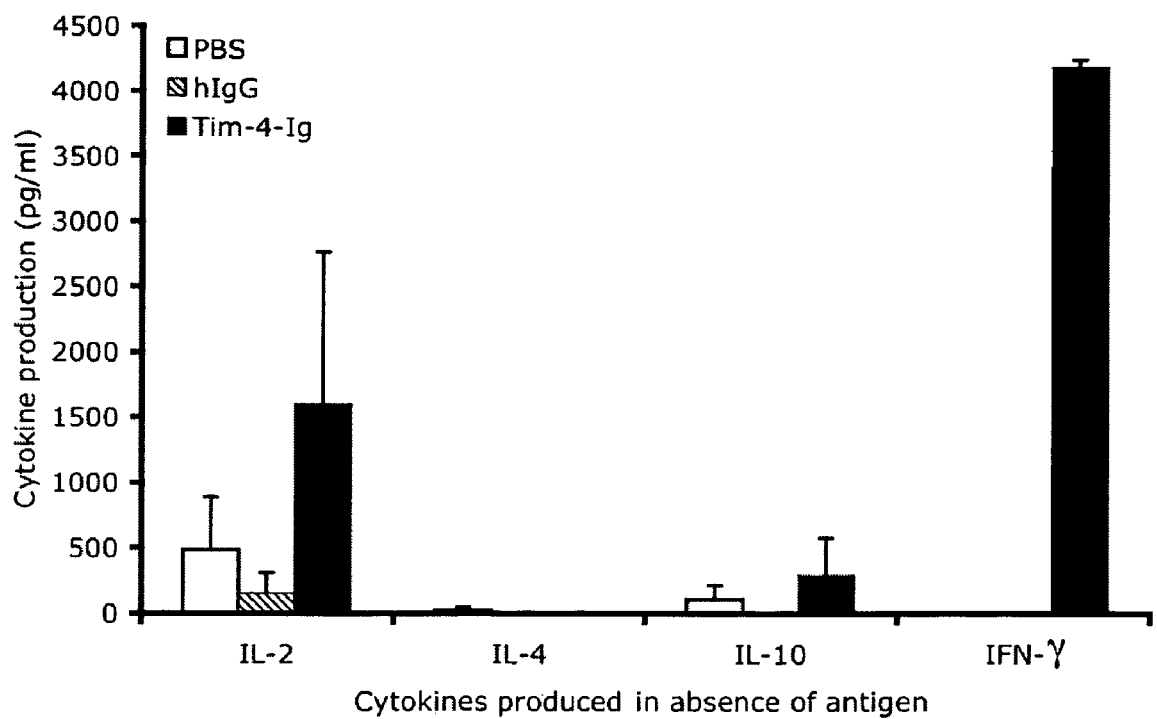
Figure 18B:
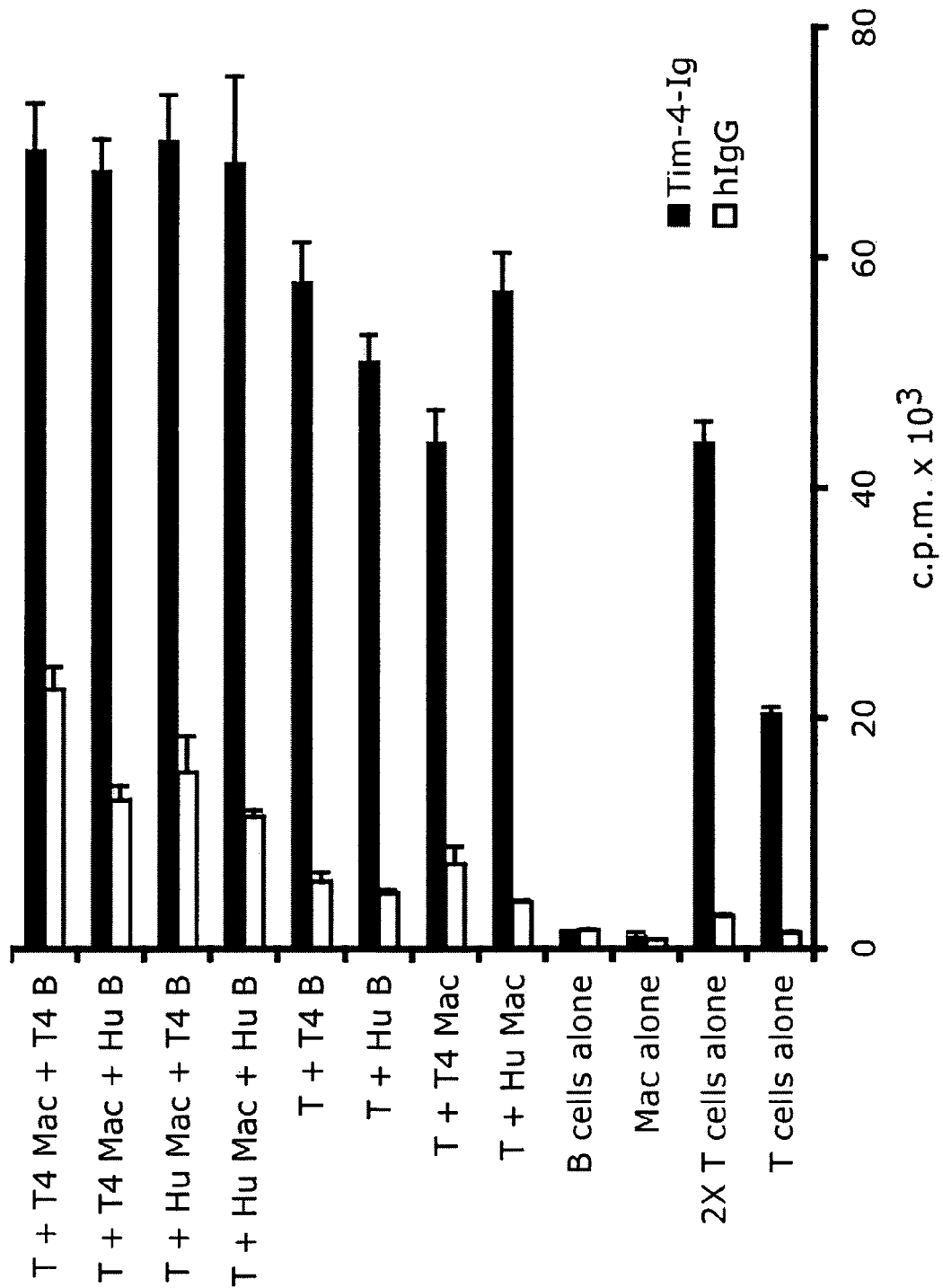

To determine whether Tim-4-Ig could stimulate or inhibit T cell proliferation and cytokine production, applicants treated SJL/J mice immunized with PLP 139-151 in CFA with Tim-4-Ig, hIgG, or PBS as above. Spleen cells from treated mice were again tested in vitro for proliferative and cytokine responses. Similarly to Tim-1-Ig-treated splenocytes, Tim-4-Ig-treated splenocytes showed high basal proliferation in the absence of antigenic restimulation (FIG. 18A). In addition, Tim-4-Ig-treated splenocytes produced large amounts of IL-2 and IFN-γ but small concentrations of IL-4 and IL-10 without restimulation. Since Tim-4 binds Tim-1, which is expressed on T cells, applicants wondered whether the high background proliferation was due to hyperproliferating T cells or other cell types. To determine the identity of the cells responsible for this high background response, applicants separated Tim-4-Ig and hIgG-treated splenocytes into CD11b$^+$, B220$^+$, and CD3$^+$ populations and then either cultured them alone or recombined them in vitro and measured their ability to proliferate without antigenic restimulation. The Tim-4-Ig-treated but not hIgG-treated T cells proliferated in the absence of APCs, and no APC population proliferated alone (FIG. 18B). However, when Tim-4-Ig-treated T cells were combined with any of the APC populations, even higher proliferation was detected. This increase in T cell proliferation was not dependent on the source of APCs, because APCs from either Tim-4-Ig or hIgG-treated mice were able to induce comparable amounts of T cell proliferation. Similar proliferative responses were not observed from any cultures containing hIgG-treated T cells. This data indicated that the hyperproliferation by Tim-4-Ig-treated splenocytes was entirely due to the effect of Tim-4-Ig on T cells.

Figure 18C:
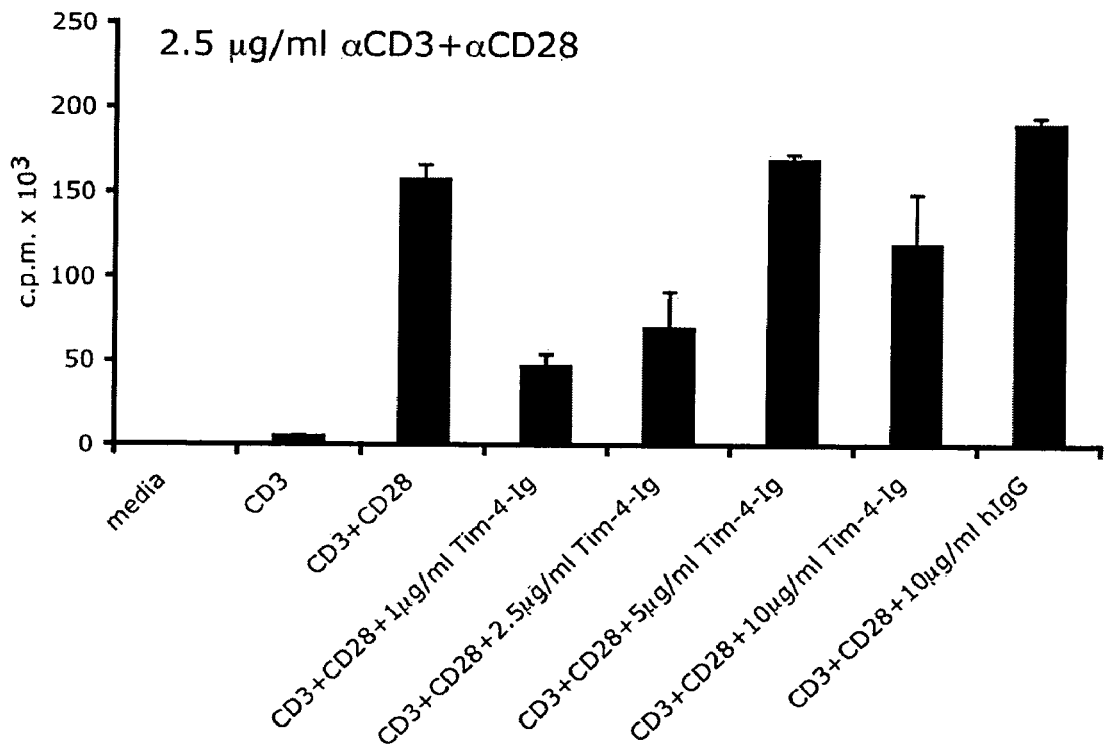
Figure 18C:
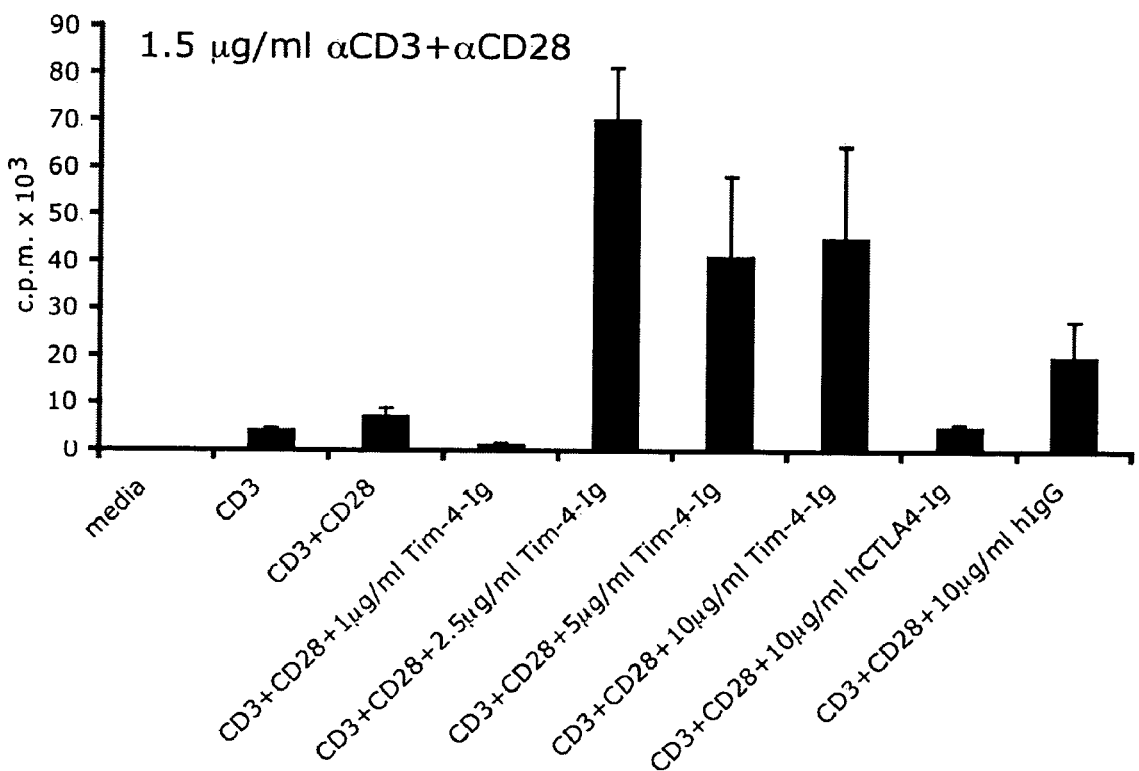

After determining that the T cells were the population most affected by Tim-4-Ig, applicants assessed whether Tim-4-Ig could directly costimulate T cells in vitro. Purified SJL/J CD3$^+$ T cells were stimulated with anti-CD3 and anti-CD28 along with Tim-4-Ig (or hIgG or hCTLA4-Ig as controls). As Tim-4-Ig binds to Tim-1 on T cells and no APCs were present in the system, there was no natural Tim-4-Tim-1 interaction to be blocked; therefore, any effects observed would be expected to be mediated through Tim-1 signaling into T cells. Interestingly, applicants observed qualitatively different outcomes depending on the concentration of Tim-4-Ig used. If the T cells were stimulated suboptimally with anti-CD3 plus anti-CD28 (FIG. 18C, left panel), applicants observed a massive increase in proliferation upon addition of Tim-4-Ig. Applicants also observed a slight inhibition of proliferation at low concentrations of Tim-4-Ig (p=0.03). Addition of control hIgG or hCTLA4-Ig showed little effect on anti-CD3 plus anti-CD28-mediated proliferation. Also, Tim-4-Ig did not alter proliferation when combined with anti-CD3 alone, indicating that it required both CD3 and CD28 signaling to stimulate T cell expansion. To determine whether Tim-4-Ig truly inhibited T cell proliferation at low concentrations, purified CD3$^+$ T cells were stimulated with a higher concentration of anti-CD3 plus anti-CD28 (FIG. 18C, right panel) and again assayed to determine how Tim-4Ig would affect T cell expansion. Anti-CD3 plus anti-CD28 alone induced a high amount of proliferation from these T cells, and addition of lower concentrations of Tim-4-Ig strongly inhibited this proliferation (p=0.007). At higher concentrations of Tim-4-Ig, proliferation returned to normal or was enhanced over that observed with anti-CD3 plus anti-CD28 alone (FIG. 18C). Overall, it is clear that Tim-4-Ig can costimulate T cell proliferation, most likely by crosslinking its ligand on T cells and delivering an activating signal.

Sequence Listings

SEQ ID NO: 1; Tim-1 Human Polypeptide (NP_036338)

MRPQVVILSLILHLADSVAGSVKVGGEAGPSVTLPCHYSGAVTSMCWNRG

SCSLFTCQNGIVWTNGTHVTYRKDTRYKLLGDLSRRDVSLTIENTAVSDS

GVYCCRVEHRGWFNDMKITVSLEIVPPKVTTTPIVTTVPTVTTVRTSTTV

PTTTTVPTTTVPTTMSIPTTTTVPTTMTVSTTTSVPTTTSIPTTTSVPVT

TTVSTFVPPMPLPRQNHEPVATSPSSPQPAETHPTTLQGAIRREPTSSPL

YSYTTDGNDTVTESSDGLWNNNQTQLFLEHSLLTANTTKGIYAGVCISVL

VLLALLGVIIAKKYFFKKEVQQLSVSFSSLQIKALQNAVEKEVQAEDNIY

IENSLYATD

SEQ ID NO: 2; Tim-1 Mouse Polypeptide (NP_599009)

MNQIQVFISGLILLLPGTVDSYVEVKGVVGHPVTLPCTYSTYRGITTTCW

GRGQCPSSACQNTLIWTNGHRVTYQKSSRYNLKGHISEGDVSLTIENSVE

SDSGLYCCRVEIPGWFNDQKVTFSLQVKPEIPTRPPTRPTTTRPTATGRP

TTISTRSTHVPTSIRVSTSTPPTSTHTWTHKPEPTTFCPHETTAEVTGIP

SHTPTDWNGTVTSSGDTWSNHTEAIPPGKPQKNPTKGFYVGICIAALLLL

LLVSTVAITRYILMKRKSASLSVVAFRVSKIEALQNAAVVHSRAEDNIYI

VEDRP

SEQ ID NO: 3; Tim-4 Human Polypeptide Variant #1

MSKEPLILWLMIEFWWLYLTPVTSETVVTEVLGHRVTLPCLYSSWSHNSN

SMCWGKDQCPYSGCKEALIRTDGMRVTSRKSAKYRLQGTIPRGDVSLTIL

NPSESDSGVYCCRIEVPGWFNDVKINVRLNLQRASTTTHRTATTTTRRTT

TTSPTTTRQMTTTPAALPTTVVTTPDLTTGTPLQMTTIAVFTTANTCLSL

TPSTLPEEATGLLTPEPSKEGPILTAESETVLPSDSWSSAESTSADTVLL

TSKESKVWDLPSTSHVSMWKTSDSVSSPQPGASDTAVPEQNKTTKTGQMD

GIPMSMKNEMPISQLLMIIAPSLGFVLFALFVAFLLRGKLMETYCSQKHT

RLDYIGDSKNVLNDVQHGREDEDGLFTL

SEQ ID NO: 4; Tim-4 Mouse Polypeptide

MSKGLLLLWLVMELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAITTESETLPASNHSQRSMMTISTDIAVLRPTGSNPGILPSTS

QLTTQKTTLTTSESLQKTTKSHQINSRQTILIIACCVGFVLMVLLFLAFL

LRGKVTGANCLQRHKRPDNTEDSDSVLNDMSHGRDDEDGIFTL

SEQ ID NO: 5; Tim-1 Human Nucleic Acid (NM_012206)
GTTACCCAGCATTGTGAGTGACAGAGCCTGGATCTGAACGCTGATCCCAT

AATGCATCCTCAAGTGGTCATCTTAAGCCTCATCCTACATCTGGCAGATT

CTGTAGCTGGTTCTGTAAAGGTTGGTGGAGAGGCAGGTCCATCTGTCACA

CTACCCTGCCACTACAGTGGAGCTGTCACATCAATGTGCTGGAATAGAGG

CTCATGTTCTCTATTCACATGCCAAAATGGCATTGTCTGGACCAATGGAA

CCCACGTCACCTATCGGAAGGACACACGCTATAAGCTATTGGGGGACCTT

TCAAGAAGGGATGTCTCTTTGACCATAGAAAATACAGCTGTGTCTGACAG

TGGCGTATATTGTTGCCGTGTTGAGCACCGTGGGTGGTTCAATGACATGA

AAATCACCGTATCATTGGAGATTGTGCCACCCAAGGTCACGACTACTCCA

ATTGTCACAACTGTTCCAACCGTCACGACTGTTCGAACGAGCACCACTGT

TCCAACGACAACGACTGTTCCAACGACAACTGTTCCAACAACAATGAGCA

TTCCAACGACAACGACTGTTCCGACGACAATGACTGTTTCAACGACAACG

AGCGTTCCAACGACAACGAGCATTCCAACAACAACAAGTGTTCCAGTGAC

AACAACGGTCTCTACCTTTGTTCCTCCAATGCCTTTGCCCAGGCAGAACC

ATGAACCAGTAGCCACTTCACCATCTTCACCTCAGCCAGCAGAAACCCAC

CCTACGACACTGCAGGGAGCAATAAGGAGAGAACCCACCAGCTCACCATT

GTACTCTTACACAACAGATGGGAATGACACCGTGACAGAGTCTTCAGATG

GCCTTTGGAATAACAATCAAACTCAACTGTTCCTAGAACATAGTCTACTG

ACGGCCAATACCACTAAAGGAATCTATGCTGGAGTCTGTATTTCTGTCTT

GGTGCTTCTTGCTCTTTTGGGTGTCATCATTGCCAAAAAGTATTTCTTCA

AAAAGGAGGTTCAACAACTAAGTGTTTCATTTAGCAGCCTTCAAATTAAA

GCTTTGCAAAATGCAGTTGAAAAGGAAGTCCAAGCAGAAGACAATATCTA

CATTGAGAATAGTCTTTATGCCACGGACTAAGACCCAGTGGTGCTCTTTG

AGAGTTTACGCCCATGACTGCAGAAGACTGAACAGGTATCAGCACATCAG

ATGTCTTTTAGACTCCAAGACAATTTTTCTGTTTCAGTTTCATCTGGCAT

TCCAACATGTCAGTGATACTGGGTAGAGTAACTCTCCCACTCCAAACTGT

GTATAGTCAACCTCATCATTAATGTAGTCCTAATTTGTTTTGCTAAAACT

GGCTCAATCCTTCTGATCATTGCAGAGTTTTCTCTCAAACATGAACACTT

TAGAATTGTATGTTCTCTTTAGACCCCATAAATCCTGTAT

SEQ ID NO: 6; Tim-1 Mouse Nucleic Acid (NM_134248)
ATGAATCAGATTCAAGTCTTCATTTCAGGCCTCATACTGCTTCTCCCAGG

CACTGTGGATTCTTATGTGGAAGTAAAGGGGGTAGTGGGTCACCCTGTCA

CACTTCCATGTACTTACTCAACATATCGTGGAATCACAACGACATGTTGG

GGCCGAGGGCAATGCCCATCTTCTGCTTGTCAAAATACACTTATTTGGAC

CAATGGACATCGTGTCACCTATCAGAAGAGCAGTCGGTACAACTTAAAGG

GGCATATTTCAGAAGGAGATGTGTCCTTGACGATAGAGAACTCTGTTGAG

AGTGACAGTGGTCTGTATTGTTGTCGAGTGGAGATTCCTGGATGGTTTAA

TGATCAGAAAGTGACCTTTTCATTGCAAGTTAAACCAGAGATTCCCACAC

GTCCTCCAACAAGACCCACAACTACAAGGCCCACAGCTACAGGAAGACCC

ACGACTATTTCAACAAGATCCACACATGTACCAACATCAATCAGAGTCTC

TACCTCCACTCCTCCAACATCTACACACACATGGACTCACAAACCAGAAC

CCACTACATTTTGTCCCCATGAGACAACAGCTGAGGTGACAGGAATCCCA

TCCCATACTCCTACAGACTGGAATGGCACTGTGACATCCTCAGGAGATAC

CTGGAGTAATCACACTGAAGCAATCCCTCCAGGGAAGCCGCAGAAAAACC

CTACTAAGGGCTTCTATGTTGGCATCTGCATCGCAGCCCTGCTGCTACTG

CTCCTTGTGAGCACCGTGGCTATCACCAGGTACATACTTATGAAAAGGAA

GTCAGCATCTCTAAGCGTGGTTGCCTTCCGTGTCTCTAAGATTGAAGCTT

TGCAGAACGCAGCGGTTGTGCATTCCCGAGCTGAAGACAACATCTACATT

GTTGAAGATAGACCTTGA

SEQ ID NO: 7; Tim-4 Human Nucleic Acid Variant #1
ATGTCCAAAGAACCTCTCATTCTCTGGCTGATGATTGAGTTTTGGTGGCT

TTACCTGACACCAGTCACTTCAGAGACTGTTGTGACGGAGGTTTTGGGTC

ACCGGGTGACTTTGCCCTGTCTGTACTCATCCTGGTCTCACAACAGCAAC

AGCATGTGCTGGGGGAAAGACCAGTGCCCCTACTCCGGTTGCAAGGAGGC

GCTCATCCGCACTGATGGAATGAGGGTGACCTCAAGAAAGTCAGCAAAAT

ATAGACTTCAGGGGACTATCCCGAGAGGTGATGTCTCCTTGACCATCTTA

AACCCCAGTGAAAGTGACAGCGGTGTGTACTGCTGCCGCATAGAAGTGCC

TGGCTGGTTCAACGATGTAAAGATAAACGTGCGCCTGAATCTACAGAGAG

CCTCAACAACCACGCACAGAACAGCAACCACCACCACACGCAGAACAACA

ACAACAAGCCCCACCACCACCCGACAAATGACAACAACCCCAGCTGCACT

TCCAACAACAGTCGTGACCACACCCGATCTCACAACCGGAACACCACTCC

AGATGACAACCATTGCCGTCTTCACAACAGCAAACACGTGCCTTTCACTA

ACCCCAAGCACCCTTCCGGAGGAAGCCACAGGTCTTCTGACTCCCGAGCC

TTCTAAGGAAGGGCCCATCCTCACTGCAGAATCAGAAACTGTCCTCCCCA

GTGATTCCTGGAGTAGTGCTGAGTCTACTTCTGCTGACACTGTCCTGCTG

ACATCCAAAGAGTCCAAAGTTTGGGATCTCCCATCAACATCCCACGTGTC

AATGTGGAAAACGAGTGATTCTGTGTCTTCTCCTCAGCCTGGAGCATCTG

ATACAGCAGTTCCTGAGCAGAACAAAACAACAAAAACAGGACAGATGGAT

GGAATACCCATGTCAATGAAGAATGAAATGCCCATCTCCCAACTACTGAT

GATCATCGCCCCCTCCTTGGGATTTGTGCTCTTCGCATTGTTTGTGGCGT

TTCCTGAGAGGGAAACTCATGGAAACCTATTGTTCGCAGAAACACACA

AGGCTAGACTACATTGGAGATAGTAAAAATGTCCTCAATGACGTGCAGCA

TGGAAGGGAAGACGAAGACGGCCTTTTTACCCTCTAACAACGCAGTAGCA

TGTTAG

SEQ ID NO: 8; Tim-4 Mouse Nucleic Acid (NM_178759)
AGGAAATGGAGAAAGCAGCTCAGAGAAAGGGAGGACGGAGATAAGGGAAG

GCATGGCACACAACAGAGATGGATGGACAGTCTGAGGCTGAGAGAGGGCT

AGTGATTTCTCGGACACTTGGGCAGTAGAACCCATACCACCCTGTTCTCT

GGGATCCGATGGCCTTGGAGAGGGGCTGCAGGGCCCGAGGACACCAACT

CTTCCCAGAGCGCTGGCATGGAGCCAGACTGAAATTACCATGTGTCCAAA

TTAAAATTGCGTACTTCAAGGATTATTTGAAGGACTATTCTTAGACCCTT

TTAAGAAGATTTTTTAAAAAAACAGTTACTGGCTGCAGACACGGAAATGC

TCTGACTGCTGTAGAGCCAGTGGGCCCTTTAGGGGAGCTCCAGCCCTGTG

GAAGCCAGACAACCAACTTGAAGCCATTTCCAAATTGTGGGTGGTGATCC

ATTTCAAGTTATGAAATGAATTTGATGATTCAAGGCCATCGTTTATTAAA

ACTAATTACCTCGTGCCGAATTCGGCACGAGGGGCTTCTCATCCTCTGGC

TGGTGACGGAGCTCTGGTGGCTTTATCTGACACCAGCTGCCTCAGAGGAT

ACAATAATAGGGTTTTTGGGCCAGCCGGTGACTTTGCCTTGTCATTACCT

CTCGTGGTCCCAGAGCCGCAACAGTATGTGCTGGGGCAAAGGTTCATGTC

CCAATTCCAAGTGCAATGCAGAGCTTCTCCGTACAGATGAACAAGAATC

ATCTCCAGGAAGTCAACAAAATATACACTTTTGGGGAAGGTCCAGTTTGG

TGAAGTGTCCTTGACCATCTCAAACACCAATCGAGGTGACAGTGGGGTGT

ACTGCTGCCGTATAGAGGTGCCTGGCTGGTTCAATGATGTCAAGAAGAAT

GTGCGCTTGGAGCTGAGGAGAGCCACAACAACCAAAAAACCAACAACAAC

CACCCGGCCAACCACCACCCCTTATGTGACCACCACCACCCCAGAGCTGC

TTCCAACAACAGTCATGACCACATCTGTTCTCCCAACCACCACACCACCC

CAGACACTAGCCACCACTGCCTTCAGTACAGCAGTGACCACGTGCCCCTC

AACAACACCTGGCTCCTTCTCACAAGAAACCACAAAAGGGTCCGCCTTCA

CTACAGAATCAGAAACTCTGCCTGCATCCAATCACTCTCAAAGAAGCATG

ATGACCATATCTACAGACATAGCCGTACTCAGGCCCACAGGCTCTAACCC

TGGGATTCTCCCATCCACTTCACAGCTGACGACACAGAAAACAACATTAA

CAACAAGTGAGTCTTTGCAGAAGACAACTAAATCACATCAGATCAACAGC

AGACAGACCATCTTGATCATTGCCTGCTGTGTGGGATTTGTGCTAATGGT

GTTATTGTTTCTGGCGTTTCTCCTTCGAGGGAAAGTCACAGGAGCCAACT

GTTTGCAGAGACACAAGAGGCCAGACAACACTGAAGATAGTGACAGCGTC

CTCAATGACATGTCACACGGGAGGGATGATGAAGACGGGATCTTCACTCT

CTGACTCACCATCTTTATTAGGATTAAGGATAGGGAATGGCACTTGAAT

TGTCAAAATAAGTTTGGGGACATTGTAATTTCCGTTTAAAGTCTCACTCT

GTTTACTGATGCTGTGGGTCCTGTCTGGTTGTATCTTCCCACATGAAGGT

GTTTTAGAGACACATCTTCCCTGCCTCGTGCCTTAGTCCTCTTCGTTGTT

TTGTGGCTAGGTGACTTTTCACACTGGGCTTGAACACTGTCAGTGATGGT

GAAATCCTTGCCACAGCTTTGGGAGTCTCTTGCAGTCTCCCAGCAGTAGA

GGGAGTTAGAAAATATCCAGAGGGGAAAAAAAATCTCTCTTTTCAGACAGT

ATCTGCTTTATTGGTGGTAGCTGAATTTCATTTATACAGAGCTCCTTTAA

CCTGTCTGTCTTCTTCTTGGTATCTAAGCTGCCTTTTGTTTTTGTTTTTG

TTTTTGTTTTTATGATATTAACTTCTTTTCACATTCAAGTTTCTTTAAAG

TTGACTATAGTGCCTTCTGAACTCTTGCAGAGAGTTTGGATTTTGGAAGC

TGCCAGGTACCTATCACAGCAGGGTGCCAGTGACAAGGATGGTGTACAA

ATGAAACACTGAAGCTATCCAAATAAATTCCTCTAAGTGTAATTCATTTT

ACTGCAGCACAGGAAGAACAAATTTGTCTTACAACTTTAATAATTAGTAC

CATTATGAACCCTAGGAGAGAAATAAGAGCAAATACCTGTTGAATAAATG

AATGTAAGAAAAAAAAAAAAAAAAAAAAAAAA

SEQ ID NO: 9; Soluble form of mouse Tim-4;
MSKGLLLLWLVMELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTRKVTGANCLQRHKRPDNTEDSDSVLNDMSHGRDDEDGIFTL

SEQ ID NO: 10; Mouse Tim-4 splice variant,
lacking exon 6;
MSKGLLLLWLVMELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTTPELLPTTVMTTSVLPTTTPPQTLATTAFSTAVTTCPSTTPGSFS

QETTKGSAITTESETLPASNHSQRSMMTISTDIAVLRPTGSNPGILPSTS

QLTTQKTNQQQTDHLDHCLLCGICANGVIVSGVSPSRESHRSQLFAETQE

ARQH

SEQ ID NO: 11; Human Soluble Tim-4 Isoform;
MSKEPLILWLMIEFWWLYLTPVTSETVVTEVLGHRVTLPCLYSSWSHNSN

SMCWGKDQCPYSGCKEALIRTDGMRVTSRKSAKYRLQGTIPRGDVSLTIL

NPSESDSGVYCCRIEVPGWFNDVKINVRLNLQRASTTHRTATTTTRRTT

TTSPTTTRQMTTTPAALPTTVVTTPDLTTGTPLQMTTIAVFTTANTCLSL

TPSTLPEEATGLLTPEPSKEGPILTAESETVLPSDSWSSAESTSADTVLL

TSKESKVWDLPSTSHVSMWKTSDSVSSPQPGGKLMETYCSQKHTRLDYIG

DSKNVLNDVQHGREDEDGLFTL

SEQ ID NO: 12; Mouse Tim-4 Alternate N-terminal Isoform (NP_848874)

MNLMIQGHRLLKLITSCRIRHEGLLILWLVTELWWLYLTPAASEDTIIGF
LGQPVTLPCHYLSWSQSRNSMCWGKGSCPNSKCNAELLRTDGTRIISRKS
TKYTLLGKVQFGEVSLTISNTNRGDSGVYCCRIEVPGWFNDVKKNVRLEL
RRATTTKKPTTTTRPTTTPYVTTTTPELLPTTVMTTSVLPTTTPPQTLAT
TAFSTAVTTCPSTTPGSFSQETTKGSAFTTESETLPASNHSQRSMMTIST
DIAVLRPTGSNPGILPSTSQLTTQKTTLTTSESLQKTTKSHQINSRQTIL
IIACCVGFVLMVLLFLAFLLRGKVTGANCLQRHKRPDNTEDSDSVLNDMS
HGRDDEDGIFTL

SEQ ID NO: 13; Mouse Tim-2 Polypeptide (NP_599010)

MNQIQVFISGLILLLPGAVESHTAVQGLAGHPVTLPCIYSTHLGGIVPMC
WGLGECRHSYCIRSLIWTNGYTVTHQRNSRYQLKGNISEGNVSLTIENTV
VGDGGPYCCVVEIPGAFHFVDYMLEVKPEISTSPPTRPTATGRPTTISTR
STHVPTSTRVSTSTSPTPAHTETYKPEATTFYPDQTTAEVTETLPDTPAD
WHNTVTSSDDPWDDNTEVIPPQKPQKNLNKGFYVGISIAALLILMLLSTM
VITRYVVMKRKSESLSFVAFPISKIGASPKKVVERTRCEDQVYIIEDTPY
PEEES

---

We claim:

1. A method of treating a Th2-mediated disorder, or of reducing the frequency, severity or onset of symptoms of the Th2-mediated disorder, in a subject in need of such treatment, the method comprising administering to the subject a therapeutically effective amount of an agent, said agent comprising a polypeptide consisting essentially of
   (i) amino acids 31-133 of SEQ ID NO: 3;
   (ii) amino acids 31-134 of SEQ ID NO: 4;
   (iii) a conservative substitution polypeptide having an amino acid sequence at least 95% identical to amino acids 31-133 of SEQ ID NO: 3, and wherein the polypeptide binds to human Tim-1 (SEQ ID NO: 1) and increases the activity of Tim-1 to signal into T cells; or
   (iv) a conservative substitution polypeptide having an amino acid sequence at least 95% identical to amino acids 31-134 of SEQ ID NO: 4, and wherein the polypeptide binds to mouse Tim-1 (SEQ ID NO: 2) and increases the activity of Tim-1 to signal into T cells.

2. The method of claim 1, wherein the Th2-mediated disorder is an atopic disorder.

3. The method of claim 1, wherein the Th2 mediated disorder is asthma, an allergy, allergic rhinitis, gastrointestinal allergy, food allergy, Th2-mediated conjunctivitis or Th2-mediated glomerulonephritis.

4. The method of claim 1, wherein the agent further comprises (a) human serum albumin; or (b) an Fc domain of an immunoglobulin.

5. The method of claim 1, wherein the agent increases phosphorylation of the intracellular domain of Tim-1.

6. The method of claim 1, wherein the agent comprises a polypeptide consisting essentially amino acids 31-134 of SEQ ID NO: 4.

7. A method of promoting a Th1 immune response in a subject in need thereof, the method comprising administering to the subject a therapeutically effective amount of an agent said agent comprising a polypeptide consisting essentially of
   (i) amino acids 31-133 of SEQ ID NO: 3;
   (ii) amino acids 31-134 of SEQ ID NO: 4;
   (iii) a conservative substitution polypeptide having an amino acid sequence at least 95% identical to amino acids 31-133 of SEQ ID NO: 3, and wherein the polypeptide binds to human Tim-1 (SEQ ID NO: 1) and increases the activity of Tim-1 to signal into T cells; or
   (iv) a conservative substitution polypeptide having an amino acid sequence at least 95% identical to amino acids 31-134 of SEQ ID NO: 4, and wherein the polypeptide binds to mouse Tim-1 (SEQ ID NO: 2) and increases the activity of Tim-1 to signal into T cells.

8. The method of claim 7, wherein the subject is afflicted with a hyperplastic condition.

9. The method of claim 8, wherein the hyperplastic condition is renal cancer, Kaposi's sarcoma, chronic leukemia, prostate cancer, breast cancer, sarcoma, pancreatic cancer, leukemia, ovarian carcinoma, rectal cancer, throat cancer, melanoma, colon cancer, bladder cancer, lymphoma, mastocytoma, lung cancer, mammary adenocarcinoma, pharyngeal squamous cell carcinoma, testicular cancer, gastrointestinal cancer, or stomach cancer, or a combination thereof.

10. A method of treating eosinophilia, or of reducing the frequency severity or onset of symptoms of eosinophilia, in a subject in need of such treatment, the method comprising administering to the subject a therapeutically effective amount of an agent, said agent comprising a polypeptide consisting essentially of
    (i) amino acids 31-133 of SEQ ID NO: 3
    (ii) amino acids 31-134 of SEQ ID NO: 4;
    (iii) a conservative substitution polypeptide having an amino acid sequence at least 95% identical to amino acids 31-133 of SEQ ID NO: 3, and wherein the polypeptide binds to human Tim-1 (SEQ ID NO: 1) and increases the activity of Tim-1 to signal into T cells; or
    (iv) a conservative substitution polypeptide having an amino acid sequence at least 95% identical to amino acids 31-134 of SEQ ID NO: 4,
    and wherein the polypeptide binds to mouse Tim-1 (SEQ ID NO: 2) and increases the activity of Tim-1 to signal into T cells.

11. A method of treating a Th2-mediated disorder, or of reducing the frequency, severity or onset of symptoms of a Th2-mediated disorder, in a subject in need of such treatment, the method comprising administering to the subject a therapeutically effective amount of an agent, said agent comprising a polypeptide consisting essentially of
    (i) amino acids 31-318 of SEQ ID NO: 3; or
    (ii) amino acids 31-281 of SEQ ID NO: 4.

12. A method of promoting a Th1 immune response in a subject in need thereof, the method comprising administering to the subject a therapeutically effective amount of an agent said agent comprising a polypeptide consisting essentially of
    (i) amino acids 31-318 of SEQ ID NO: 3; or
    (ii) amino acids 31-281 of SEQ ID NO: 4.

* * * * *